(12) United States Patent
Johnson et al.

(10) Patent No.: US 11,975,046 B2
(45) Date of Patent: May 7, 2024

(54) MEDICAL USE OF INTERFERON-LAMBDA FOR THE TREATMENT OF FIBROSIS

(71) Applicants: UCB BIOPHARMA SRL, Brussels (BE); FIVE PRIME THERAPEUTICS, INC., Thousand Oaks, CA (US)

(72) Inventors: Timothy Scott Johnson, Berkshire (GB); Breda Twomey, Berkshire (GB); Janine Powers, Wilmington, DE (US); Danielle E. Kellar, San Francisco, CA (US)

(73) Assignees: UCB BIOPHARMA SRL, Brussels (BE); FIVE PRIME THERAPEUTICS, INC., Thousand Oaks, CA (US)

( * ) Notice: Subject to any disclaimer, the term of this patent is extended or adjusted under 35 U.S.C. 154(b) by 0 days.

(21) Appl. No.: 18/343,944

(22) Filed: Jun. 29, 2023

(65) Prior Publication Data
US 2024/0000893 A1    Jan. 4, 2024

Related U.S. Application Data

(63) Continuation of application No. 18/469,236, filed as application No. PCT/EP2017/083948 on Dec. 20, 2017, now abandoned.

(30) Foreign Application Priority Data

Dec. 20, 2016 (GB) ..................... 1621728

(51) Int. Cl.
| | |
|---|---|
| A61K 38/21 | (2006.01) |
| A61K 45/06 | (2006.01) |
| A61K 47/60 | (2017.01) |
| A61P 1/00 | (2006.01) |
| A61P 1/16 | (2006.01) |
| A61P 13/12 | (2006.01) |
| A61P 17/00 | (2006.01) |

(52) U.S. Cl.
CPC .............. *A61K 38/21* (2013.01); *A61K 45/06* (2013.01); *A61K 47/60* (2017.08); *A61P 1/00* (2018.01); *A61P 1/16* (2018.01); *A61P 13/12* (2018.01); *A61P 17/00* (2018.01)

(58) Field of Classification Search
None
See application file for complete search history.

(56) References Cited

U.S. PATENT DOCUMENTS

| | | |
|---|---|---|
| 2006/0204473 A1 | 9/2006 | Blatt et al. |
| 2007/0258946 A1* | 11/2007 | Blatt ................... A61K 38/212 424/85.5 |
| 2010/0260704 A1 | 10/2010 | Berenguer et al. |
| 2011/0243888 A1* | 10/2011 | Sheppard ............... C07K 14/54 435/243 |

FOREIGN PATENT DOCUMENTS

| | | |
|---|---|---|
| JP | 2011/522834 A | 8/2011 |
| WO | 92/22853 A1 | 12/1992 |
| WO | 02/81507 A2 | 10/2002 |
| WO | 2004/019863 A2 | 3/2004 |
| WO | 2004/078193 A1 | 9/2004 |
| WO | 2004/078207 A1 | 9/2004 |
| WO | 2004/105684 A2 | 12/2004 |
| WO | 2005/003169 A2 | 1/2005 |
| WO | 2005/003170 A2 | 1/2005 |
| WO | 2005/003171 A2 | 1/2005 |
| WO | 2005/067454 A1 | 7/2005 |
| WO | 2005/110478 A2 | 11/2005 |
| WO | 2005/113605 A1 | 12/2005 |
| WO | 2009/040562 A1 | 4/2009 |
| WO | 2010/045261 A1 | 4/2010 |
| WO | 2010/048468 A1 | 4/2010 |
| WO | 2011/075605 A2 | 6/2011 |
| WO | 2011/141787 A1 | 11/2011 |
| WO | 2013/148272 A1 | 10/2013 |
| WO | 2017/143253 A1 | 8/2017 |

OTHER PUBLICATIONS

Adair et al., Therapeutic Antibodies, Drug Design Reviews—Online, 2(3):209-217 (2005).
Andersen et al., Peginterteron Lambda-la, a New Therapeutic for Hepatitis C Infection, from Bench to Clinic, Journal of Clinical and Translational Hepatology, 1:116-124, (2013).
Andreakos et al., Interferon-lambdas: Front-Line Guardians of Immunity and Homeostasis in the Respiratory Tract Frontiers in Immunology, 8:1-7, Article1232, (2017).
Azuma, et al., Interferon—β Inhibits Bleomycin-Induced Lung Fibrosis by Decreasing Transforming Growth Factor-β and Thrombospondin, American Journal of Respiratory Cell and Molecular Biology, vol. 32 (2005).
Bach et al., The IFN Gamma Receptor: A paradigm for cytokine receptor signaling, Ann Rev. Immunol. 15:563-591, (1997).
Bhushal et al., Cell polarization and epigenetic status shape the heterogeneous response to type I11 interferons in Intestinal epithelial cells, Frontiers in Immunology, 8:1-18, article 671, (2017).
Biron et al. Interferons alpha and beta as immune regulators—a new look, Immunity, 14(6):661-664, (2001).
Blazek et al., IFN-lambda resolves inflammation via suppression of neutrophil infiltration and IL-1beta production, J. Exp. Med., 212(6):845-853, (2015).

(Continued)

*Primary Examiner* — Jennifer E Graser

(74) *Attorney, Agent, or Firm* — Melissa E. Karabinis

(57) ABSTRACT

The present invention relates to methods for the treatment of fibrosis. The invention discloses new research which demonstrates that interferon-lambda has directly acting anti-fibrotic effects both in vitro and in vivo and may be used to provide effective new therapies for the treatment of multiple types of fibrosis.

10 Claims, 51 Drawing Sheets

Figure 1A:
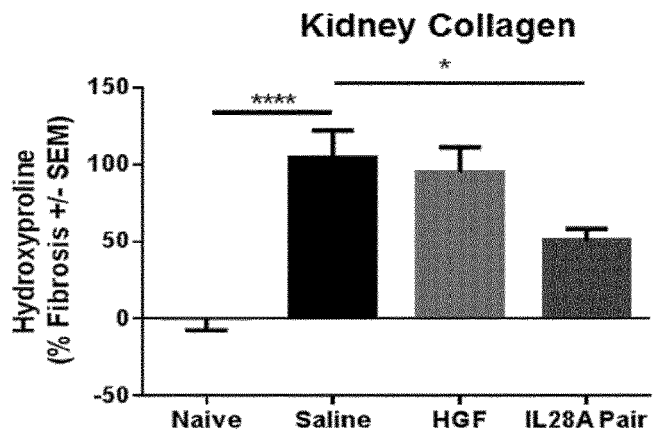

Specification includes a Sequence Listing.

(56) References Cited

OTHER PUBLICATIONS

Blumer et al., SOCS1 is an inducible negative regulator of interferon lambda (IFN-lambda)-induced gene expression in vivo, J. Biol. Chem., 292(43):17928-17938, (2017).
Bochud et al., IL28B Alleles associated with poor hepatitis C virus (HCV) clearance protect against inflammation and fibrosis in patients infected with non-1 HCV genotypes, Hepatology 5(2):384-394, (2012).
Broggi et al., IFN-lambda suppresses intestinal inflammation by non-translational regulation of neutrophil function, Nature Immunology, 18(10):1084-1093, (2017).
Buster, et al., Peginterferon Alpha-2b Is Safe and Effective in HBeAg-Positive Chronic Hepatitis B Patients with Advanced Fibrosis, Hepatology, vol. 46, No. 2 (2007).
Chapman, PEGylated antibodies and antibody fragments for improved therapy: a review, Advanced Drug Delivery Reviews, 54:531-545, (2002).
Chiriac et al., Activation of epithelial signal transducer and activator of transcription 1 by interleukin 28 controls mucosal healing in mice with colitis and is increased in mucosa of patients with inflammatory bowel disease, Gastroenterology, 153:123-138, (2017).
Chow & Gale, SnapShot: Interferon signaling, Cell, 163(7):1808-1808.e1, (2015).
Donnelly et al., Interferon-Lambda: A new addition to an old family, Journal of Interferon & Cytokine Research, 30(8):555-564, (2010).
Doyle et al., Interleukin-29 uses a type 1 interferon-like program to promote antiviral responses in human hepatocytes, Hepatology, 44(4):896-906, (2006).
Eslam et al., Genome-wide association studies and hepatitis C: Harvesting the benefits of the genomic revolution, Semin Liver Dis., 35:402-420, (2015).
Eslam et al., Interferon-lambda rs12979860 genotype and liver fibrosis in viral and non-viral chronic liver disease, Nature Communications, 6:6422-6432, (2015).
Flisiak et al., Informa Heatcare, Expert Opinion, "Emerging treatments for hepatitis C", 18(4) p. 461-475, Oct. 8, 2013.
Gad et al., Interferon-lambda is functionally an interferon but structurally related to the interleukin-10 family, Journal. Biological Chemistry, 284(31):20869-20875, (2009).
Ge et al., Genetic variation in IL28B predicts hepatitis C treatment-induced viral clearance, Nature 461(7262):399-401,(2009).
Gresser, Interferon should be used to prevent and/or treat Ebola virus disease, Biomedicine & Pharmacotherapy, 71:29, (2015).
Griffiths et al., A systematic analysis of host factors reveals a med23—interferon-lambda regulatory axis against herpes simplex virus type 1 replication, PLoS Pathogens 9:1-19, e1003514, (2013).
Guenterberg et al., IL-29 binds to melanoma cells inducing Jak-STAT signal transduction and apoptosis, Molecular Cancer Therapeutics, 9(2):510-520, (2010).
Guo et al., Genetic variation in interleukin 28B and response to antiviral therapy in patients with dual chronic infection with hepatitis B and C viruses, PLoS One, 8(10):1-6, e77911, (2013).
Hemann et al., IFN-lambda 'guts' neutrophil-mediated inflammation, Nature Immunology, 18(10):1061-1062, (2017).
Holliger et al., Engineered antibody fragments and the rise of single domains, Nature Biotechnology, 23(9):1126-1136, (2005).
Hong et al., Interferon lambda 4 expression is suppressed by the host during viral infection, Journal of Experimental Medicine, 10:1084-1098, (2016).
Huang et al., Immune response in mice that lack the interferon-gamma receptor, Science, 259:1742-1745, (1993).
International Preliminary Report on Patentability received for PCT Patent Application No. PCT/EP2017/083949, mailed Jul. 4, 2019, 8 pages.
International Search Report and Written Opinion received for PCT Patent Application No. PCT/EP2017/083949, mailed Apr. 5, 2018, 11 pages.
JP Application No. 2019-532000 Office Action (Nov. 2, 2021), 7 pages.
Kanefuji et al., Molecular Therapy—Methods & Clinical Development, 1:14029, (2014).
King, et al., Effect of interferon gamma-1b on survival in patients with idiopathic pulmonary fibrosis (INSPIRE): a multicentre, randomized, placebo-controlled trial: Lancet; 374: 222-28, Jun. 30, 2009, DOI: 10.1016/S0140-6736(09)60551-1.
Kolcanov, 1988, Journal of Molecular Evolution, vol. 27, pp. 154-162 (1998).
Koltsida et al., IL-28A (IFN-lambda2) modulates lung DC function to promote Th1 immune skewing and suppress allergic airway disease, EMBO Molecular Medicine, 3(6):348-361, (2011).
Kotenko et al., IFN-lambdas mediate antiviral protection through a distinct class II cytokine receptor complex, Nature Immunology, 4(1):69-77, (2003).
Kotenko, The family of IL-10-related cytokines and their receptors: related, but to what extent?, Cytokine Growth Factor Reviews, 13(3):223-240, (2002).
Li et al., Interferon-lambda induces G1 phase arrest or apoptosis in oesophageal carcinoma cells and produces anti-tumour effects in combination with anti-cancer agents, European Journal of Cancer, 46(1):180-190, (2010).
Liu et al., Hydrodynamics-based transfection in animals by systemic administration of plasmid DNA, Gene Therapy, 6:1258-1266, (1999).
Lutherer, et al., Low-dose oral interferon α possibly retards the progression of idiopathic pulmonary fibrosis and alleviates associated cough in some patients, Thorax May 2011 vol. 66 No. 5, pp. 446-447.
Mahlakoiv et al., Leukocyte-derived IFN-alpha/beta and epithelial IFN-lambda constitute a compartmentalized mucosal defense system that restricts enteric virus infections, PLoS Pathog., 11:1-19, e1004782, (2015).
McFarland et al., IFNL3 (IL28B) favorable genotype escapes hepatitis C virus-induced microRNAs and mRNA decay, Nature Immunology, 15:72-79, (2014).
Miknis et al., Crystal structure of the complex of human interteron-lambda1 with its high affinity receptor interferon-lambdaR1, Journal of Molecular Biology, 404:650-664, (2010).
Mordstein et al., Interferon-lambda contributes to innate immunity of mice against influenza a virus but not against hepatotropic viruses, PLoS Pathog., 4:1-7, e1000151, (2008).
Moreno, et al., Remission of Liver Fibrosis by Interferon—$\alpha_{2b}$, Biochemical Pharmacology, vol. 50, No. 4 pp. 515-220, 1995.
Muir et al., A randomized phase 2b study of peginterferon lambda-1a for the treatment of chronic HCV infection, Journal of Hepatology, 61(6):1238-1246, (2014).
Numasaki et al., IL-28 elicits antitumor responses against murine fibrosarcoma, Journal of Immunology, 178(8):5086-5098,(2007).
Osterlund et al., IFN regulatory factor family members differentially regulate the expression of type III IFN (IFN-lambda) genes1, Journal of Immunology, 179:3434-3442, (2007).
Park et al., IL-29 is the dominant type III interferon produced by hepatocytes during acute hepatitis C virus infection, Hepatology, 56(6):2060-2070, (2012).
Pasquo, 2012, PloS ONE, vol. 7, Issue 2, e32555 (2012).
Pott et al., IFN-lambda determines the intestinal epithelial antiviral host defense, Proc. Natl. Acad. Sci., 108:7944-7949, (2011).
Prokunina-Olsson et al., A variant upstream of IFNL3 (IL28B) creating a novel interferon gene IFNL4 is associated with impaired clearance of hepatitis C virus, Nature Genetics, 45(2):164-171, (2013).
Rallon et al., Association of a single nucleotide polymorphism near the interleukin-28B gene with response to hepatitis C therapy in HIV/hepatitis C virus-coinfected patients, Aids, 24(8):F23-29, (2010).
Sato et al., Antitumor activity of IFN-lambda in murine tumor models1, Journal of Immunology, 176(12):7686-7694, (2006).
Sheppard et al., IL-28, IL-29 and their class II cytokine receptor IL-28R, Nature Immunology, 4(1):63-68, (2003).
Souza-Fonseca-Guimaraes et al., NK cells require IL-28R for optimal in vivo activity, Proc. Natl. Acad Sci 112:E2376-E2384,(2015).

(56) References Cited

OTHER PUBLICATIONS

Sommereynes, et al., IFN-Lambda (IFN-λ) Is Expressed in a Tissue-Dependent Fashion and Primarily Acts on Epithelial Cells In Vivo, PLoS Pathog 4(3): e1000017. doi:10.1371/journal.ppat. 1000017 (2008).
Souza-Fonseca-Guimaraes et al., 2015, Proc. Natl. Acad. Sci. 112: E2376-E2384.
Stahl et al. The alphas, betas, and kinases of cytokine receptor complexes, Cell, 74:587-590, (1993).
Steen et al., 2010, Journal Interferon Cytokine Research 30(8): 597-602.
Suppiah et al., 2009, Nature Genetics 41(10): 1100-1104.
Tanaka et al., 2009, Nature Genetics 41 (10):1105-1109.
Thomas et al., 2012, Gastroenterology 142 (4): 978-988.
Tovey, et al., Safety, Tolerability, and Immunogenicity of Interferons, Pharmaceuticals, 3, 1162-1186; doi:10.3390/ph3041162, (2010).
Verma R., et al., 1998, Journal of Immunological Methods, 216: 165-181.
Wack, et al., Guarding the frontiers: the biology of type III interferons, Nature Immunology, vol. 16, No. 8, Aug. 2015.
Wolk et al., 2013, Science Translational Medicine 5(204): 204ra129.
Zhou et al., 2007, Journal of Virology, 81: 7749-7758.
Zitzmann et al., 2006, Biochem. Biophys. Res. Commun. 344(4):1334-1341.

\* cited by examiner

Figure 1B:
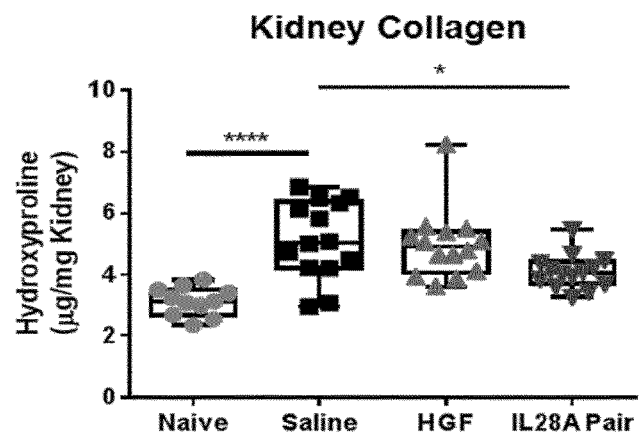

Figure 1: Identification of IL-28A in an Adriamycin model of Kidney disease

Figure 2: Confirmation of IL-28A in an Adriamycin model of Kidney disease

Figure 2 (contd.): Confirmation of IL-28A in an Adriamycin model of Kidney disease

Figure 3A:
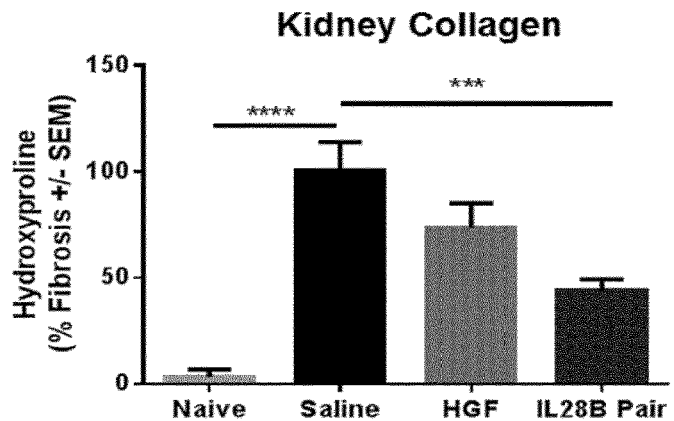
Figure 3B:
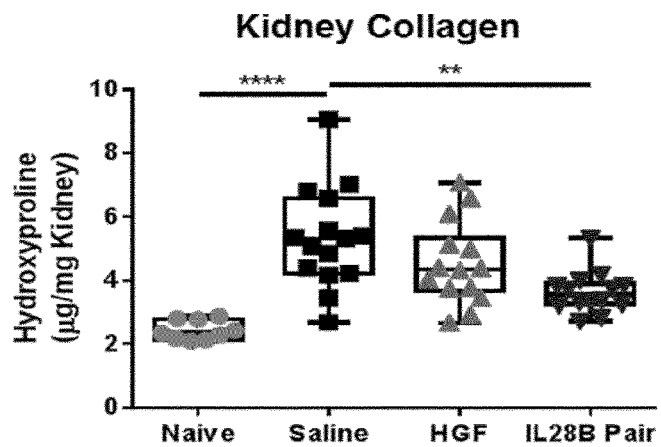

Figure 3: Identification of IL-28B in an Adriamycin model of Kidney disease

Figure 4: Confirmation of IL-28B in an Adriamycin model of Kidney disease

Figure 4: (contd.) Confirmation of IL-28B in an Adriamycin model of Kidney disease

Figure 5: Histological confirmation of IL-28B and IL-28A as anti-fibrotic in an Adriamycin model of Kidney disease
Figure 5a: PSR staining of IL-28B kidney – Adriamycin model of kidney disease
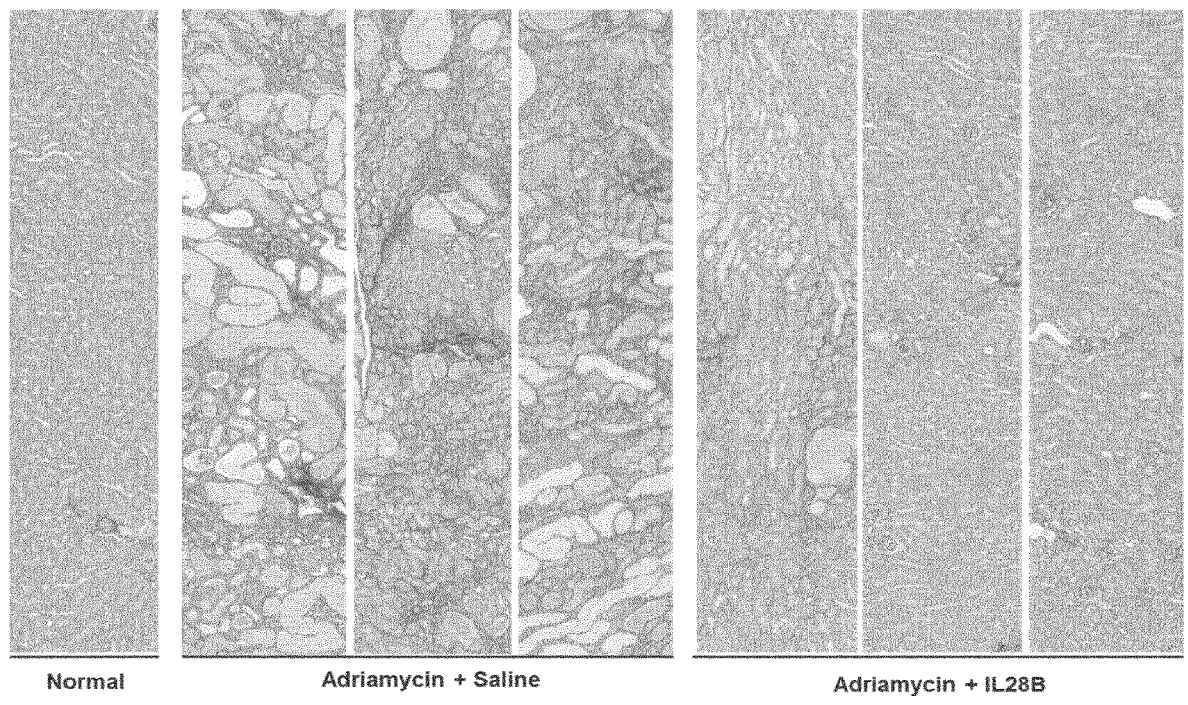

Figure 5 (contd.): Histological confirmation of IL-28B and IL-28A as anti-fibrotic in an Adriamycin model of Kidney disease

Quantification of PSR staining by high content imaging IL-28B

Figure 5 (contd.): Histological confirmation of IL-28B and IL-28A as anti-fibrotic in an Adriamycin model of Kidney disease

Figure 5 (contd.): Histological confirmation of IL-28B and IL-28A as anti-fibrotic in an Adriamycin model of Kidney disease

Figure 5 (contd.): Histological confirmation of IL-28B and IL-28A as anti-fibrotic in an Adriamycin model of Kidney disease

Figure 5 (contd.): Histological confirmation of IL-28B and IL-28A as anti-fibrotic in an Adriamycin model of Kidney disease
Figure 5f: PSR staining of IL-28A kidney – Adriamycin model of kidney disease
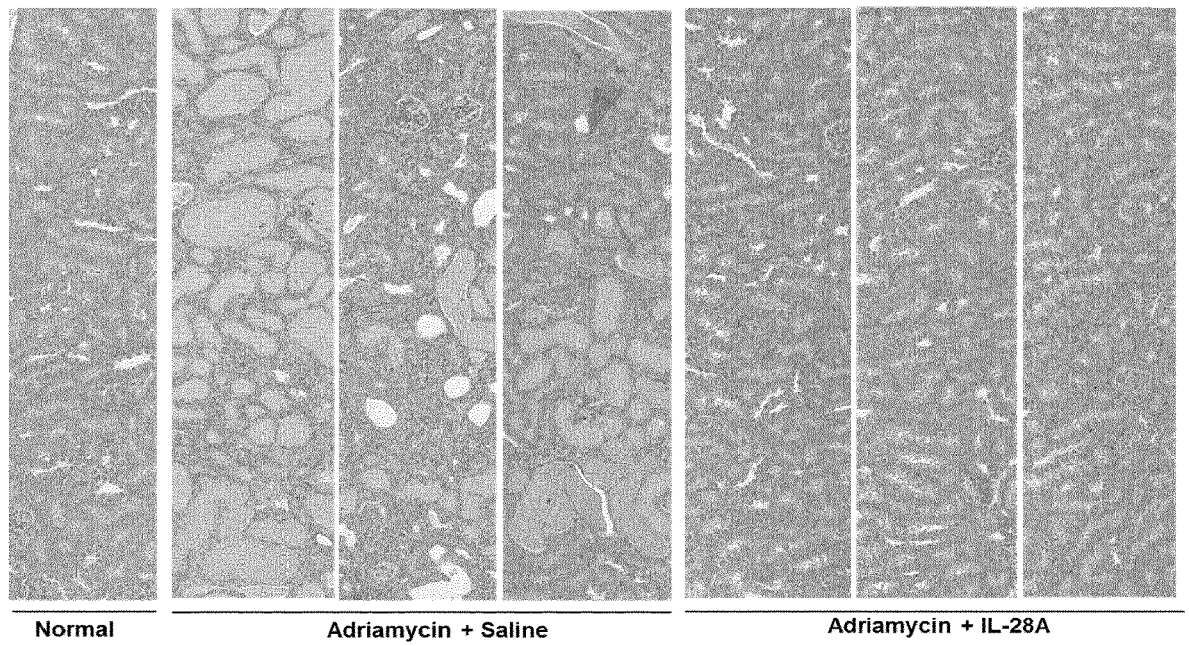
Normal | Adriamycin + Saline | Adriamycin + IL-28A

Figure 5 (contd.): Histological confirmation of IL-28B and IL-28A as anti-fibrotic in an Adriamycin model of Kidney disease

Figure 5 (contd.): Histological confirmation of IL-28B and IL-28A as anti-fibrotic in an Adriamycin model of Kidney disease

Figure 5 (contd.): Histological confirmation of IL-28B and IL-28A as anti-fibrotic in an Adriamycin model of Kidney disease

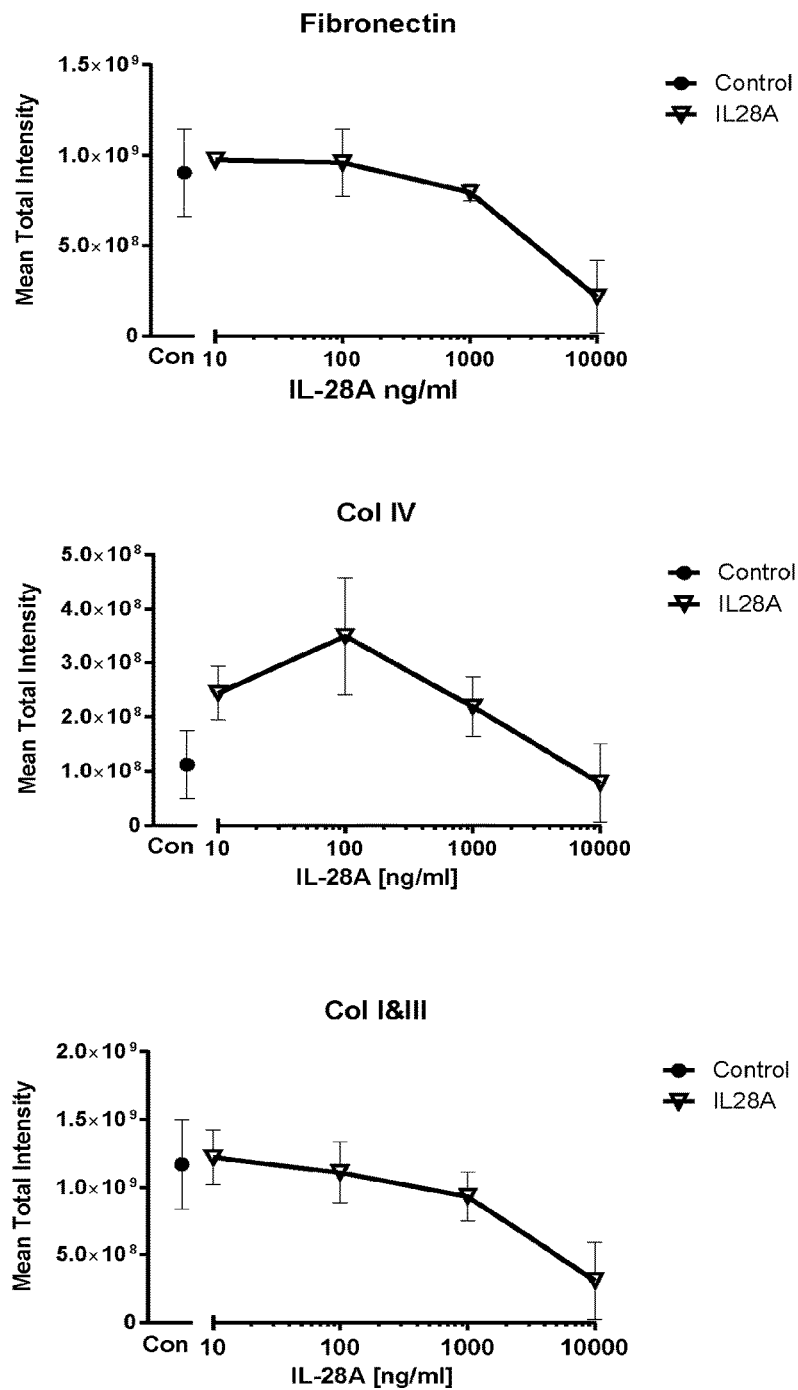
Figure 6(a): Effect of IL-28A in a Liver stellate cell *in vitro* ECM fibrosis model

Figure 6(b): Effect of IL-28A in a Liver stellate cell-hepatocyte *in vitro* ECM fibrosis model
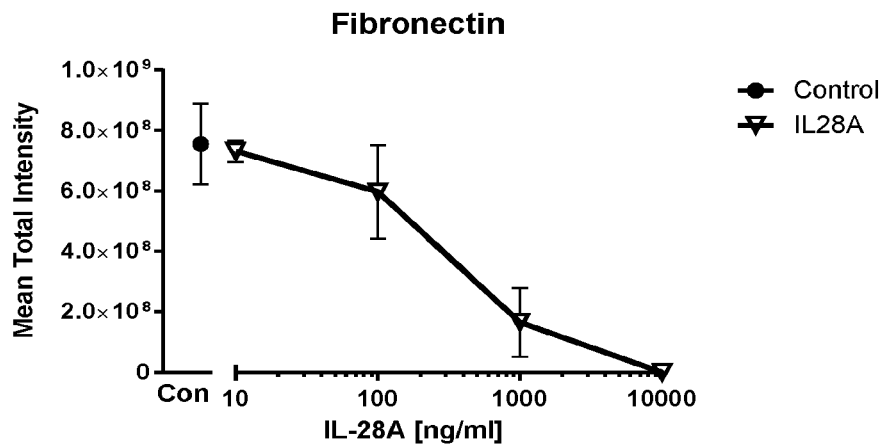
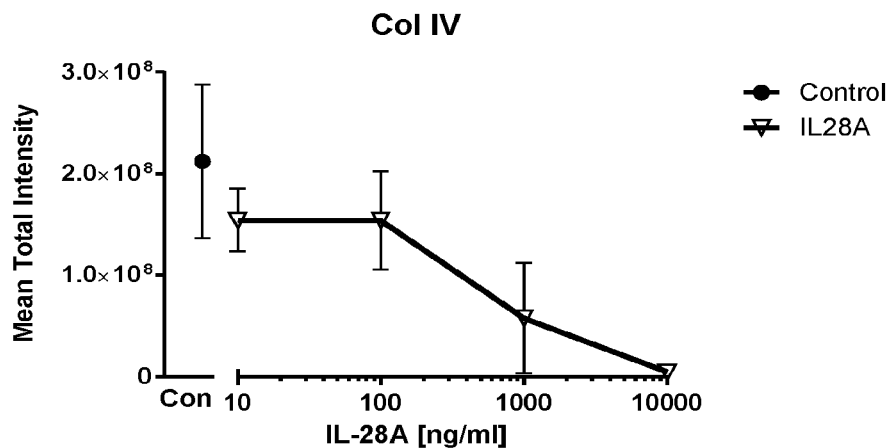
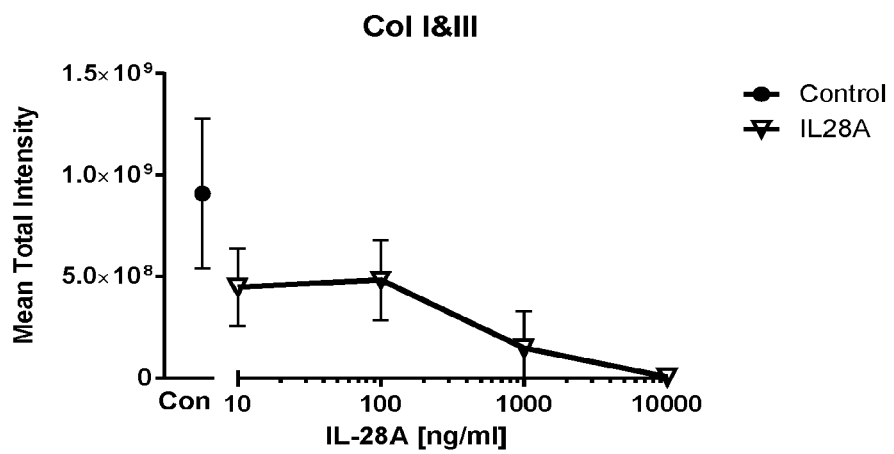

Figure 7(a): Effect of IL-28A and IL-28B in a Liver stellate cell *in vitro* ECM fibrosis model plus TGFβ
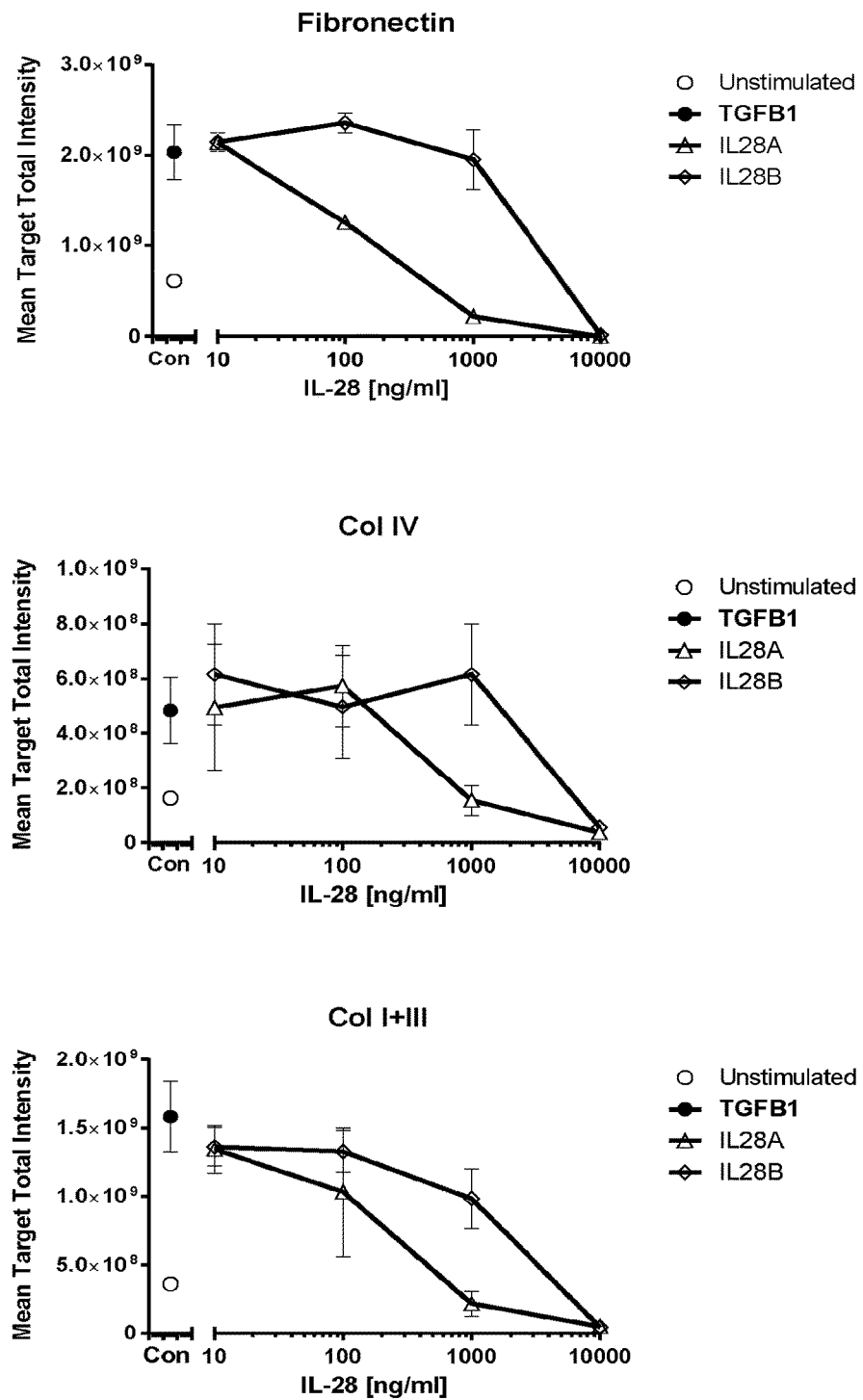

Figure 7(b): Effect of IL-28A and IL-28B in a Liver stellate cell-hepatocyte co-culture plus TGFβ
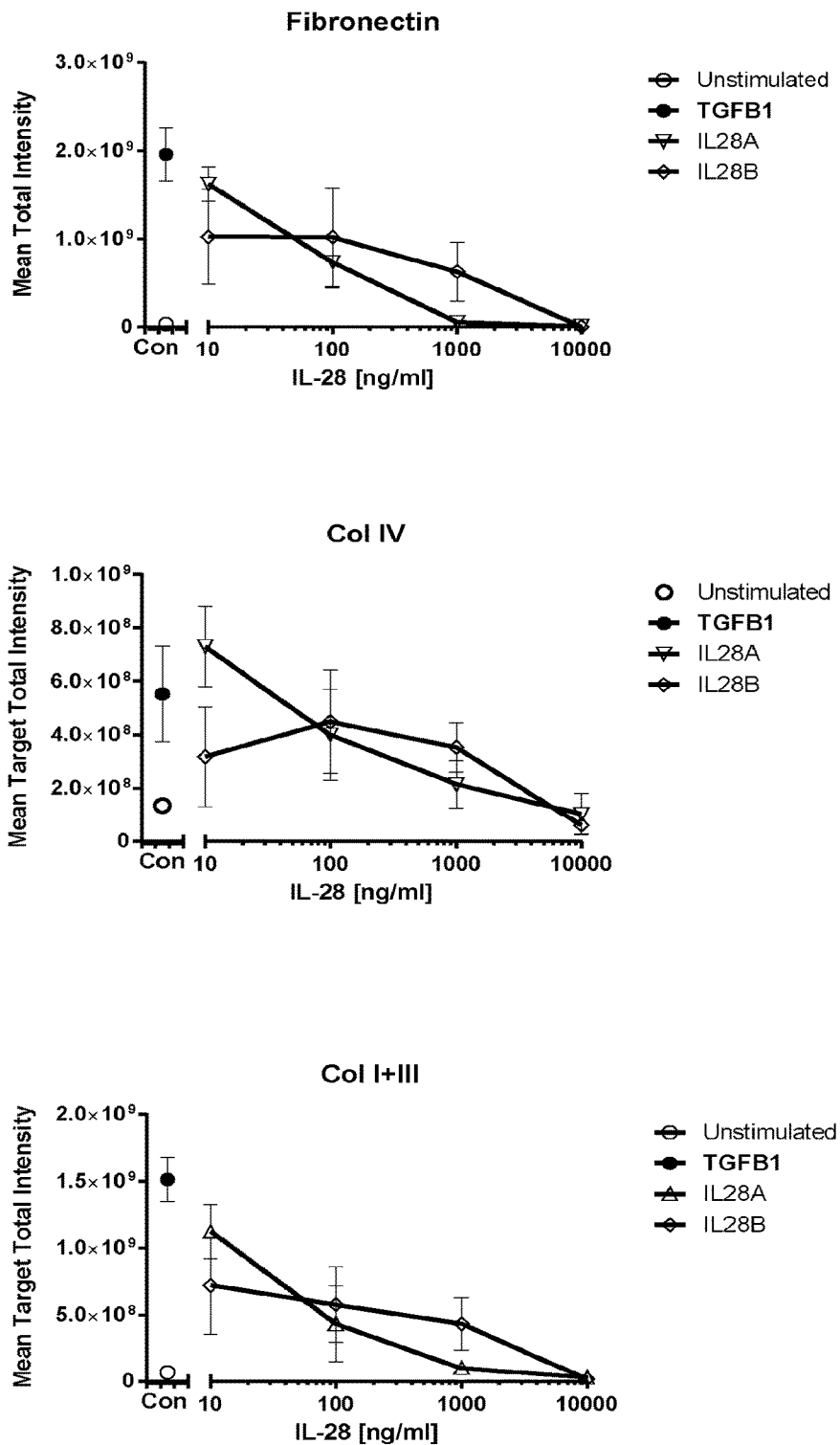

Figure 8: High content images showing the effect of IL-28A and IL-28B in TGFβ1-stimulated stellate cell-hepatocyte co-culture ECM
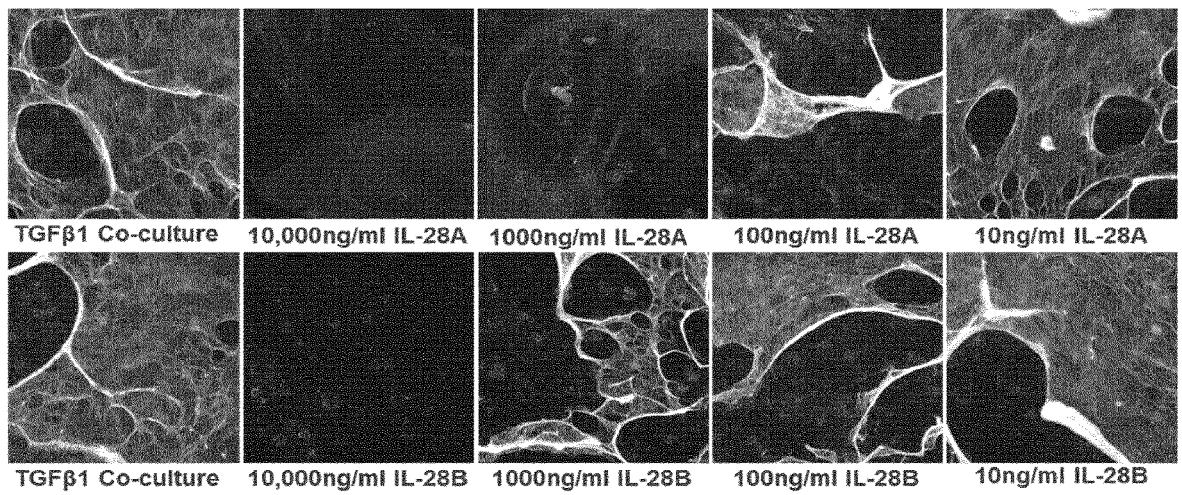

Figure 9: Effect of IL-28A, IL-28B and IL-29 on TGFβ1-stimulated small intestine fibroblast ECM
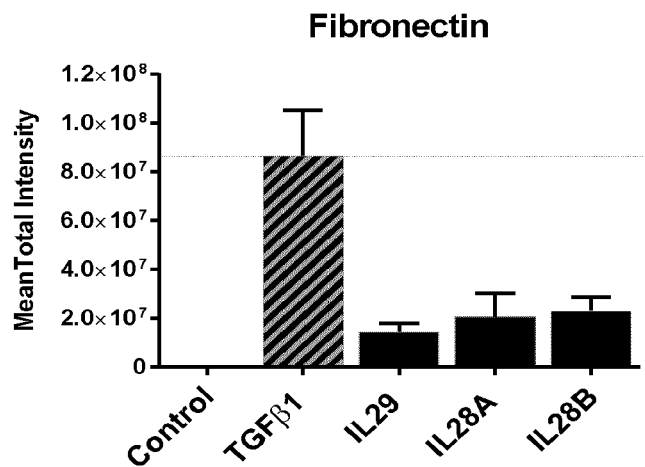
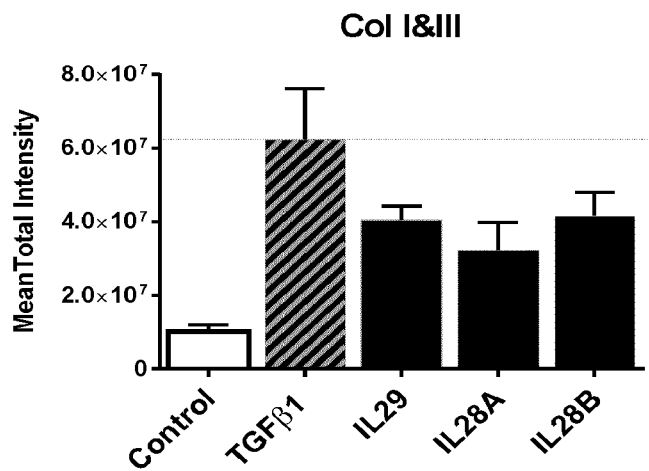
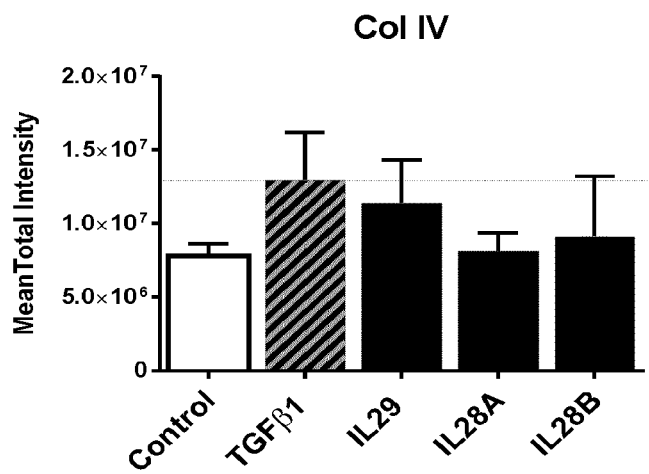

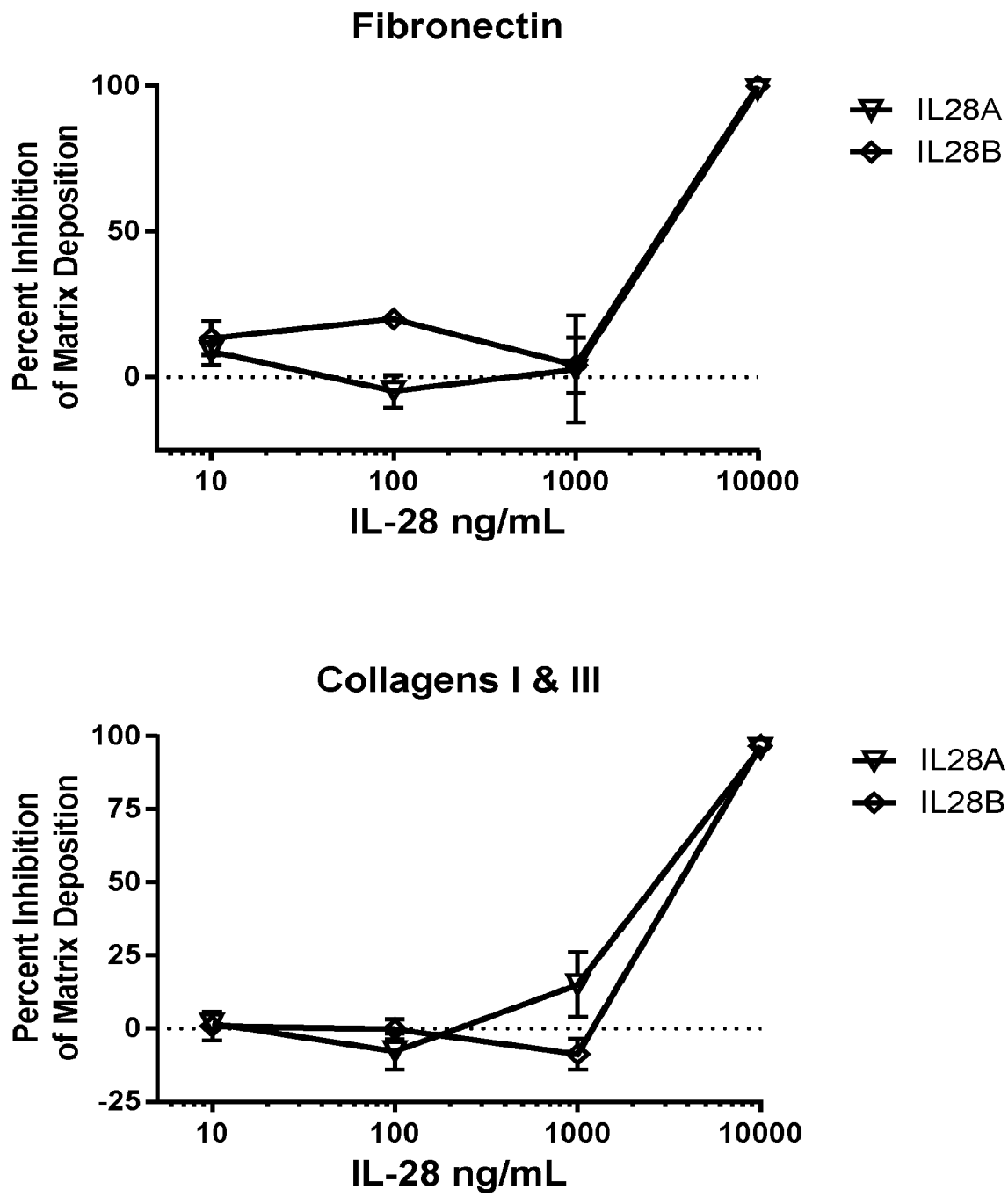
Figure 10: % Inhibition of IL-28A and IL-28B in Skin keratinocyte-fibroblast co-culture ECM

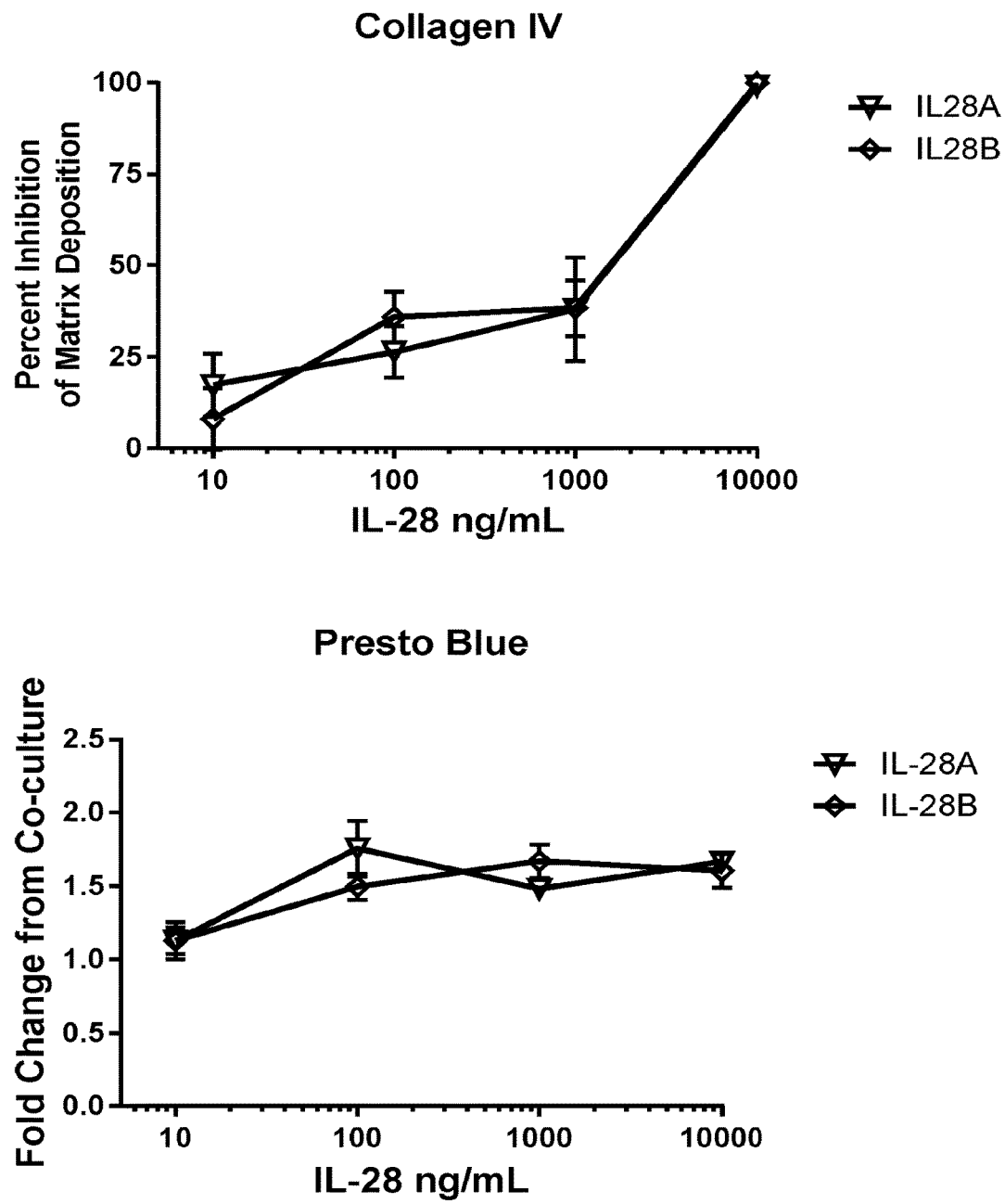
Figure 10 (contd.): % Inhibition of IL-28A and IL-28B in Skin keratinocyte-fibroblast co-culture ECM and cell viability

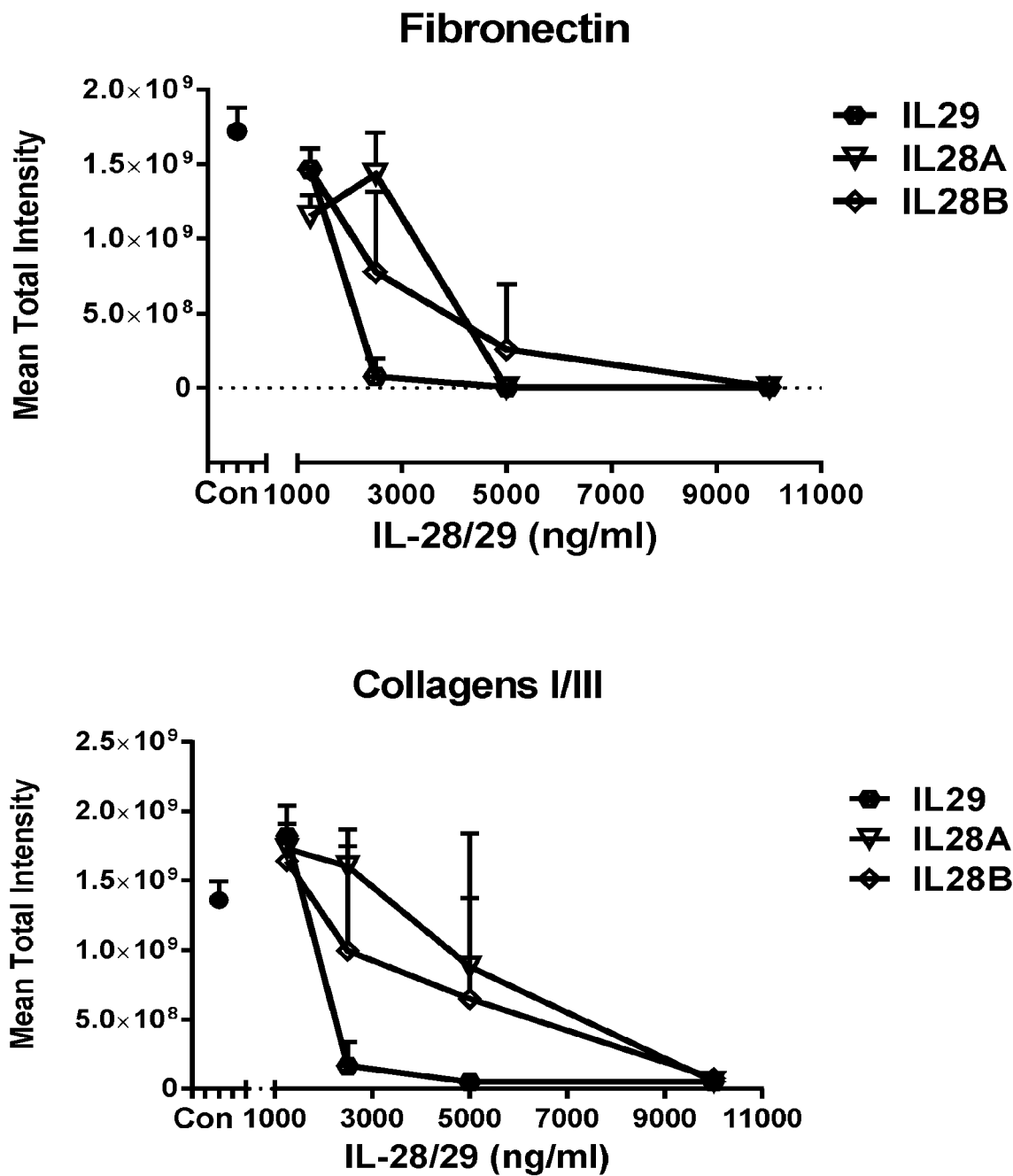
Figure 11: Effect of IL-28A, IL-28B and IL-29 in Skin keratinocyte-fibroblast co-culture ECM

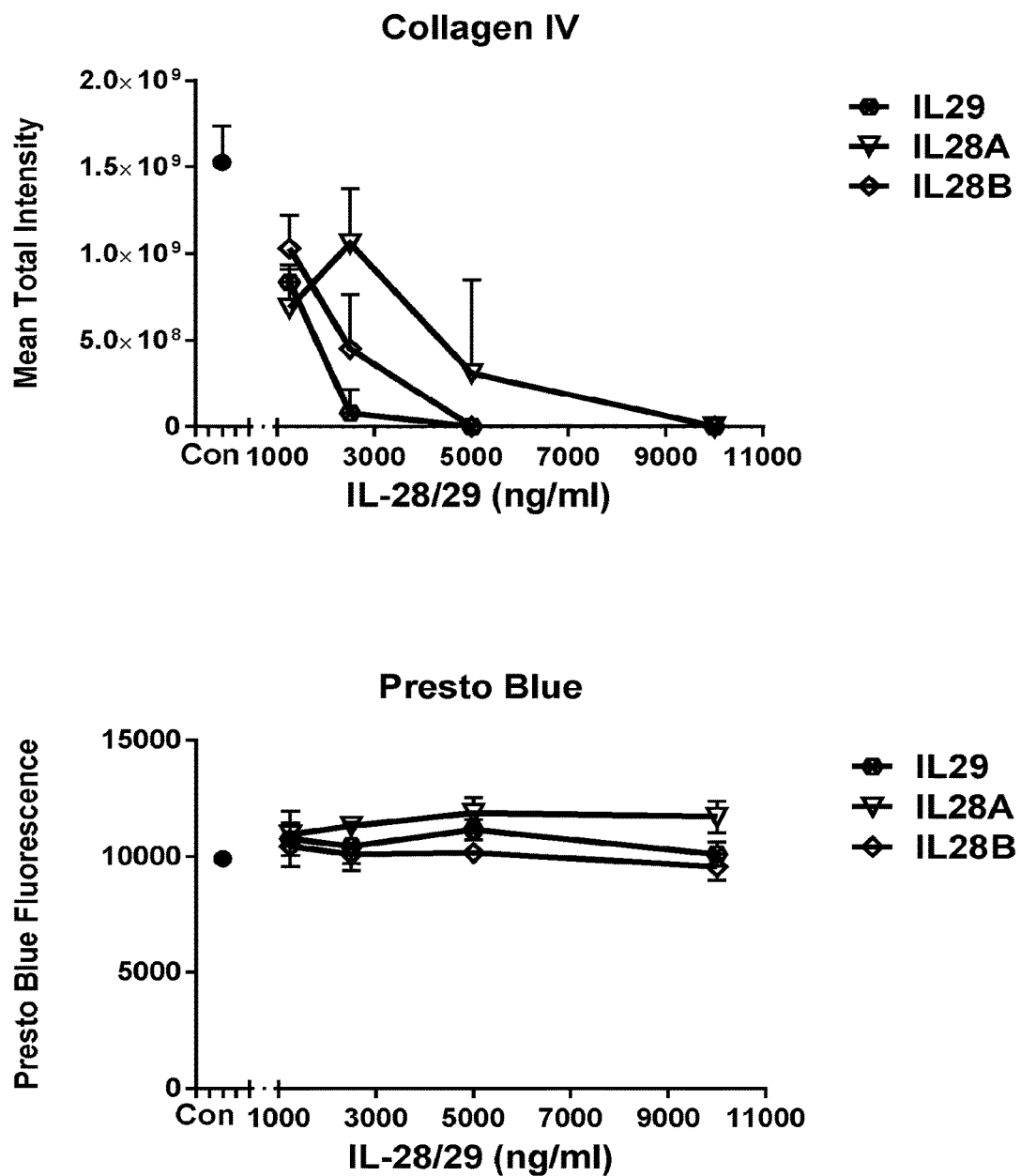
Figure 11 (contd.): Effect of IL-28A, IL-28B and IL-29 in Skin keratinocyte-fibroblast co-culture ECM and cell viability

Figure 12: High content images showing the effect of IL-28A, IL-28B and IL-29 in Skin keratinocyte-fibroblast co-culture ECM
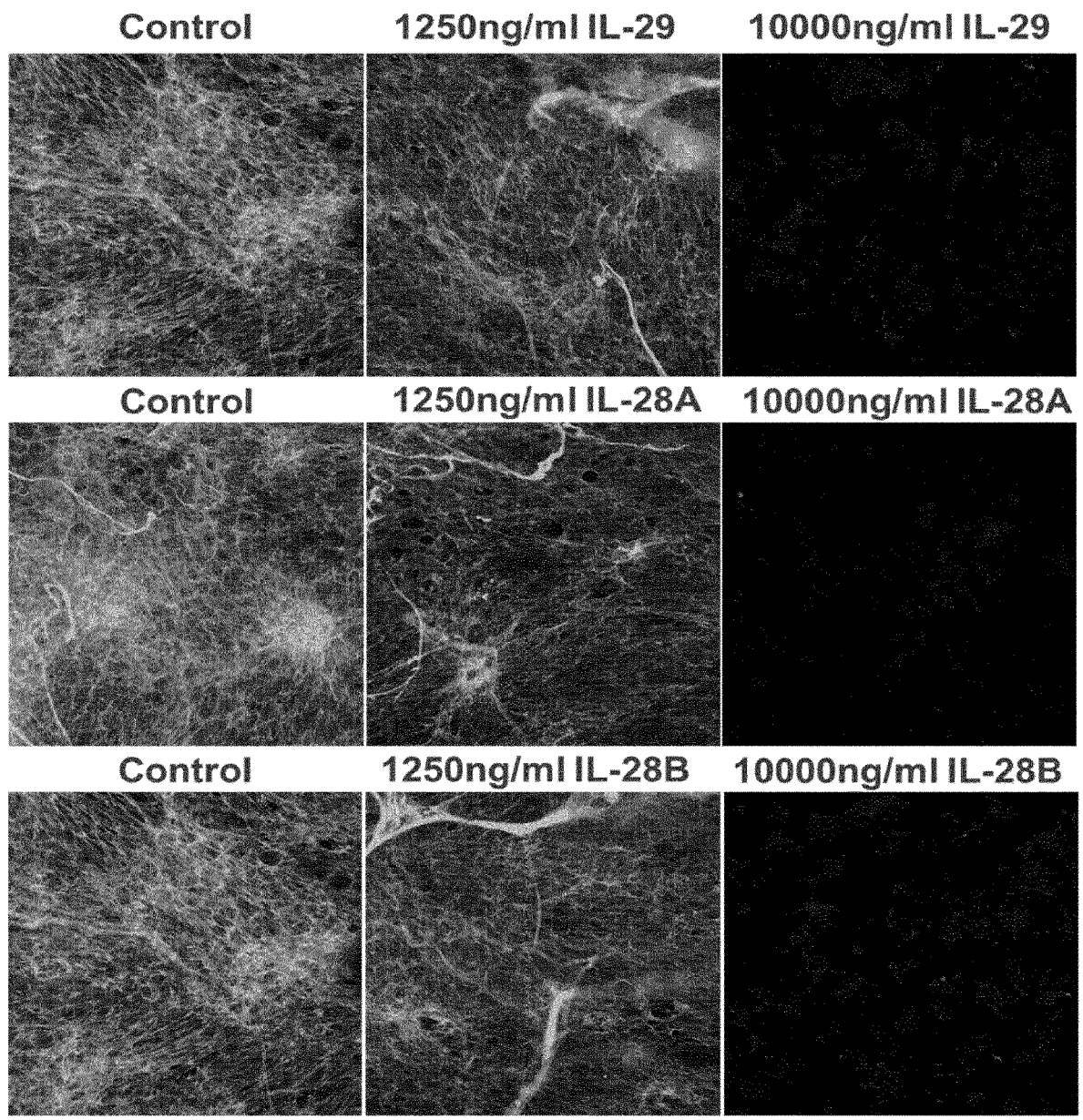

Figure 13: Effect of IL-28A and IL-28B in IL-1α-stimulated skin fibroblast ECM
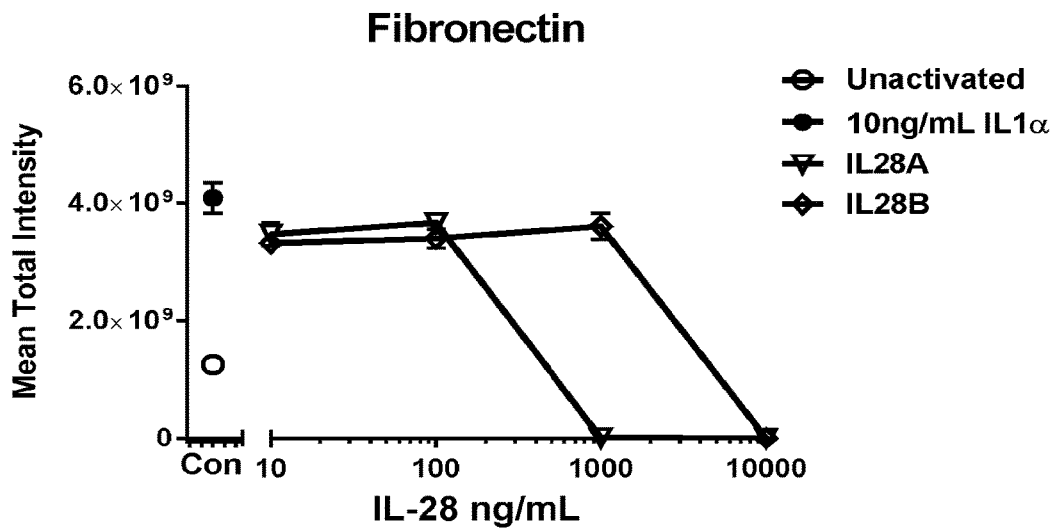
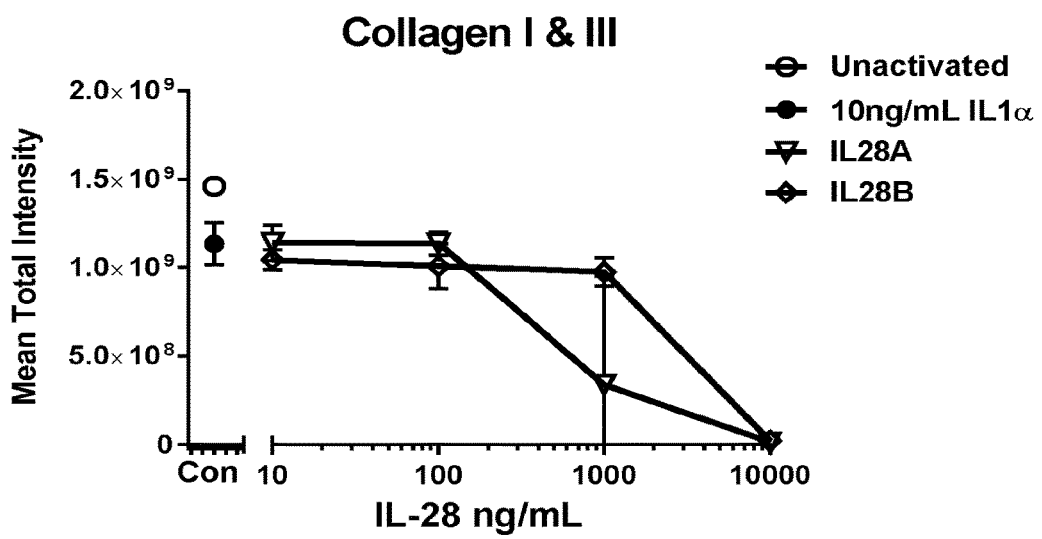

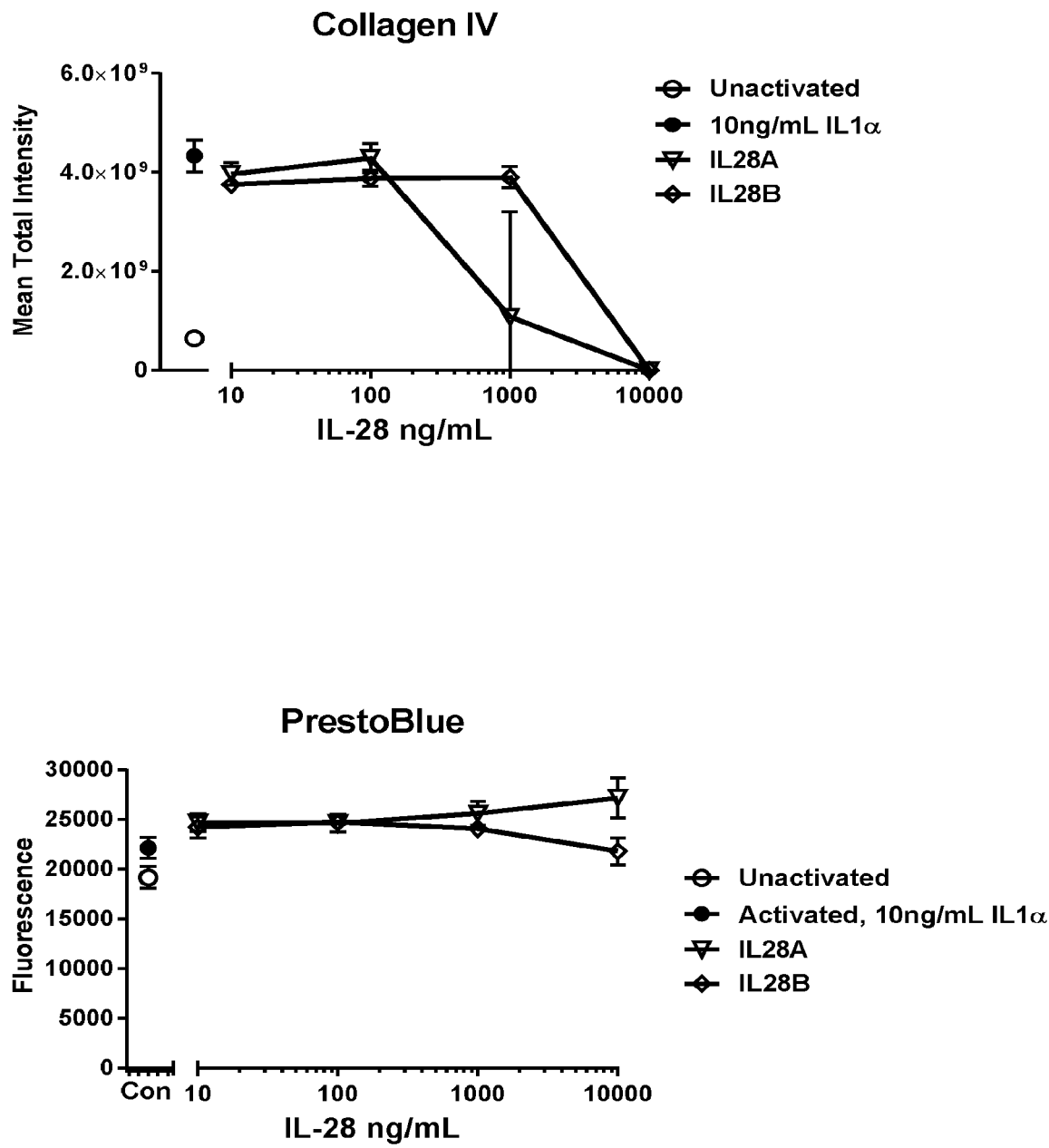
Figure 13 (contd.): Effect of IL-28A and IL-28B in IL-1α-stimulated skin fibroblast ECM and cell viability

Figure 14(a): Effect of IL-28A, IL-28B and IL-29 in Kidney RPTEC-fibroblast co-culture ECM and cell viability – Co-culture addition
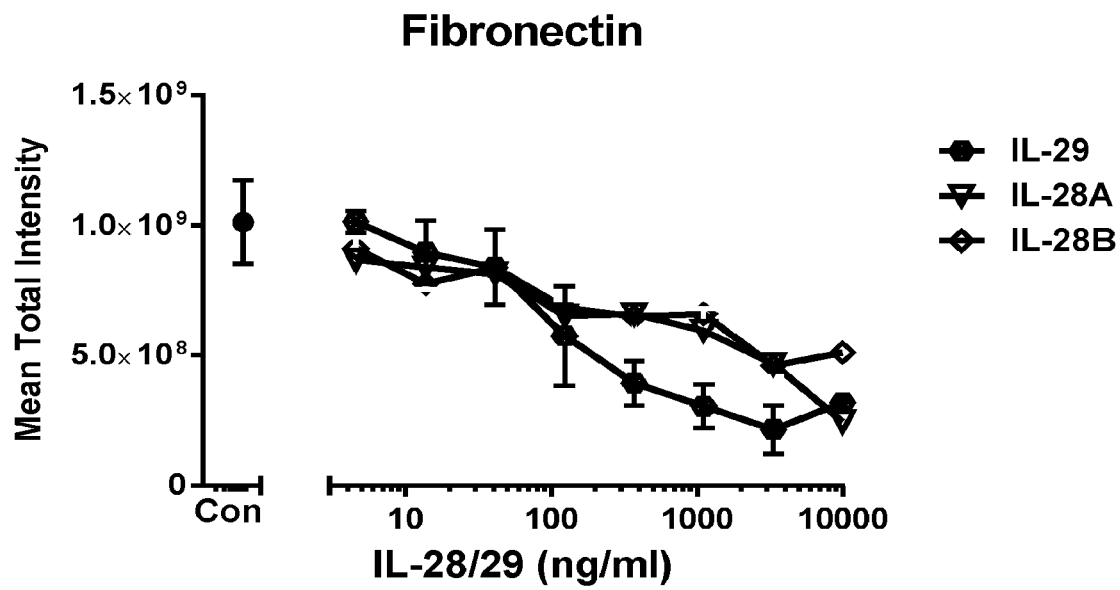
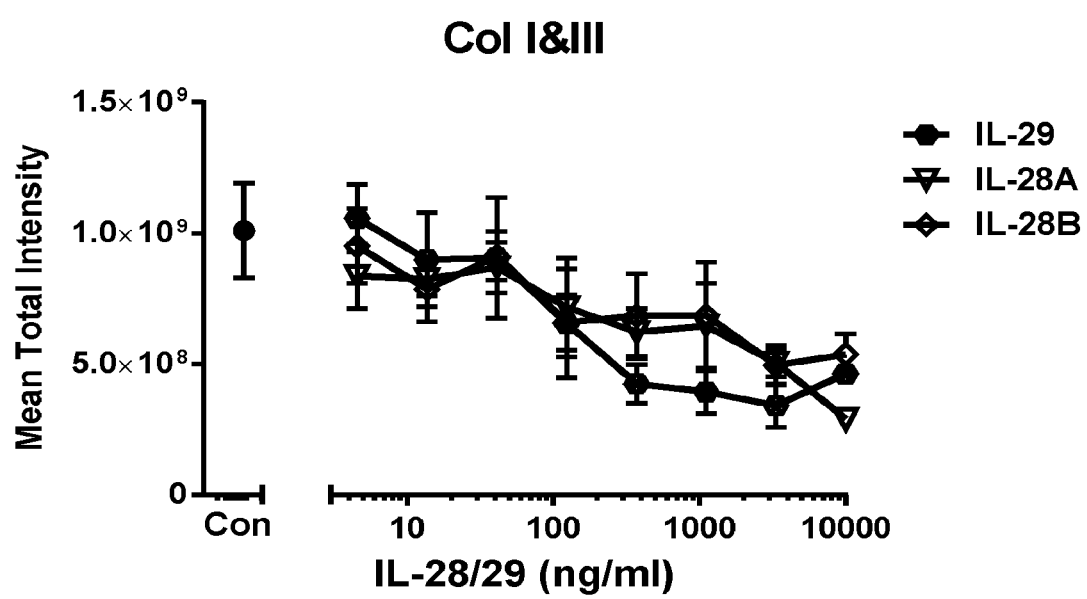

Figure 14(a) (contd.): Effect of IL-28A, IL-28B and IL-29 in Kidney RPTEC-fibroblast co-culture ECM and cell viability – Co-culture addition
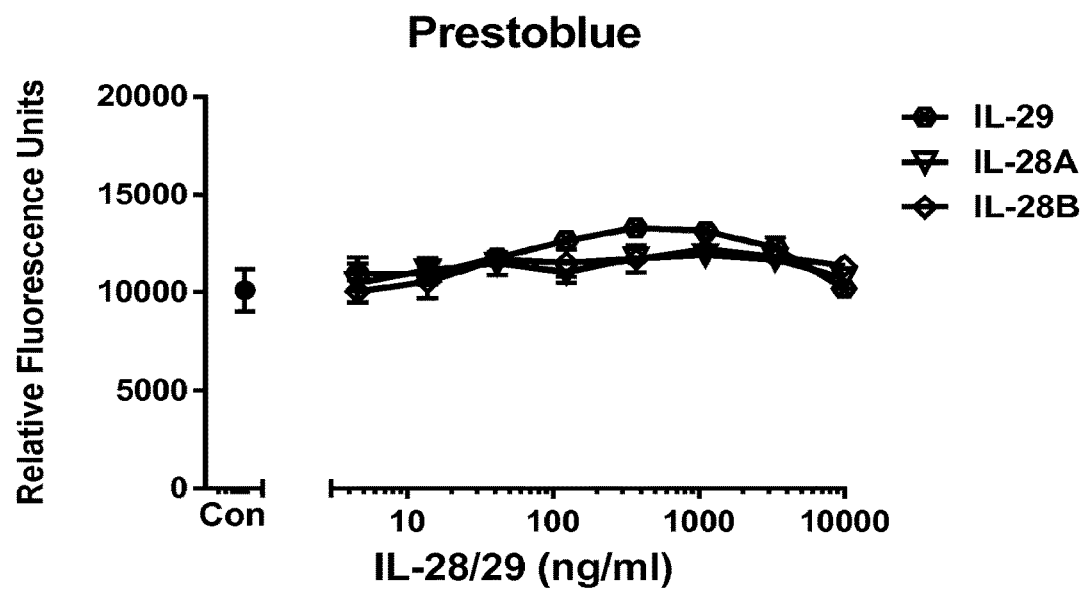

Figure 14(b): Effect of IL-28A, IL-28B and IL-29 in Kidney RPTEC-fibroblast co-culture ECM and cell viability – RPTEC added 1st
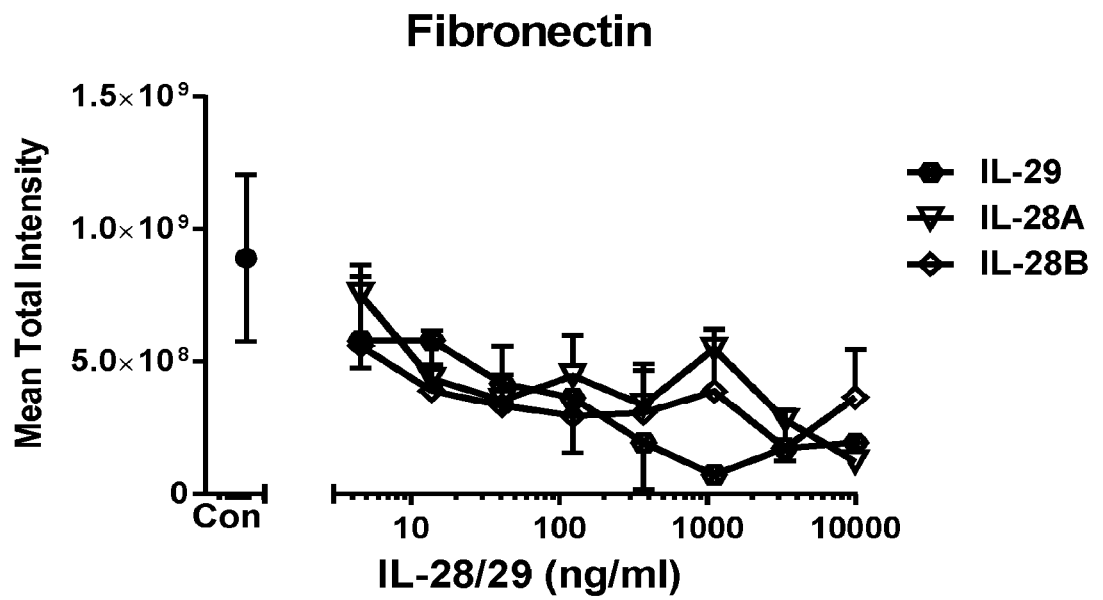
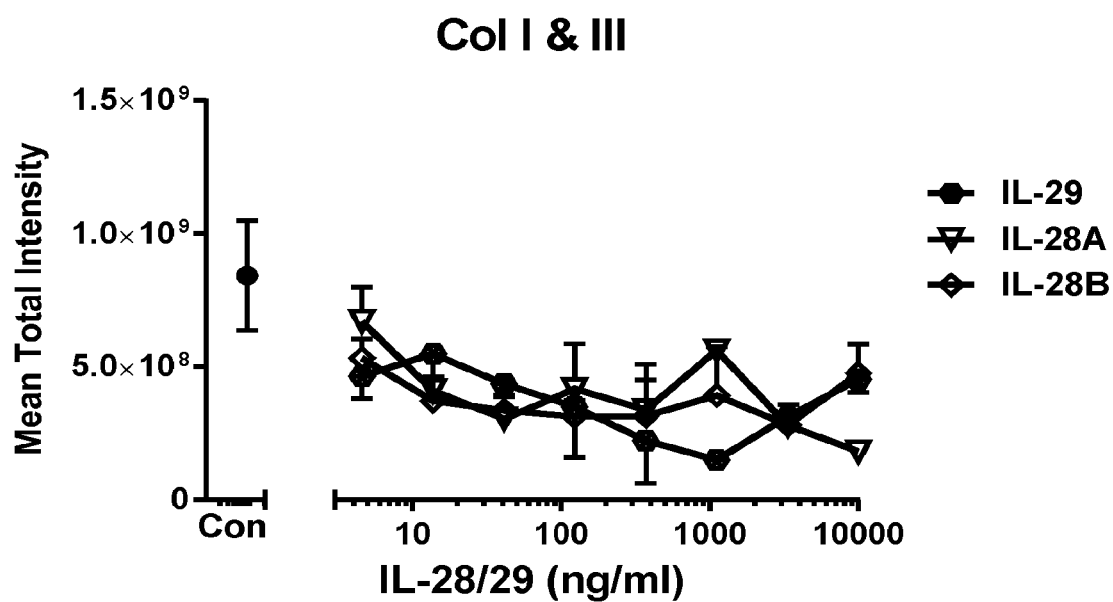

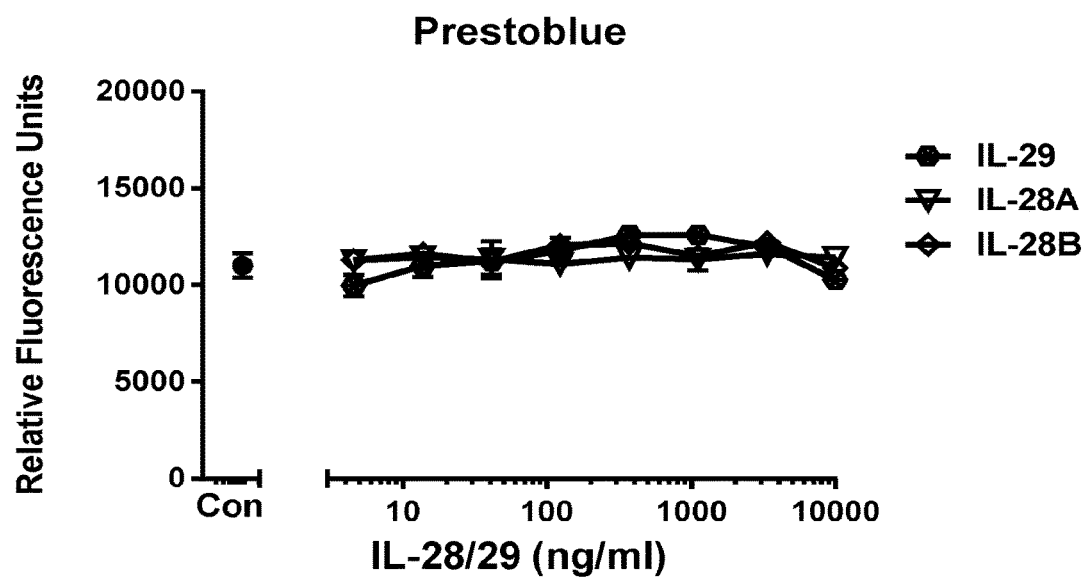
Figure 14(b) (contd.): Effect of IL-28A, IL-28B and IL-29 in Kidney RPTEC-fibroblast co-culture ECM and cell viability – RPTEC added 1st

Figure 14(c): Effect of IL-28A, IL-28B and IL-29 in Kidney RPTEC-fibroblast co-culture ECM and cell viability – HRF added 1st
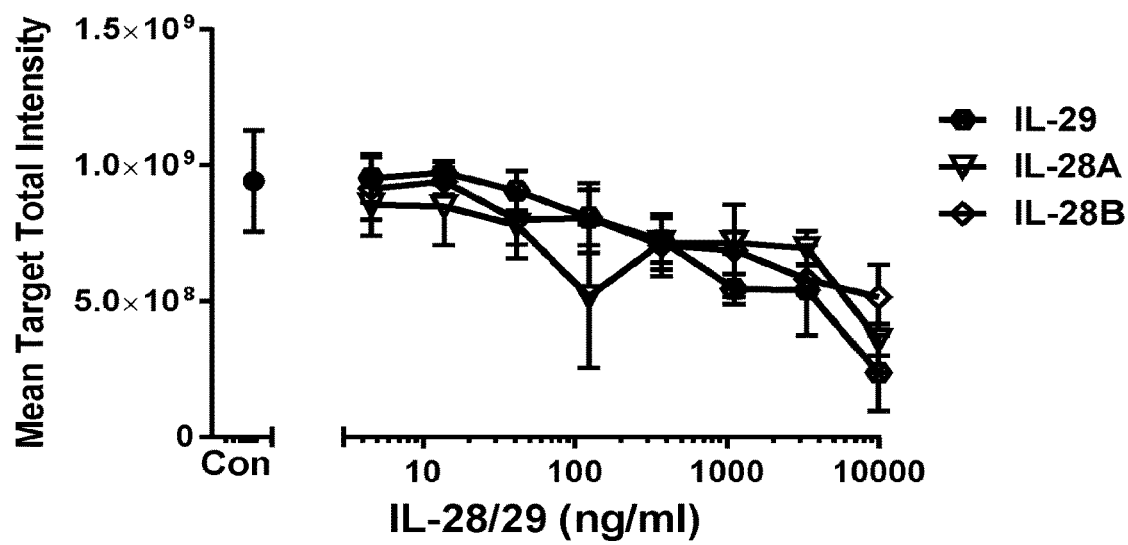
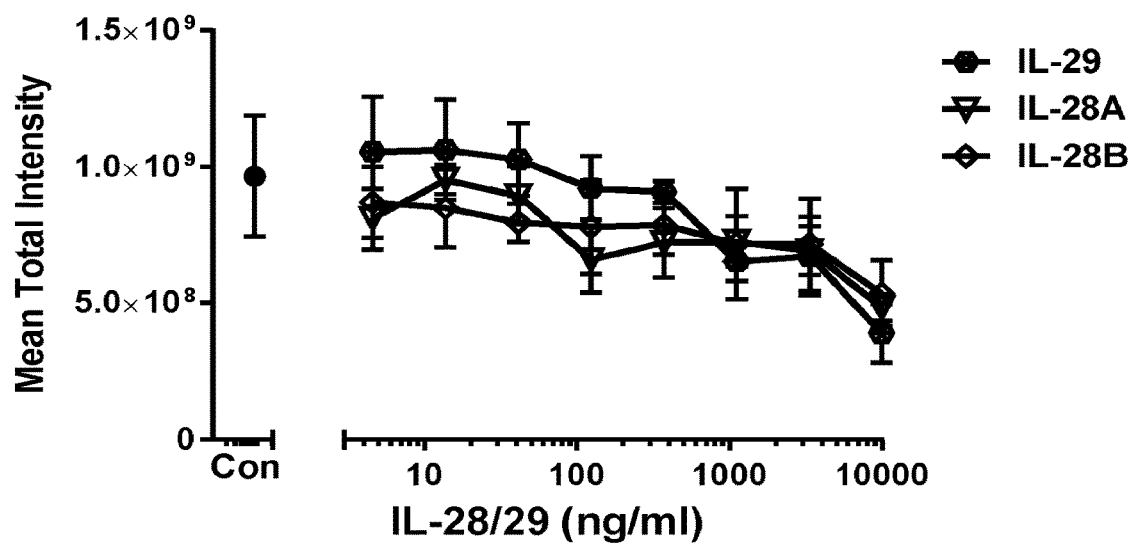

Figure 14(c) (contd.): Effect of IL-28A, IL-28B and IL-29 in Kidney RPTEC-fibroblast co-culture ECM and cell viability – HRF added 1st
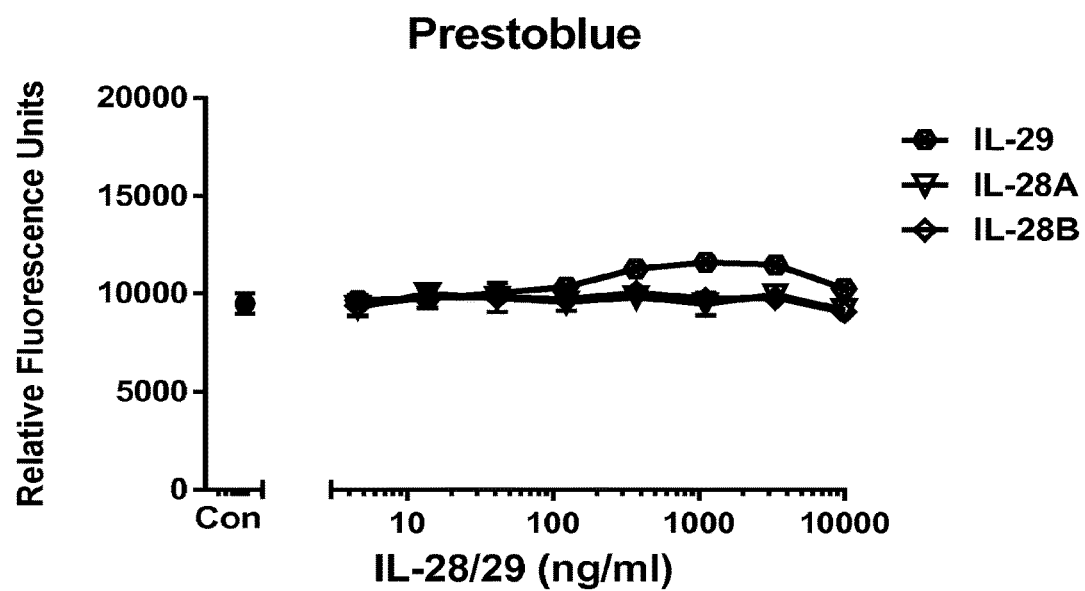

Figure 15(a): Comparison of addition formats on the effect of IL-28A and IL-28B in the Kidney RPTEC-fibroblast co-culture fibronectin
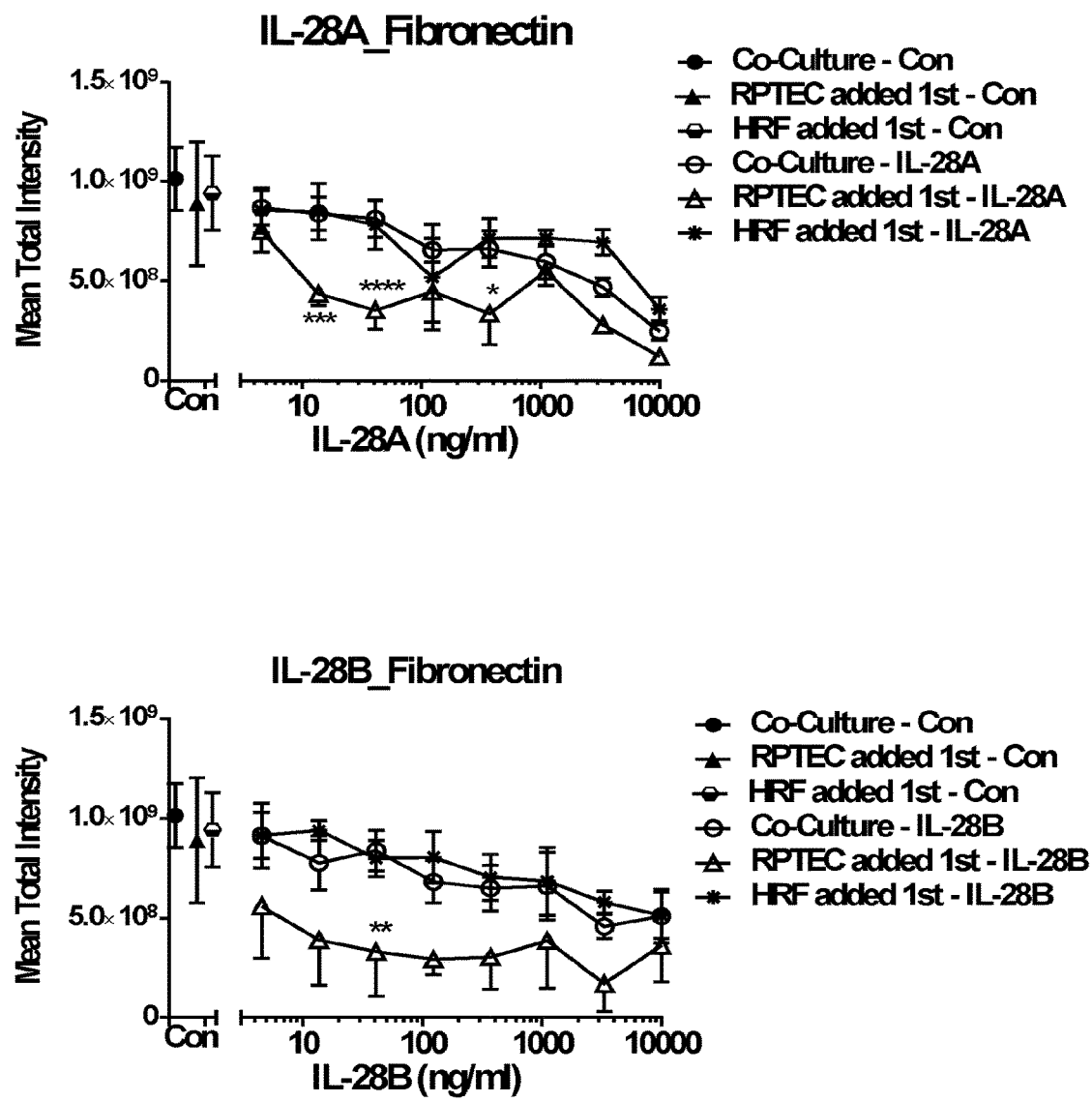

Figure 15(a) (contd): Comparison of addition formats on the effect of IL-29 in the Kidney RPTEC-fibroblast co-culture fibronectin
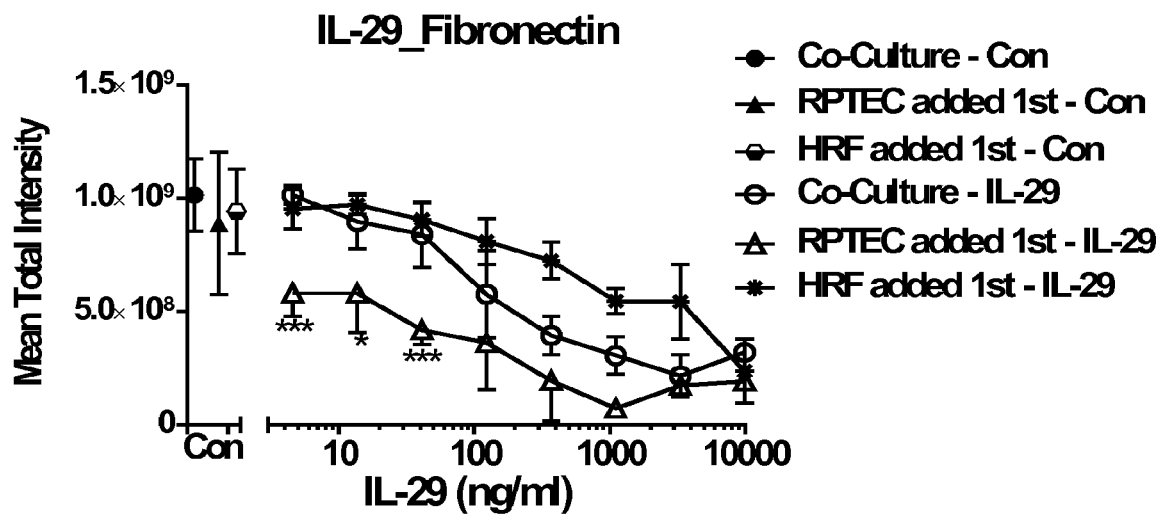

Figure 15(b): Comparison of addition formats on the effect of IL-28A and IL-28B in the Kidney RPTEC-fibroblast co-culture Col I&III
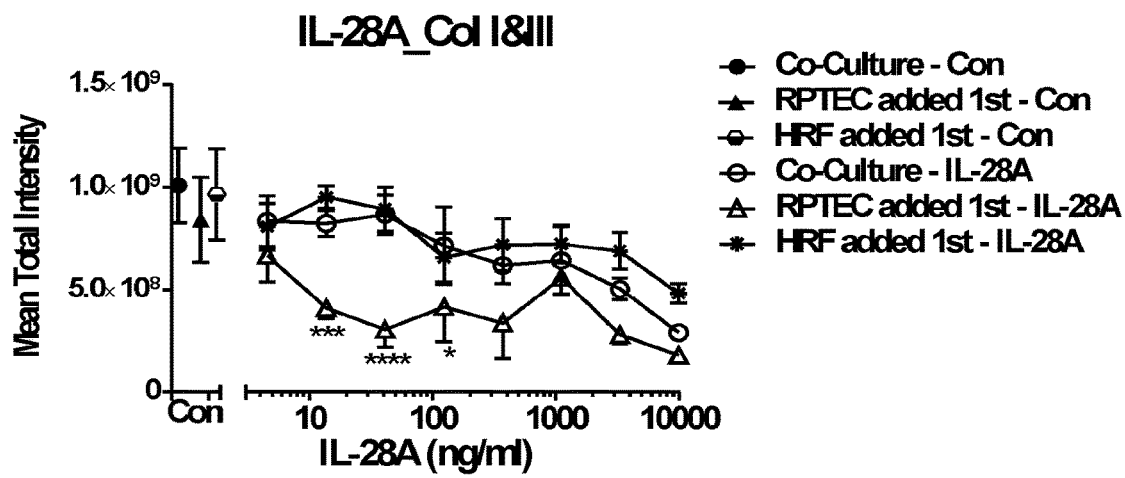
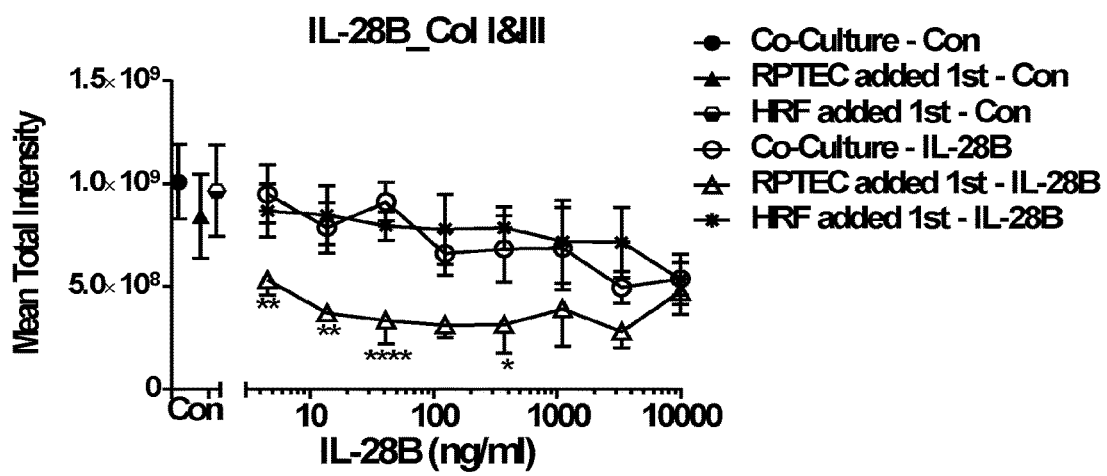

Figure 15(b) (contd): Comparison of addition formats 1 on the effect of IL-29 in the Kidney RPTEC-fibroblast co-culture Col I&III
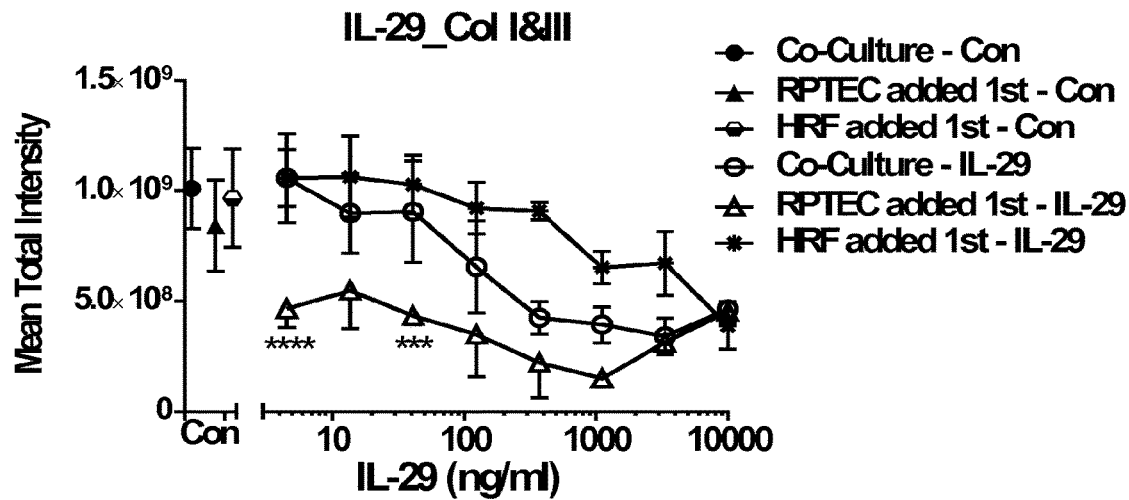

Figure 16: High content images showing the effect of IL-28A, IL-28B and IL-29 in the Kidney RPTEC-fibroblast co-culture ECM
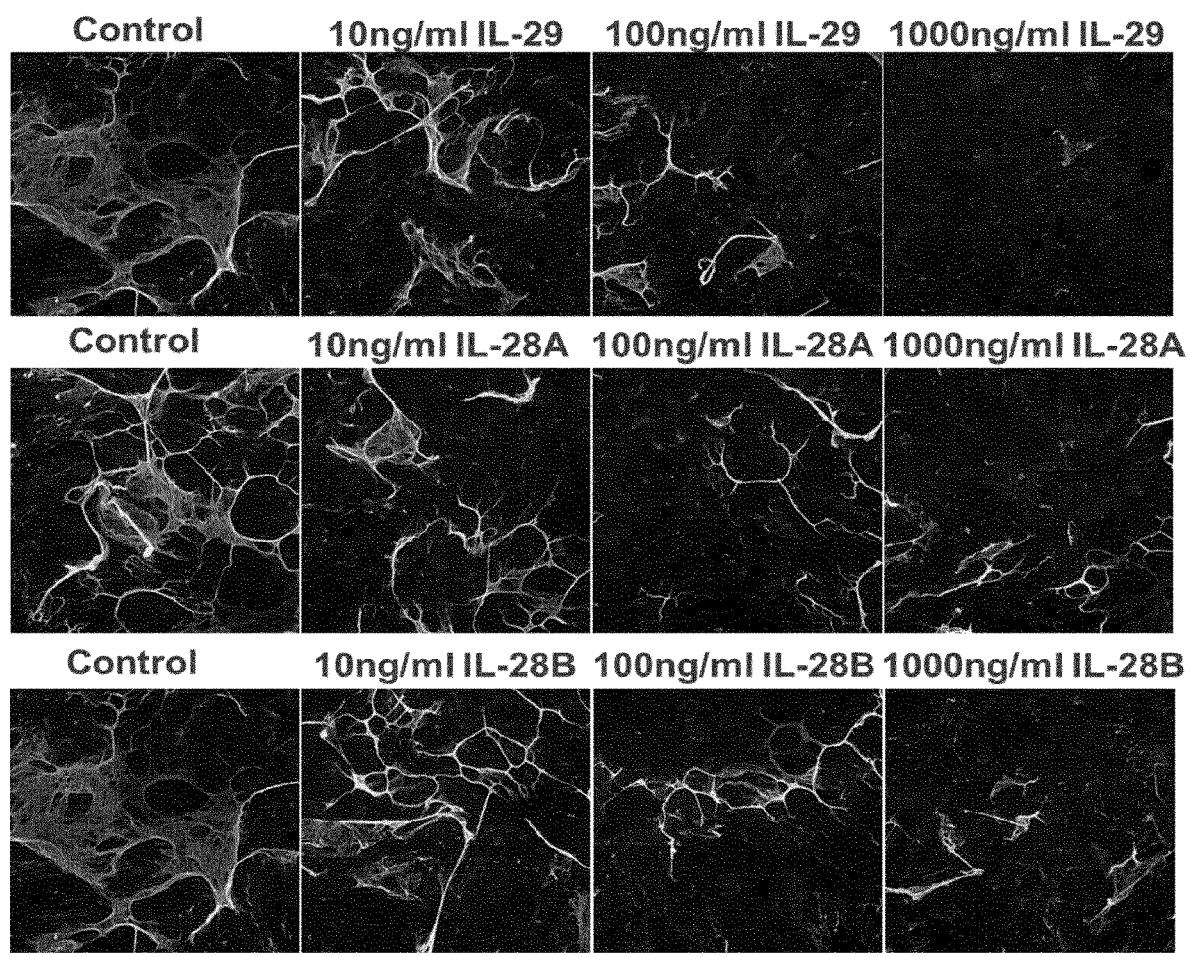

Figure 17: Effect of IL-28A and IL-28B in Lung SAEpithelial-fibroblast co-culture ECM
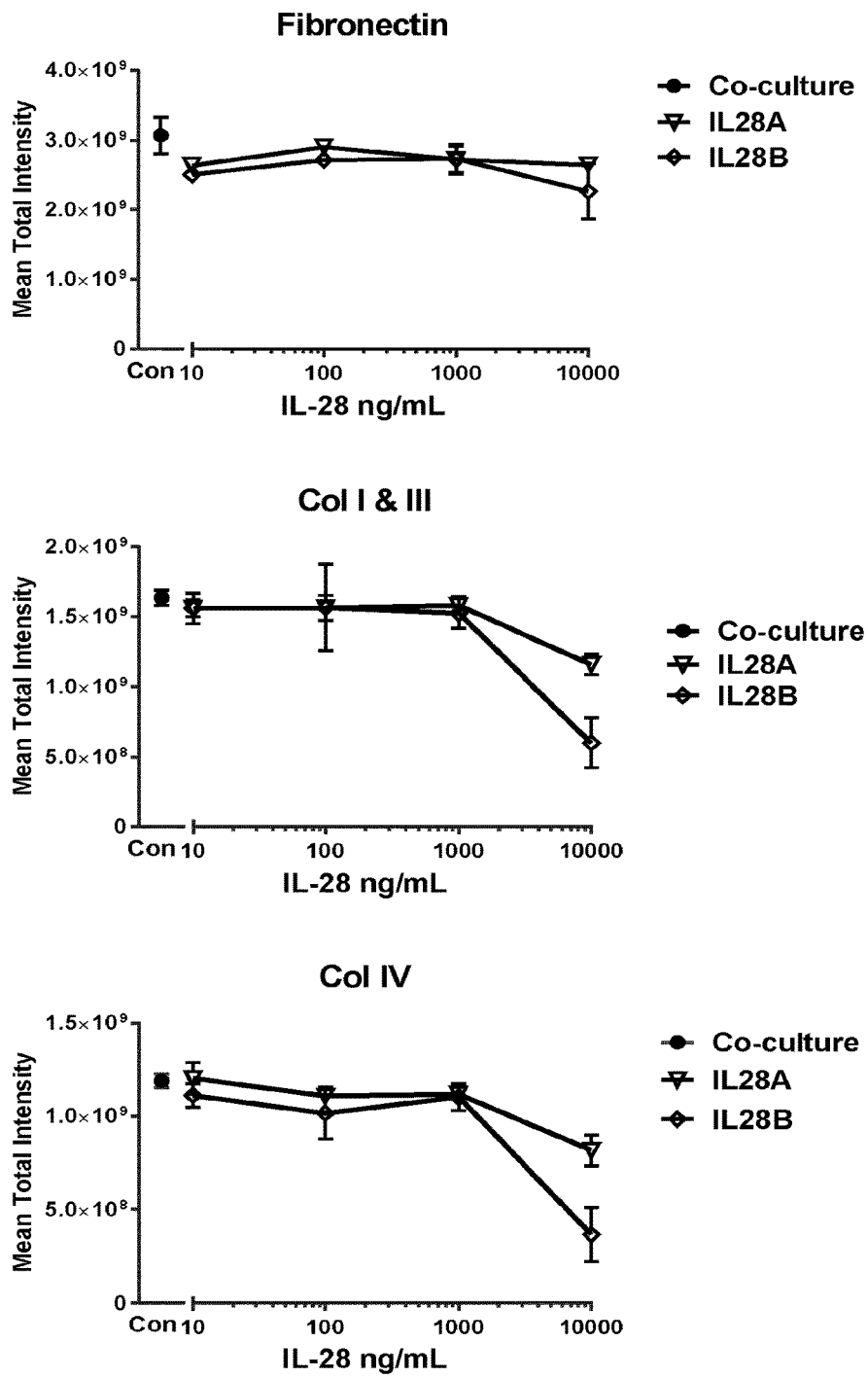

Figure 17 (contd): Effect of IL-28A and IL-28B in Lung SAEpithelial-fibroblast co-culture ECM and cell viability
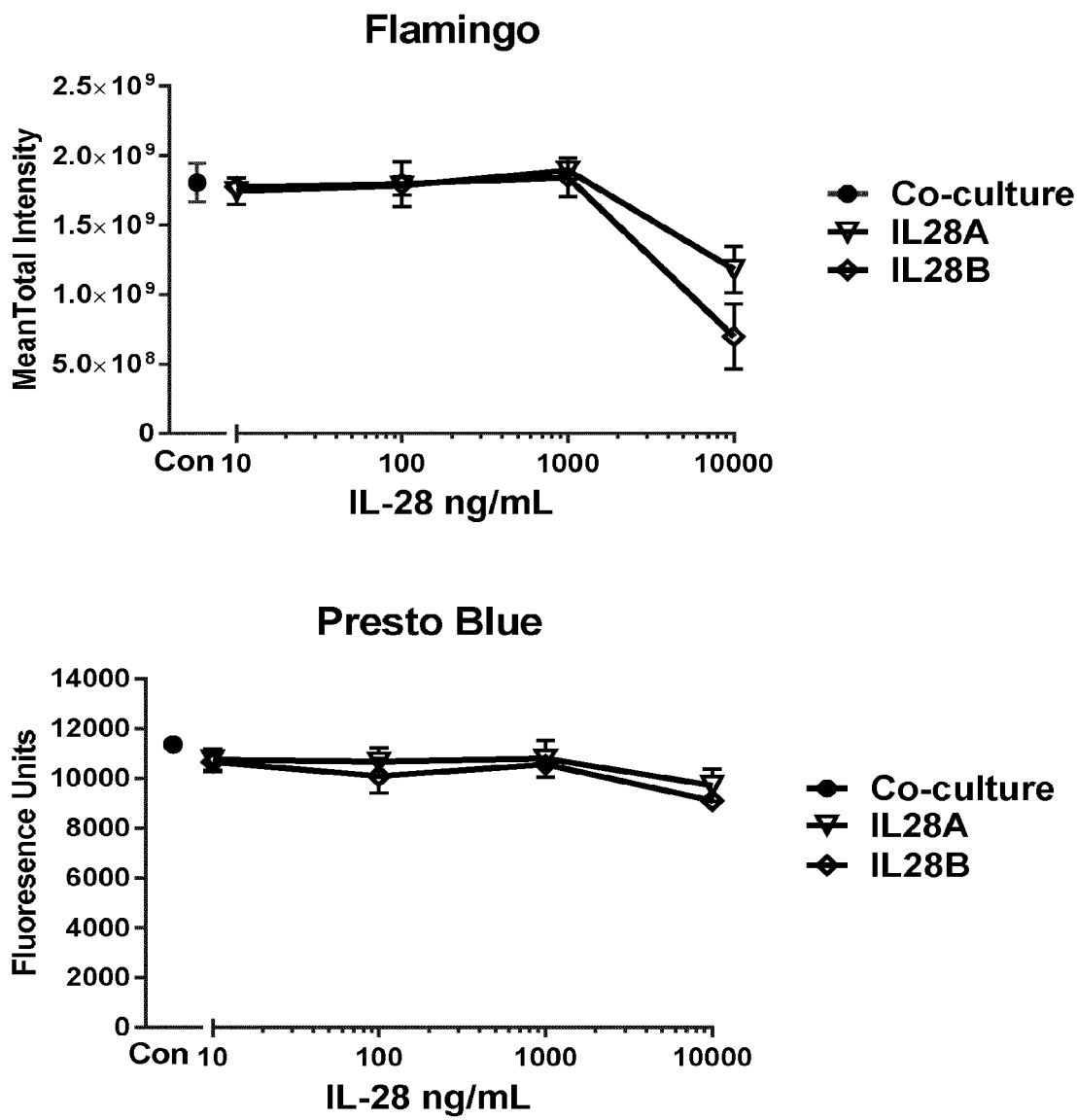

Figure 18: Protein and DNA sequences of IFNL1, IFNL2, IFNL3 and IFNL4

IFNL1 Human Protein sequence (Uniprot IDQ8IU54)
GPVPTSKPTTTGKGCHIGRFKSLSPQELASFKKARDALEESLKLKNWSCSSPVFPGNWDLRLLQVRERPVALEAELALTLKVLE
AAAGPALEDVLDQPLHTLHHILSQLQACIQPQPTAGPRPRGRLHHWLHRLQEAPKKESAGCLEASVTFNLFRLLTRDLKYVAD
GNLCLRTSTHPEST

IFNL1 Human DNA sequence (NM_172140 DNA with introns)
ORIGIN
```
    1 aattaccttt tcactttaca cacatcatct tggattgccc attttgcgtg gctaaaaagc
   61 agagccatgc cgctggggaa gcagttgcga tttagccatg gctgcagctt ggaccgtggt
  121 gctggtgact ttggtgctag gcttggccgt ggcaggccct gtcccactt ccaagcccac
  181 cacaactggg aagggctgcc acattggcag gttcaaatct ctgtcaccac aggagctagc
  241 gagcttcaag aaggccaggg acgccttgga agagtcactc aagctgaaaa actggagttg
  301 cagctctcct gtcttcccg ggaattggga cctgaggctt ctccaggtga gggagcgccc
  361 tgtggccttg gaggctgagc tggccctgac gctgaaggtc ctggaggccg ctgctggccc
  421 agccctggag gacgtcctag accagcccct tcacacctg caccacatcc tctcccagct
  481 ccaggcctgt atccagcctc agcccacagc agggcccagg ccccggggcc gcctccacca
  541 ctggctgcac cggctccagg aggcccccaa aaaggagtcc gctggctgcc tggaggcatc
  601 tgtcaccttc aacctcttcc gcctcctcac gcgagacctc aaatatgtgg ccgatgggaa
  661 cctgtgtctg agaacgtcaa cccaccctga gtccacctga caccacac cttatttatg
  721 cgctgagccc tactccttcc ttaatttatt tcctctcacc ctttatttat gaagctgcag
  781 ccctgactga gacataggc tgagtttatt gttttacttt tatacattat gcacaaataa
  841 acaacaagga attgga
```

IFNL2 Human Protein sequence (Uniprot ID Q8IZJ0)
VPVARLHGALPDARGCHIAQFKSLSPQELQAFKRAKDALEESLLLKDCRCHSRLFPRTWDLRQLQVRERPMALEAELALTLKV
LEATADTDPALVDVLDQPLHTLHHILSQFRACIQPQPTAGPRTRGRLHHWLYRLQEAPKKESPGCLEASVTFNLFRLLTRDLNC
VASGDLCV

IFNL2 Human DNA sequence (NM_172138 DNA with introns)
ORIGIN
```
    1 tgggtgacag cctcagagtg ttcttctgc tgacaaagac cagagatcag gaatgaaact
   61 agacatgact ggggactgca cgccagtgct ggtgctgatg gccgcagtgc tgaccgtgac
  121 tggagcagtt cctgtcgcca ggctccacgg ggctctccg gatgcaaggg gctgccacat
  181 agcccagttc aagtccctgt ctccacagga gctgcaggcc tttaagaggg ccaaagatgc
  241 cttagaagag tcgcttctgc tgaaggactg caggtgccac tcccgcctct tcccaggac
  301 ctgggacctg aggcagctgc aggtgaggga gcgcccatg gctttggagg ctgagctggc
  361 cctgacgctg aaggttctgg aggccaccgc tgacactgac cagccctgg tggacgtctt
  421 ggaccagccc cttcacaccc tgcaccatat cctctcccag ttcgggcct gtatccagcc
  481 tcagcccacg gcagggccca ggacccgggg ccgcctccac cattggctgt accggctcca
  541 ggaggcccca aaaaggagt ccctggctg cctcgaggcc tctgtcacct caacctctt
  601 ccgcctcctc acgcgagacc tgaattgtgt tgccagtggg gacctgtgtg tctgaccctc
  661 ccaccagtca tgcaacctga gattttattt ataaattagc cacttgtctt aatttattgc
  721 cacccagtcg ctat
```

Figure 18 (contd.): Protein and DNA sequences of IFNL1, IFNL2, IFNL3 and IFNL4

IFNL3 Human Protein sequence (Uniprot ID Q8IZ19 )

VPVARLRGALPDARGCHIAQFKSLSPQELQAFKRAKDALEESLLLKDCKCRSRLFPRTWDLRQLQ
VRERPVALEAELALTLKVLEATADTDPALGDVLDQPLHTLHHILSQLRACIQPQPTAGPRTRGRLH
HWLHRLQEAPKKESPGCLEASVTFNLFRLLTRDLNCVASGDLCV

IFNL3 Human DNA sequence (NM_172139 DNA with introns)

```
ORIGIN
        1 ctgcattccc tcagctccct ttctctctgt gacacagaca tgaccgggga ctgcatgcca
       61 gtgctggtgc tgatggccgc agtgctgacc gtgactggag cagttcctgt cgccaggctc
      121 cgcgggctc tcccggatgc aaggggctgc cacatagccc agttcaagtc cctgtctcca
      181 caggagctgc aggcctttaa gagggccaaa gatgccttag aagagtcgct tctgctgaag
      241 gactgcaagt gccgctcccg cctcttcccc aggacctggg acctgaggca gctgcaggtg
      301 agggagcgcc ccgtggcttt ggaggctgag ctggccctga cgctgaaggt tctggaggcc
      361 accgctgaca ctgacccagc cctggggat gtcttggacc agccccttca cacctgcac
      421 catatcctct cccagctccg ggcctgtatc cagcctcagc caacggcagg gccaggacc
      481 cggggccgcc tccaccattg gctgcaccgg ctccaggagg cccaaaaaaa ggagtccct
      541 ggctgcctcg aggcctctgt caccttcaac ctcttccgcc tcctcacgcg agacctgaat
      601 tgtgttgcca gcggggacct gtgtgtctga cccttccgcc agtcatgcaa cctgag
```

IFNL4 Human Protein sequence (Uniprot ID K9M1U5 )

AAPRRCLLSHYRSLEPRTLAAAKALRDRYEEEALSWGQRNCSFRPRRDPPRPSSCARLRHVARG
IADAQAVLSGLHRSELLPGAGPILELLAAAGRDVAACLELARPGSSRKVPGAQKRRHKPRRADSP
RCRKASVVFNLLRLLTWELRLAAHSGPCL

IFNL4 Human mRNA sequence (AFQ38559)

```
ATGCGGCCGAGTGTCTGGGCCGCAGTGGCCGCGGGCTGTGGGTCCTGTGCACGGTGATC
GCAGCGGCCCCCGGCGCTGCCTGCTCTCGCACTACCGCTCGCTGGAGCCCCGGACGCTG
GCGGCTGCCAAGGCGCTGAGGGACCGCTACGAGGAAGAGGCGCTGAGCTGGGGGCAGCGC
AACTGCTCCTTCCGCCCCAGGAGGGATCCTCCGCGGCCATCGTCCTGCGCTCGGCTCCGC
CACGTGGCCCGGGGCATCGCGGACGCCCAGGCAGTGCTCAGCGGCCTGCACCGCTCGGAG
CTGCTCCCCGGCGCCGGCCCGATCCTGGAGCTGCTGGCGGCCGCGGGGAGGGATGTGGCG
GCCTGCCTTGAGCTGGCACGGCCAGGCTCCTCCAGGAAGGTCCCCGGGGCCCAGAAGAGG
CGTCACAAACCCCGGAGAGCGGACTCGCCTCGGTGCCGCAAAGCCAGCGTGGTCTTCAAC
CTCCTGCGCCTGCTCACGTGGGAGCTCCGGCTGGCTGCACACTCTGGGCCTTGCCTCTGA
```

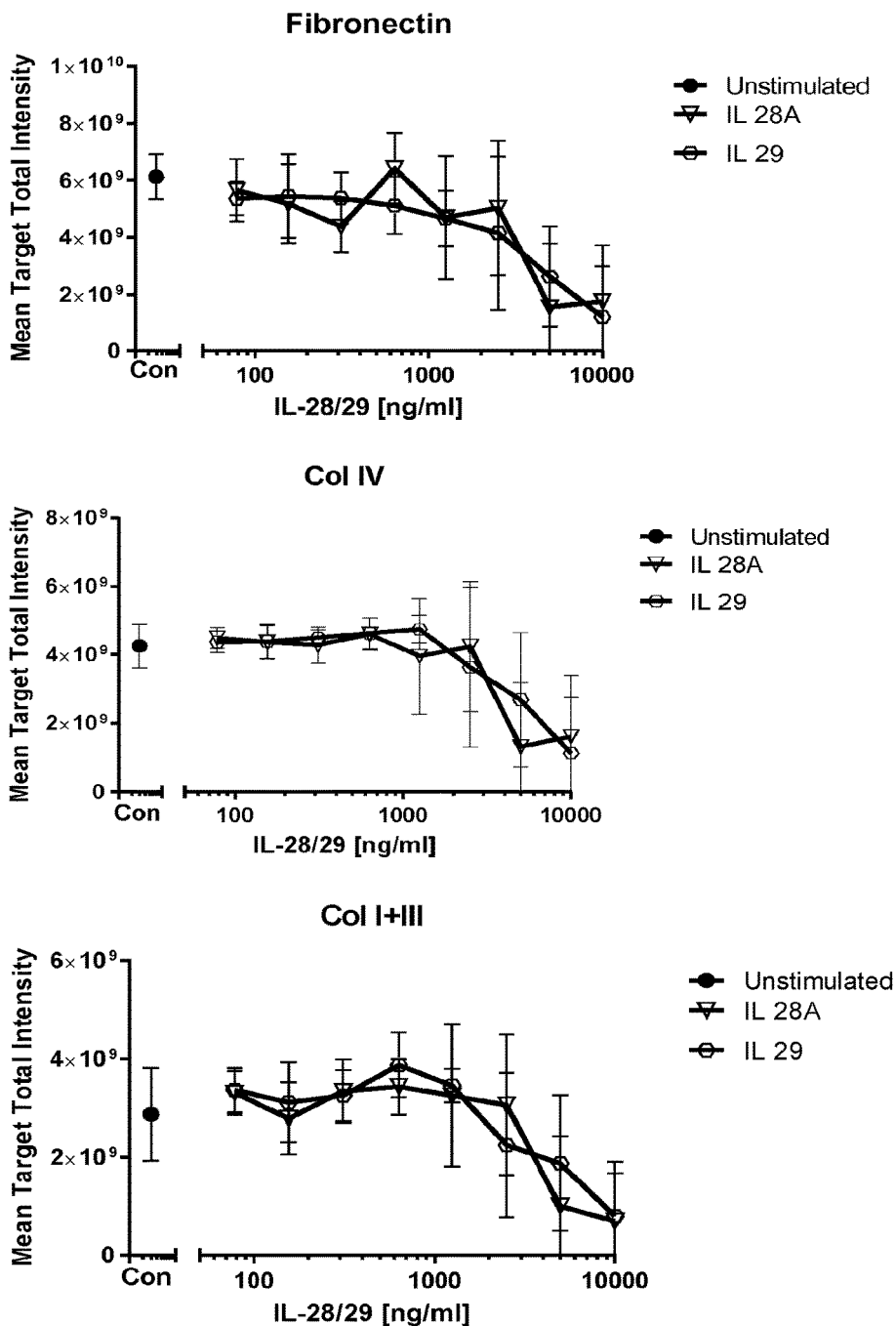
Figure 19: Effect of IL-28A and IL-29 in an in vitro Human Liver stellate and epithelial cell co-culture model of hepatic fibrosis

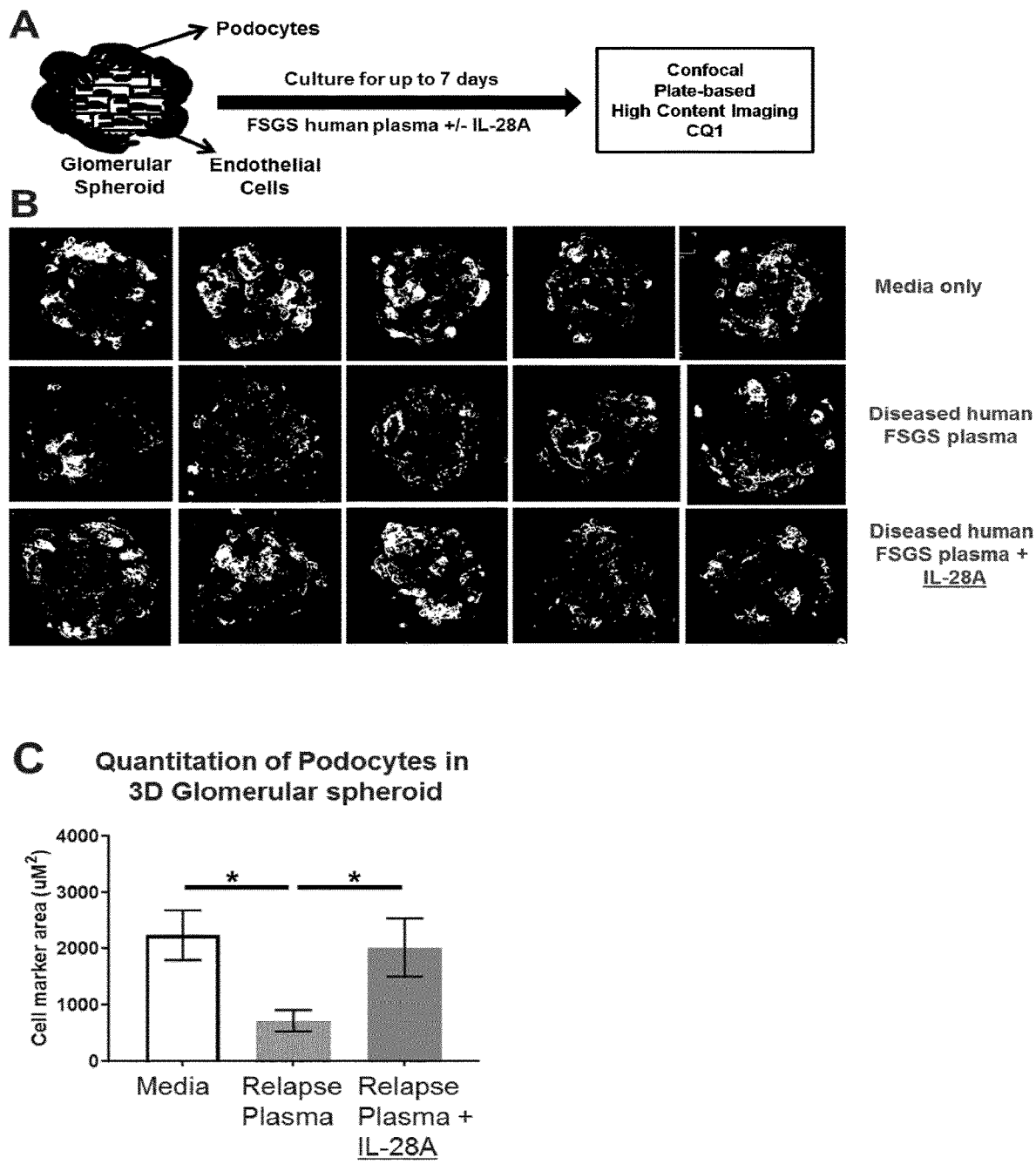
Figure 20: Effect of IL-28A on podocyte survival in an in vitro 3D Glomerular spheroid model of Glomeruolosclerosis

Figure 21: Hydrodynamic Transfection of mouse IL-28B protects against fibrosis in the mouse unilateral ureteral obstruction (UUO) kidney fibrosis model
A  PSR Staining of mouse fibrotic kidneys from IL28B-treated mice
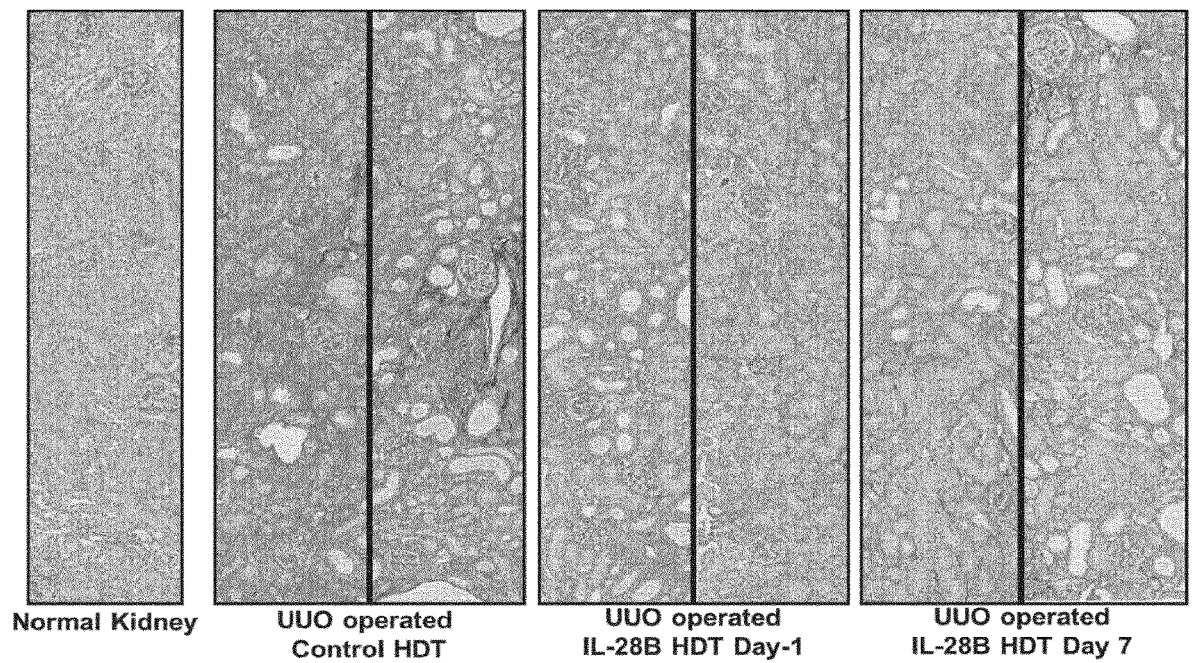
Normal Kidney | UUO operated Control HDT | UUO operated IL-28B HDT Day-1 | UUO operated IL-28B HDT Day 7

Figure 21: Hydrodynamic transfection of Mouse IL-28B into Mouse unilateral ureteral obstruction model of kidney fibrosis reduces interstitial collagen
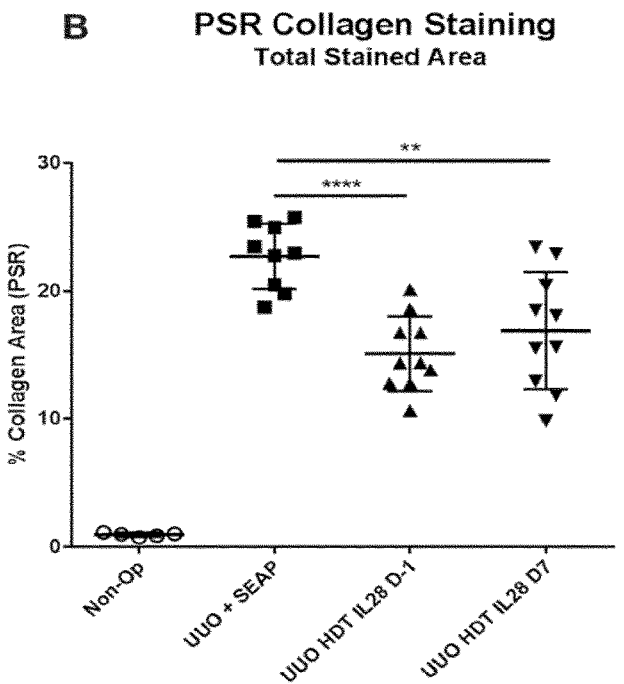
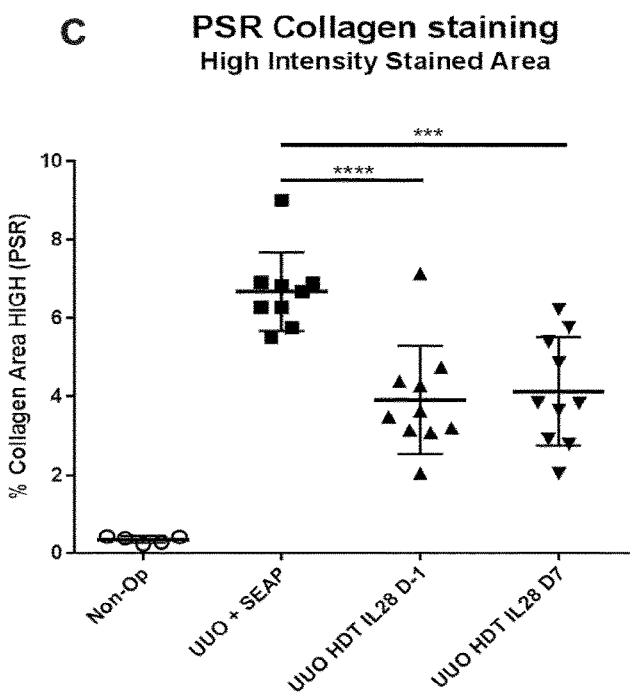

Figure 22: Effect of IL-29 in an in vitro Human Kidney renal proximal tubular epithelial cell mono-culture model of kidney fibrosis
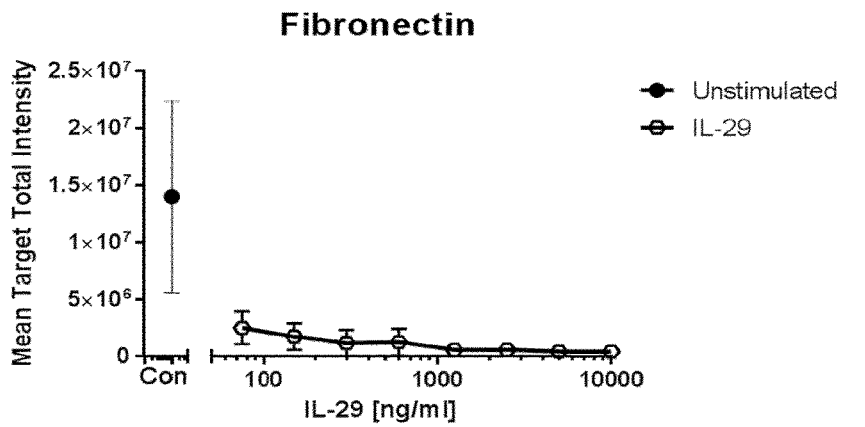
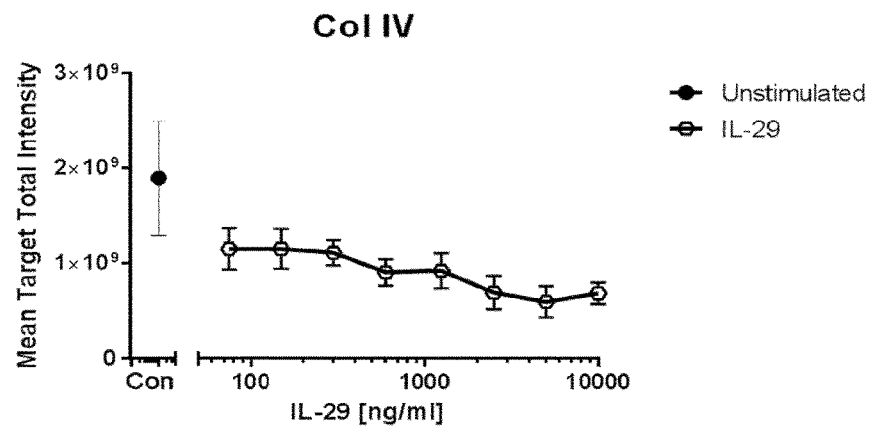
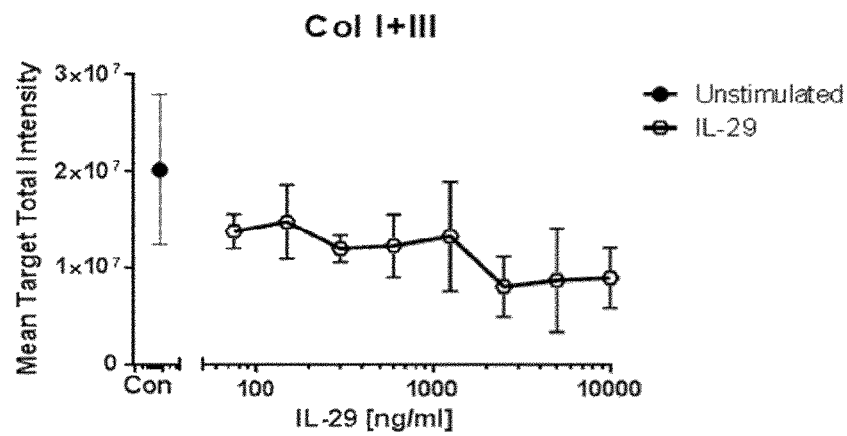

Figure 23(a): Hydrodynamic Transfection of human IL-29 protects against fibrosis in the mouse unilateral ureteral obstruction model (UUO) of kidney fibrosis
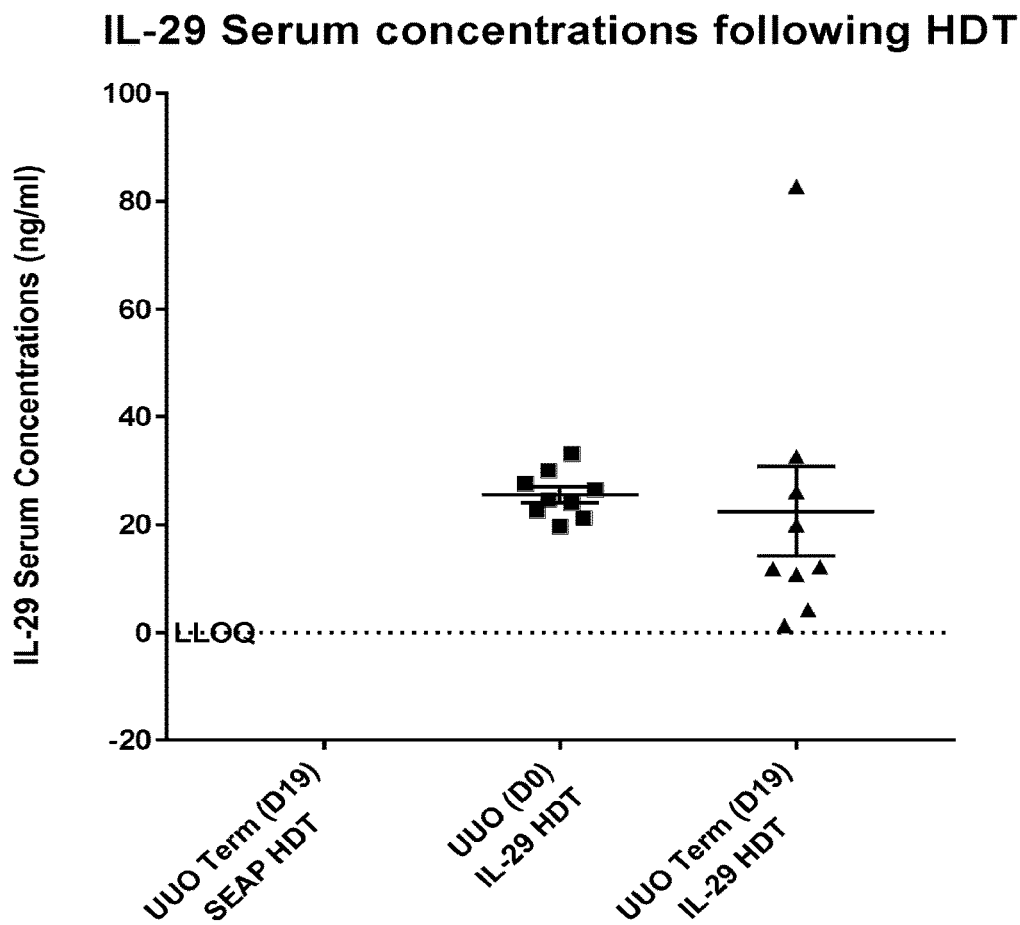

Figure 23(b): Hydrodynamic Transfection of human IL-29 protects against fibrosis in the mouse unilateral ureteral obstruction model (UUO) of kidney fibrosis
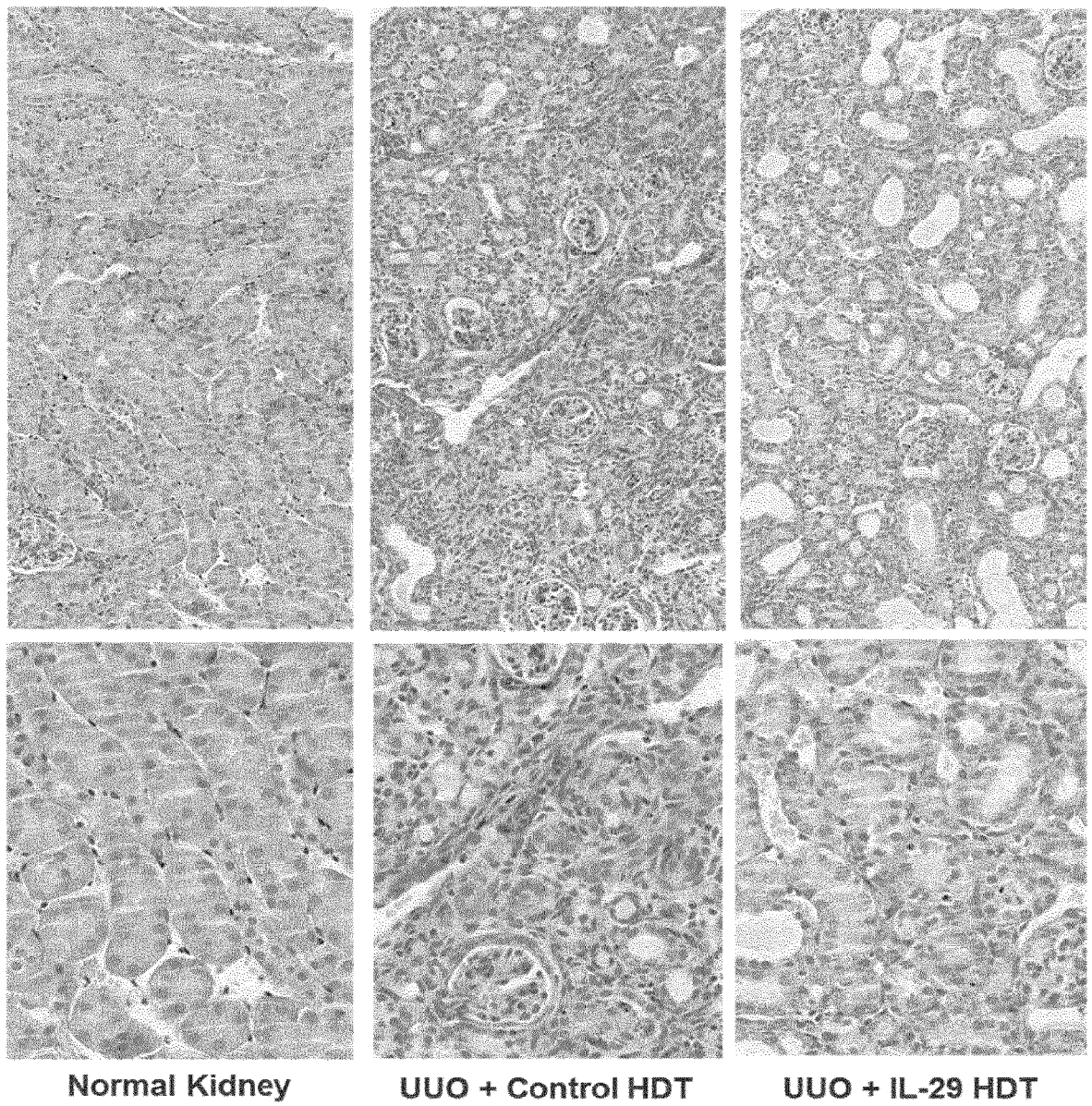
PSR Staining of mouse fibrotic kidneys from IL-29-treated mice
Normal Kidney   UUO + Control HDT   UUO + IL-29 HDT

Figure 23(c): Hydrodynamic Transfection of human IL-29 protects against fibrosis in the mouse unilateral ureteral obstruction model (UUO) of kidney fibrosis
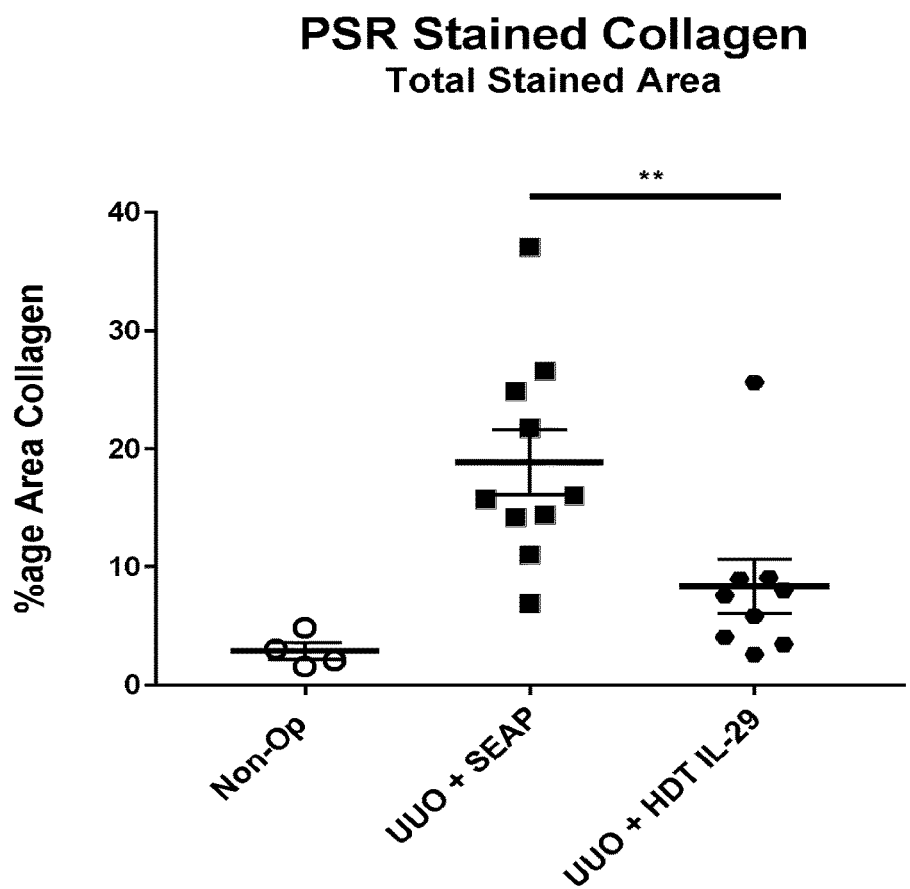

SEQUENCE LISTING

```
Sequence total quantity: 8
SEQ ID NO: 1            moltype = AA  length = 181
FEATURE                 Location/Qualifiers
source                  1..181
                        mol_type = protein
                        organism = Homo sapiens
SEQUENCE: 1
GPVPTSKPTT TGKGCHIGRF KSLSPQELAS FKKARDALEE SLKLKNWSCS SPVFPGNWDL   60
RLLQVRERPV ALEAELALTL KVLEAAAGPA LEDVLDQPLH TLHHILSQLQ ACIQPQPTAG   120
PRPRGRLHHW LHRLQEAPKK ESAGCLEASV TFNLFRLLTR DLKYVADGNL CLRTSTHPES   180
T                                                                  181

SEQ ID NO: 2            moltype = DNA  length = 856
FEATURE                 Location/Qualifiers
source                  1..856
                        mol_type = unassigned DNA
                        organism = Homo sapiens
SEQUENCE: 2
aattacccttt tcactttaca cacatcatct tggattgccc attttgcgtg gctaaaaagc   60
agagccatgc cgctggggaa gcagttgcga tttagccatg gctgcagctt ggaccgtggt   120
gctggtgact ttggtgctag gcttggccgt ggcaggccct gtccccactt ccaagcccac   180
cacaactggg aagggctgcc acattggcag gttcaaatct ctgtcaccac aggagctagc   240
gagcttcaag aaggccaggg acgccttgga agagtcactc aagctgaaaa actggagttg   300
cagctctcct gtcttccccg ggaattggga cctgaggctt ctccaggtga gggagcgccc   360
tgtggccttg gaggctgagc tggccctgac gctgaaggtc ctggaggccg ctgctggccc   420
agccctggag gacgtcctag accagcccct tcacaccctg caccacatcc tctcccagct   480
ccaggcctgt atccagcctc agcccacagc agggcccagg ccccgggggc gcctccacca   540
ctgctgcac cggctccagg aggcccccaa aaaggagtcc gctggctgcc tggaggcatc   600
tgtcaccttc aacctcttcc gcctcctcac gcgagaccta aaatatgtgg ccgatgggaa   660
cctgtgtctg agaacgtcaa cccaccctga gtccacctga caccccacac cttatttatg   720
cgctgagccc tactccttcc ttaatttatt tcctctcacc ctttatttat gaagctgcag   780
ccctgactga gacatagggc tgagtttatt gttttacttt tatacattat gcacaaataa   840
acaacaagga attgga                                                  856

SEQ ID NO: 3            moltype = AA  length = 175
```

```
FEATURE                 Location/Qualifiers
source                  1..175
                        mol_type = protein
                        organism = Homo sapiens
SEQUENCE: 3
VPVARLHGAL PDARGCHIAQ FKSLSPQELQ AFKRAKDALE ESLLLKDCRC HSRLFPRTWD  60
LRQLQVRERP MALEAELALT LKVLEATADT DPALVDVLDQ PLHTLHHILS QFRACIQPQP 120
TAGPRTRGRL HHWLYRLQEA PKKESPGCLE ASVTFNLFRL LTRDLNCVAS GDLCV      175

SEQ ID NO: 4            moltype = DNA  length = 734
FEATURE                 Location/Qualifiers
source                  1..734
                        mol_type = unassigned DNA
                        organism = Homo sapiens
SEQUENCE: 4
tgggtgacag cctcagagtg tttcttctgc tgacaaagac cagagatcag gaatgaaact  60
agacatgact ggggactgca cgccagtgct ggtgctgatg ccgcagtgc tgaccgtgac  120
tggagcagtt cctgtcgcca ggctccacgg ggctctcccg gatgcaaggg gctgccacat 180
agcccagttc aagtccctgt ctccacagga gctgcaggcc tttaagaggg ccaaagatgc 240
cttagaagga tcgcttctgc tgaaggactg caggtgccac tcccgcctct tcccccaggac 300
ctgggaccty aggcagctgc aggtgaggga gcgccccatg gctttggagg ctgagctggc 360
cctgacgctg aaggttctgg aggccaccgc tgacactgac ccagccctgg tggacgtctt 420
ggaccagccc cttcacaccc tgcaccatat cctctcccag ttccgggcct gtatccagcc 480
tcagcccacg gcagggccca ggacccgggg ccgcctccac cattggctgt accggctcca 540
ggaggcccca aaaaaggagt cccctggctg cctcgaggcc tctgtcacct tcaacctctt 600
ccgcctcctc acgcgagacc tgaattgtgt tgccagtggg gacctgtgtg tctgaccctc 660
ccaccagtca tgcaacctga gattttattt ataaattagc cacttgtctt aatttattgc 720
cacccagtcg ctat                                                   734

SEQ ID NO: 5            moltype = AA  length = 175
FEATURE                 Location/Qualifiers
source                  1..175
                        mol_type = protein
                        organism = Homo sapiens
SEQUENCE: 5
VPVARLRGAL PDARGCHIAQ FKSLSPQELQ AFKRAKDALE ESLLLKDCKC RSRLFPRTWD  60
LRQLQVRERP VALEAELALT LKVLEATADT DPALGDVLDQ PLHTLHHILS QLRACIQPQP 120
TAGPRTRGRL HHWLHRLQEA PKKESPGCLE ASVTFNLFRL LTRDLNCVAS GDLCV      175

SEQ ID NO: 6            moltype = DNA  length = 656
FEATURE                 Location/Qualifiers
source                  1..656
                        mol_type = unassigned DNA
                        organism = Homo sapiens
SEQUENCE: 6
ctgcattccc tcagctccct ttctctctgt gacacagaca tgaccgggga ctgcatgcca  60
gtgctggtgc tgatggccgc agtgctgacc gtgactgagc cagttcctgt cgccaggctc 120
cgcggggctc tcccggatgc aaggggctgc cacatagccc agttcaagtc cctgtctcca 180
caggagctgc aggcctttaa gagggccaaa gatgccttag aagagtcgct tctgctgaag 240
gactgcaagt gccgctcccg cctcttcccc aggacctggg acctgaggca gctgcaggtg 300
agggagcggc ccgtggcttt ggaggctgag ctggcccctg cgctgaaggt tctggaggcc 360
accgctgaca ctgacccagc cctgggggat gtcttggacc agccccttca caccctgcac 420
catatcctct cccagctccg ggcctgtatc cagcctcagc cacggcagg gcccaggacc 480
cggggccgcc tccaccattg gctgcaccgg ctccaggagg ccccaaaaaa ggagtcccct 540
ggctgcctcg aggcctctgt caccttcaac ctcttccgcc tctcacgcg agacctgaat 600
tgtgttgcca gcggggaccct gtgtgtctga cccttccgcc agtcatgcaa cctgag     656

SEQ ID NO: 7            moltype = AA  length = 158
FEATURE                 Location/Qualifiers
source                  1..158
                        mol_type = protein
                        organism = Homo sapiens
SEQUENCE: 7
AAPRRCLLSH YRSLEPRTLA AAKALRDRYE EEALSWGQRN CSFRPRRDPP RPSSCARLRH  60
VARGIADAQA VLSGLHRSEL LPGAGPILEL LAAAGRDVAA CLELARPGSS RKVPGAQKRR 120
HKPRRADSPR CRKASVVFNL LRLLTWELRL AAHSGPCL                         158

SEQ ID NO: 8            moltype = DNA  length = 540
FEATURE                 Location/Qualifiers
source                  1..540
                        mol_type = unassigned DNA
                        organism = Homo sapiens
SEQUENCE: 8
atgcgggcga gtgtctgggc cgcagtggcc gcggggctgt gggtcctgtg cacggtgatc  60
gcagcggccc cccggcgctg cctgctctcg cactaccgct cgctggagcc ccggacgctg 120
gcggctgcca aggcgctgag ggaccgctac gaggaagagg cgctgagctg ggggcagcgc 180
aactgctcct tccgcccag gagggatcct ccgcggccat cgtcctgcgc tcggctccgg 240
cacgtggccc ggggcatcgc ggacgcccag gcagtgctca gcggcctgca ccgctcggag 300
ctgctccccg gcgccggccc gatcctggag ctgctggcgg ccgcggggag ggatgtggcg 360
```

```
gcctgccttg agctggcacg gccaggctcc tccaggaagg tccccggggc ccagaagagg    420
cgtcacaaac cccggagagc ggactcgcct cggtgccgca aagccagcgt ggtcttcaac    480
ctcctgcgcc tgctcacgtg ggagctccgg ctggctgcac actctgggcc ttgcctctga    540
```

MEDICAL USE OF INTERFERON-LAMBDA FOR THE TREATMENT OF FIBROSIS

CROSS-REFERENCE TO RELATED APPLICATIONS

This application is a continuation of co-pending U.S. application Ser. No. 16/469,236, filed Jun. 13, 2019, which is the U.S. National Stage of International Patent Application No. PCT/EP2017/083949, filed Dec. 20, 2017, which claims the benefit of Great Britain Application No. GB1621728.3, filed Dec. 20, 2016, the disclosures of all of which are hereby incorporated by reference herein.

The present invention relates to methods for the treatment of fibrosis. The invention discloses new research which demonstrates that interferon-lambda has directly acting antifibrotic effects both in vitro and in vivo and may be used to provide effective new therapies for the treatment of multiple types of fibrosis.

INCORPORATION-BY-REFERENCE OF MATERIAL SUBMITTED ELECTRONICALLY

Incorporated by reference in its entirety herein is a nucleotide/amino acid sequence listing submitted concurrently herewith and identified as follows: One 11.2 kilobyte XML document named "A-2860-US02-CNT.xml," created on Jun. 29, 2023.

BACKGROUND

Fibrotic diseases are diseases which are characterised by an aberrant wound healing response in which excess fibrous connective tissue is formed in an organ or tissue. The deposition and accumulation of excess extracellular matrix (ECM) components such as collagen and fibronectin results in the hardening and scarring of tissues, causing a pathological remodelling of the organ, and can ultimately lead to organ failure.

Wounding in solid organs typically starts with endothelial damage, platelet aggregation and activation initiating an inflammatory response with infiltration of neutrophils, macrophages, eosinophils and lymphocytes to the wound site. Infiltrating inflammatory cells and affected epithelial cells secrete a variety of growth factors and cytokines that serve to further amplify the inflammatory response. Molecules such as TGF-β, PDGF and IL-13 activate macrophages and lead to the recruitment, proliferation and activation of fibroblasts at the wound site. Activated fibroblasts or myofibroblasts, are characterised by the expression of α-smooth muscle actin and secrete collagen and other ECM components to stabilise the cellular substratum. This allows proliferation and migration of epithelial and endothelial cells over the temporary matrix to regenerate the damaged tissue. Once complete, the inflammatory process shuts down while fibroblasts undergo apoptosis leading to resolution of the wound response.

In fibrotic remodelling, persistent tissue insult or injury, or a disregulation of the repair pathway, leads to an inappropriate wound response. Excess deposition and hyper crosslinking of the collagen and ECM occurs, resulting in excessive accumulation of ECM above normal requirements, which is associated with persistent myofibroblast activation, damage to epithelial cells and a loss of the normal tissue architecture.

Fibrotic diseases can affect any organ or tissue, for example kidney, lung, intestine, skin, or liver. The cause of fibrotic disease can be dependent upon the organ or tissue involved and remains unknown in some diseases such as idiopathic pulmonary fibrosis. In other types of interstitial lung disease the cause is recognised, such as exposure to environmental allergens which causes hypersensitive pneumonitis. Liver fibrosis and ultimately cirrhosis results from chronic liver damage sustained through exposure to a variety of factors including environmental and dietary factors or infectious agents. Sustained over consumption of alcohol or a high fat/sugar diet can also lead to cirrhosis of the liver. Similarly, diabetes, hypertension, exposure to toxic agents and various types of autoimmune disease can damage the kidneys leading to fibrotic remodelling and loss of function. Many types of inflammatory bowel disease such as Crohn's disease or celiac sprue can lead to fibrotic remodelling causing strictures and/or malabsorption.

Treatment of progressive fibrosis is predominantly by treating the underlying disease. For example control of blood pressure, improved glucose management in diabetes, or removal of the damaging allergen or environmental cause. However, in many patients once the fibrotic remodelling has become established the disease becomes self-perpetuating and simple improved therapy of the initiating disease fails to halt the process. Some fibrotic diseases can be treated with anti-inflammatory and immunosuppressive agents, but these are only effective in subsets of patients and slow, rather than stop the disease.

To date there are only 2 validated therapies for fibrotic remodelling and both of these are solely licensed for use in idiopathic pulmonary fibrosis (IPF). Pirfenidone is a small molecule drug that was approved for use in the treatment of IPF in Japan in 2008 and Europe in 2011 which is likely to work via multiple mechanisms of action that are not completely understood but may work in part through a down-regulation of TGF-β. Nintedanib is a tri-angiokinase inhibitor blocking tyrosine kinase activity in VEGF, FGF and PDGF receptors. Both compounds slow the development of IPF, but likely only extending life by up to 2 years based on current studies. Further both are associated with significant side effects such that more than 30% of patients cannot tolerate their use long term. To date, no targeted therapies have been approved for fibrotic indications.

Therefore, there is currently an unmet medical need for improved treatment of fibrotic disease in all organs. Accordingly, it is an object of the present invention to provide a new method of treatment of fibrosis.

The discovery and initial description of the interferon-λ (IFN-λ) family in early 2003 opened an exciting new chapter in the field of IFN research. There are 4 distinct but highly related proteins denoted IFN-λ1, IFN-λ2, IFN-λ3 and IFN-λ4. These proteins are also known as interleukin-29 (IL-29), IL-28A, IL-28B and IFNL4, respectively. Collectively, these 4 cytokines comprise the type III subset of IFNs. They are distinct from both type I and type II IFNs for a number of reasons, including the fact that they signal through a heterodimeric receptor complex that is different from the receptors used by type I or type II IFNs. Although type I IFNs (IFN-a/b) and type III IFNs (IFN-l) signal via distinct receptor complexes, they activate the same intracellular signaling pathway and many of the same biological activities, including antiviral activity, in a wide variety of target cells. Consistent with their antiviral activity, expression of the IFN-λ genes and their corresponding proteins is inducible by infection with many types of viruses. Therefore, expression of the type III IFNs (IFN-λs) and their primary biological activity are very similar to the type I IFNs. However, unlike IFN-α receptors which are broadly expressed on most cell types, including leukocytes, IFN-λ receptors are largely restricted to cells of epithelial origin. The potential clinical importance of IFN-λ as a novel antiviral therapeutic agent is already apparent. In addition, preclinical studies by several groups indicate that IFN-λ may also be useful as a potential therapeutic agent for certain types of cancer.

In the present invention we disclose new research which demonstrates for the first time that cytokines of the interferon-lambda family have directly acting anti-fibrotic effects both in vitro and in vivo, and that these proteins may be used to design effective new methods for the treatment of multiple types of fibrosis.

DESCRIPTION OF THE INVENTION

Unless defined otherwise, all scientific and technical terms used herein have the same meaning as commonly understood by one of skill in the art to which this invention belongs. All publications and patents referred to herein are incorporated by reference.

It will be appreciated that any of the embodiments described herein may be combined.

The present invention provides interferon-lambda for use in the treatment of fibrosis. The invention also provides use of interferon-lambda for the preparation of a medicament for the treatment of fibrosis. The invention further provides a method for the treatment of fibrosis comprising administering a therapeutically effective amount of interferon-lambda.

Interferons (IFNs) are an important class of cytokines with diverse roles in host protection from viral infection and immune response modulation. Three distinct types of interferons are recognized (type I, II and III) based on their structural features, receptor usage and biological activities and their roles in host defence vary between the different types.

Type I IFNs (IFN-α/β/ω/ε/κ in humans) possess strong anti-viral activity and are able to induce a potent anti-viral response in a wide variety of cell types (Huang et al 1993). IFN-α/β binds a heterodimeric transmembrane receptor termed the IFNαR (composed of IFNAR1 and IFNAR2 subunits) which, upon engagement with ligand, triggers the activation of the kinases, JAK1 and TYK2, which then phosphorylate specific tyrosines in the intracellular domain of the receptor. This creates docking sites for STAT1 and STAT2 signalling molecules, leading to their recruitment and subsequent phosphorylation. The phosphorylated STATs recruit IFN regulatory factor 9 (IRF9), which together form IFN-stimulated gene factor 3 (ISGF3), which crosses into the nucleus and drives the transcription of IFN-stimulated genes (ISGs).

The type II class includes just IFN-γ, which is classified as a Th1-type cytokine that stimulates cell-mediated immune responses that are important for host protection against pathogenic microorganisms such as *Mycobacterium tuberculosis* (Bach et al 1997), has a central role in tumour immunity, and amplifies the anti-viral activity of type I IFNs. Therefore, type I and type II IFNs work together to activate both innate and adaptive immune responses, with the purpose of protecting the host against both infection and tumour invasion (Biron et al 2001).

IFNs are part of the larger family of class II cytokines that includes six IL-10-related cytokines: IL-10, IL-19, IL-20, IL-22, IL-24 and IL-26 (Kotenko 2002) and are classed together because they signal via receptors that share common motifs in their extracellular domains. These receptors comprise the class II cytokine receptor family (CRF2) and are typically heterodimers composed of 2 distinct receptor chains, α and β receptor subunits (Stahl et al 1993). In general, α subunits are the primary cytokine binding proteins, and the β subunits are required for formation of high affinity binding sites and for signal transduction.

The type III IFNs or IFN-λs are the most recent addition to the CRF2 family. They demonstrate structural features of the IL-10-related cytokines and induce anti-viral activity in a more restricted cell population than the type I IFNs, namely epithelial cells and certain immune cells (Kotenko et al, 2003; Sheppard et al, 2003). In humans, the type III IFN family is composed of 4 closely related proteins, IFN-λ1, -λ2, -λ3 and -λ4 (also known as IL-29, IL-28A, IL-28B and IFNL4, respectively) whereas the mouse only has IFN-λ2 and -λ3 (IL-28A and IL-28B, respectively). They are highly homologous; the amino acid identity between IFN-λ2 and IFN-λ3 is ~96% and the identity between IFN-λ1 and IFN-λ2/λ3 is ~81%. IFN-λ4 most closely resembles IFN-λ3 but these proteins only share ~30% identity and IFN-λ4 is predominantly intracellular and very poorly secreted in humans (Hong et al 2016).

The IFN-λ receptor complex is composed of the specific IFN-λ receptor chain 1 (IFN-λR1 or IL-28RA) and the shared IL-10 receptor chain 2 (IL-10R2 or IL-10Rβ). Engagement of the IFN-λ receptor complex by any of the four ligands leads to activation of JAK1 and TYK2, activation of the transcription factors STAT1, STAT2 and IRF9 to form the IFN-stimulated gene factor 3 (ISGF3). ISGF3 regulates gene transcription by binding to IFN-stimulated elements (ISRE) in the promoters of several hundred IFN-stimulated genes (ISGs) which include a number of genes that are associated with the antiviral phenotype, including OAS1, MX1, EIF2AK2 (double-stranded RNA-activated protein kinase) and IRF7. Comparative cDNA microarray analyses have shown that the repertoire of genes that are induced by type III IFNs (IFN-λ) is essentially the same as that induced by type I IFNs (IFN-α/β) (Doyle et al 2006). In conclusion, despite using different receptors, both type I and III IFNs activate ISGF3 (Zhou et al 2007), and therefore induce similar transcriptional responses.

Even though the pattern of gene expression induced by either type I or type III IFNs is very similar, the relative magnitude of gene expression induced by IFN-α is often greater than IFN-λ. This may reflect a difference in the relative strength of signalling through type I versus type III receptors or may simply reflect differences in expression levels of the respective receptors for these ligands.

The crystal structure of IFN-λ reveals a four-helix bundle structure typical of class II cytokines, with the closest structural homolog of IFN-λ, being IL-22 (Gad et al 2009) and may suggest that IFN-λ and IL-22 possess parallel functions, protecting epithelial tissue against viral and bacterial infections, respectively. The binding site on the IFN-2λR1 receptor chain is well conserved among all four IFN-λs, whereas the binding site on IL-10R2 is poorly defined (Miknis et al 2010). IFN-λR1 consists of two distinct fibronectin type III domains of approximately 100 amino acids each. The ligand-receptor interface includes helix A, loop AB and helix F on the IFN site, as well as loops primarily from the N-terminal domain and inter-domain hinge region of IFN-λR1. The binding mode between the ligand and receptor support an initial long range ionic interaction mediated via hydrogen bonding, which is then followed by hydrophobic interactions to finalize the fit.

IFN-λs are expressed by a variety of hematopoietic cells and epithelial cells in response to viral infection. Pattern-recognition receptors that detect the invading virus on the mucosal epithelial surface initiate a transcriptional response through the transcription factors NF-κB, IRF3, IRF7 and Med23 (Osterlund et al 2007, Griffiths et al 2013). The role of type 1 and type III IFNs in mediating anti-viral defences at mucosal interfaces has been shown to be both redundant and unique, depending on the virus and the point of entry. Gut epithelial cells respond exclusively to type III IFN which mediates control of epitheliotropic viruses, such as rotaviruses, in a non-redundant fashion (Pott et al 2011). Reoviruses initiate their infection in the gut epithelia but can penetrate the gut epithelial layer to cause a systemic infection in mice; type III IFN restricts the initial replication in the gut epithelium but type I IFNs are indispensable for the prevention of systemic infection (Mahlakoiv et al 2015). The compartmentalisation of type I and III IFNs is less clear in the respiratory tract where there is a degree of redundancy between the two IFN systems (Mordstein et al 2008). Thus, airway epithelia express receptors for both IFN types whereas gut epithelia express only IFN-λ receptors.

IFN-λR1 receptor expression is restricted mainly to epithelial cells and certain immune cell subsets such as monocyte-derived macrophages, plasmacytoid dendritic cells and NK cells in certain scenarios. Activation of IFN-λR1 in NK cells is linked to maximal production of IFN-γ and anti-tumour activity which may be an effect mediated synergistically with other stimuli or in combination with other cell types (Souza-Fonseca-Guimaraes et al 2015). Owing to the restricted IFN-αR1 expression to immune cells and epithelial cells, the immunomodulatory effects of the type III IFNs are limited but are very effective anti-virals when a local mucosal response is sufficient to control the virus. This is in contrast to the ubiquitous activity of type I IFNs during responses to infection, and therefore more appropriate in the control of severe or systemic infection where widespread immune activation is necessary.

The following references describe differences in signalling and biological effects between type I and type III interferons: Wack et al 2015, Chow & Gale 2015, Hemann et al 2017, Broggi et al 2017, Blumer et al 2017, Chiriac et al 2017, Bhushal et al 2017, Andreakos et al 2017, and Bhushal et al 2017.

The contribution of IFN-λs to antiviral therapies is well established with data available in pre-clinical models in mice and chimpanzees and, in vitro, in primary human hepatocytes infected with hepatitis C virus (HCV) (Thomas et al 2012, Park et al 2012) and in human clinical trials (PhII BMS data). The range of viruses that can be targeted with IFN-λ include but are not restricted to the following: influenza A/B, severe acute respiratory syndrome (SARS), coronavirus, H1 N1, human immunodeficiency virus (HIV), herpes simplex virus type 2 (HSV2), cytomegalovirus (CMV), Middle East respiratory syndrome (MERS), nororvirus, rotavirus and Ebola (Eslam and George 2015; Gresser 2015). All of these viruses target an epithelial point of entry and therapeutically could be targeted with IFN-λ, which can activate the IFN-λR1 receptor complex at this access point.

Numerous preclinical studies have demonstrated that IFN-λs have anti-tumour activity in a range of tumour types such as hepatoma, melanoma, oesophageal carcinoma, neuroendocrine tumours, colorectal carcinoma, lung adenocarcimoma and Burkitt's lymphoma (Sato et al 2006, Zitzmann et al 2006, Steen et al 2010). The anti-tumour mechanisms of IFN-λs are tumour cell induction of apoptosis and a direct effect on immune cells to boost both the innate and adaptive immune stimulatory activities. IFN-λs are induced in the tumour microenvironment and signalling through the IFN-λR1 receptor has been shown to play an anti-tumour role in IFN-λR1 knockout mice which are more susceptible to sarcoma formation and death in transplanted tumour models. IFN-λ treatment delayed lethality and reduced sarcoma development (Numasaki et al 2007). In the context of cancer treatment, IFN-λs could be envisioned to complement current IFN-α therapy, immune check-point inhibitors or as adjunctives to traditional anti-cancer agents such as bortezomib, temozolomide, cisplatin or 5-FU (Guenterberg et al 2010, Li et al 2010).

Genetic and functional evidence has suggested a protective role for IFN-λ in inflammatory diseases such as asthma, psoriasis and rheumatoid arthritis. In a mouse model of asthma, IFN-λ minimized disease severity, reduced eosinophil infiltration and demonstrated a Th1 immune skewing effect away from Th2 and Th17 cytokines (Koltsida et al 2011). In a mouse collagen-induced arthritis model, IFN-λ2 treatment resulted in abrogation of disease by suppressing IL-1 and IL-17 responses, as well as neutrophil recruitment (Blazek et al 2015). In psoriatic lesions, Th17 cells have been shown to be a source of IFN-λ, where it can suppress the Th2 cytokine, IL-13 (Wolk et al 2013). The role of IFN-λs in inflammatory and autoimmune diseases is still ambiguous.

Three landmark genome wide association studies (GWAS) on HCV have demonstrated that single nucleotide polymorphisms (SNPs) in the IFN-λ region are the strongest single predictor of both response to pegylated IFN-λ1/ribavirin (PEG-IFN/RBV) therapy and spontaneous clearance of chronic HCV infection. These SNPs map to the IFNL3/IFNL4 gene locus and have been shown to be effective for all HCV genotypes and in all geographical locations (Ge et al 2009, Suppiah et al 2009, Tanaka et al 2009). The role of IFNL3/IFNL4 genotype in predicting treatment outcomes to all anti-viral therapies (including both first and second generation direct-acting antiviral drugs) also extends to a wide list of other viral infections including CMV, HSV and Epstein-Barr virus (EBV), and also to co-infection with HCV/HIV and HCV/HBV (Rallon et al 2010, Guo et al 2013). Data are consistent with a primary role for IFN-λ in controlling viral infections in different organs, particularly those of epithelial origin.

There is evidence for the role of two SNPs in liver fibrosis, namely the rs12979860 and rs8099917 'responder' genotypes, and the acceleration of hepatic inflammation and fibrosis, in hepatitis C and hepatitis B virus infections and non-alcoholic fatty liver disease (Bochud et al 2012, Eslam et al 2015).

Two functional variants in the IFNL3/IFNL4 region have been described that link to the original GWAS discovery but there may be many other as yet unidentified contributory factors. The first SNP is ΔG/TT (rs368234815) that controls the production of IFN-λ4 and also predicts HCV clearance (Prokunina-Olsson et al 2013). The ancestral 'ΔG' allele encodes a functional IFN-λ4, which impairs HCV clearance and hence increases viral load, whereas the more recent (in evolutionary terms) 'TT' allele of rs368234815 disrupts the open reading frame of IFNL4 (disrupting protein expression) and is associated with improved viral clearance. This apparent paradox may be linked to the predominantly intracellular localization and poor secretion of IFNL4 and the suggestion that IFNL4 may inhibit the secretion and hence function of the other IFN-λ family members. A second SNP in the 3'UTR region of IFNL3 (rs4803217) affects the messenger RNA stability of IFNL3 (McFarland et al 2014). Although the role of these variants in predicting liver fibrosis is unknown, especially in non-HCV cohorts, they are in linkage disequilibrium with rs12979860 so more work is needed to show if there is any association.

In summary, to date IFN-λs have been described to have antiviral and anti-tumour activity, immune-inflammatory functions and homeostatic effects. In the present invention, we disclose that IFN-λs unexpectedly have directly acting anti-fibrotic effects both in vitro and in vivo. The Examples demonstrate that interferon-lambda proteins have anti-fibrotic effects in in vivo mouse chronic kidney disease models and in in vitro human fibrosis models with relevant primary cells from liver, small intestine, skin, kidney and lung organ systems. These proteins therefore have unexpected potential as anti-fibrotic agents in multiple types of fibrosis, and may be used to design effective new therapies for the treatment of fibrotic diseases.

The terms interferon-lambda (IFN-λ) and interferon-lambdas (IFN-λs) are used interchangeably herein to refer to cytokines of the interferon-lambda family. The interferon-lambda proteins and the interferon-lambda receptor are also known by a number of other synonyms as shown in Table 1.

TABLE 1

| protein | synonyms |
| --- | --- |
| interferon lambda-1 | IFN-λ1 |
|  | IFNL1 |
|  | interleukin-29 |
|  | IL-29 |
| interferon lambda-2 | IFN-λ2 |
|  | IFNL2 |
|  | interleukin-28A |
|  | IL-28A |
|  | cytokine Zcyto20 |
|  | ZCYTO20 |
| interferon lambda-3 | IFN-λ3 |
|  | IFNL3 |
|  | interleukin-28B |
|  | IL-28B |
|  | ZCYTO22. |
| interferon lambda-4 | IFN-λ4 |
|  | IFNL4 |
| interferon-lambda receptor | IFN-LR1 |
|  | IL-28R1 |
|  | IL-28RA |
|  | IFN-λR1 |

In one embodiment, the interferon-lambda is IFN-λ1.
In one embodiment, the interferon-lambda is IFN-λ2.
In one embodiment, the interferon-lambda is IFN-λ3.
In one embodiment, the interferon-lambda is IFN-λ4.

Amino acid and DNA sequences for IFN-λ1, IFN-λ2, IFN-λ3, and IFN-λ4, are shown in FIG. 18.

The IFN-λ may be used in the form of a fusion protein, such as an Fc fusion. An Fc fusion protein is composed of an Fc domain of an antibody (e.g. an IgG) fused to the IFN-λ. Fc fusion proteins form dimers as a result of association of the Fc domains. The IFN-λ may thus be in dimeric form, as well as monomeric form.

Functional Mimetics

In one embodiment, the interferon-lambda is a functional mimetic of IFN-λ1.
In one embodiment, the interferon-lambda is a functional mimetic of IFN-λ2.
In one embodiment, the interferon-lambda is a functional mimetic of IFN-λ3.
In one embodiment, the interferon-lambda is a functional mimetic of IFN-λ4.

The term "functional mimetic" means a molecule which has the same or similar biological effects as the wild-type protein. For example an interferon-lambda functional mimetic may activate the interferon-lambda receptor and drive the transcription of IFN-stimulated genes.

In one embodiment, the functional mimetic may reduce hydroxyproline levels in an in vivo model of fibrosis as described in Example 1. In one embodiment, the functional mimetic may inhibit fibronectin and/or collagen deposition in an in vitro model of fibrosis as described in Example 2.

In one embodiment, the interferon-lambda functional mimetic is a fragment of IFN-λ1.
In one embodiment, the interferon-lambda functional mimetic is a fragment of IFN-λ2.
In one embodiment, the interferon-lambda functional mimetic is a fragment of IFN-λ3.
In one embodiment, the interferon-lambda functional mimetic is a fragment of IFN-λ4.
In one embodiment, the interferon-lambda functional mimetic is a variant of IFN-λ1.
In one embodiment, the interferon-lambda functional mimetic is a variant of IFN-λ2.
In one embodiment, the interferon-lambda functional mimetic is a variant of IFN-λ3.
In one embodiment, the interferon-lambda functional mimetic is a variant of IFN-λ4.

A variant interferon-lambda may be or may comprise a variant of one of the specific sequences shown in FIG. 18. For example, a variant may be a substitution, deletion or addition variant of any of the amino acid sequences in FIG. 18. A fragment of an IFN-λ may, for example, have a size of greater than 50 amino acids, greater than 100 amino acids or greater than 150 amino acids.

A variant interferon-lambda may comprise 1, 2, 3, 4, 5, up to 10, up to 20 or more (typically up to a maximum of 50) amino acid substitutions, deletions and/or additions compared with the specific amino acid sequences in FIG. 18. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants typically involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are shown in Table 2.

TABLE 2

| Ala | aliphatic, hydrophobic, neutral |
| --- | --- |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |

TABLE 2-continued

| | |
|---|---|
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

A variant interferon-lambda may have an amino acid sequence which has more than about 60%, or more than about 70%, e.g. 75 or 80%, typically more than about 85%, e.g. more than about 90 or 95% amino acid identity to the amino acid sequences in FIG. 18. Variants may retain at least about 90%, 91%, 92%, 93%, 94%, 95%, 96%, 97%, 98% or 99% identity to the sequences in FIG. 18. Variants typically retain about 60%-about 99% identity, about 80%-about 99% identity, about 90%-about 99% identity or about 95%-about 99% identity. This level of amino acid identity may be seen across the full length of the relevant SEQ ID NO sequence or over a part of the sequence, such as across about 20, 30, 50, 75, 100, 150, 200 or more amino acids.

The term "identity" as used herein, indicates that at any particular position in the aligned sequences, the amino acid residue is identical between the sequences. The term "similarity" as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains)

lysine, arginine and histidine (amino acids having basic side chains);

aspartate and glutamate (amino acids having amide side chains); and cysteine and methionine (amino acids having sulphur-containing side chains).

In one embodiment, the interferon-lambda functional mimetic is a derivative of IFN-λ1.

In one embodiment, the interferon-lambda functional mimetic is a derivative of IFN-λ2.

In one embodiment, the interferon-lambda functional mimetic is a derivative of IFN-λ3.

In one embodiment, the interferon-lambda functional mimetic is a derivative of IFN-λ4.

In one embodiment, the interferon-lambda may be or may comprise a derivative of one of the specific sequences shown in FIG. 18. In one example, a derivative may include a structural analogue of a naturally occurring amino acid. Alternatively, an amino acid may be modified, for example labelled.

In one embodiment the interferon-lambda of the invention is pegylated i.e. the interferon-lambda is covalently attached to poly(ethyleneglycol) (PEG). Methods for producing pegylated proteins are well known in the art, see for example Chapman A et al., 2002, Advanced Drug Delivery Reviews 54: 531-545.

In one embodiment, the pegylated interferon-lambda is Peginterferon Lambda-1a "Lambda". (Andersen et al., 2013). "Lambda" is an investigational type III interferon therapeutic agent originally developed at ZymoGenetics (now a fully owned subsidiary of Bristol-Myers Squibb). It was licensed to Eiger Biopharmaceuticals in 2016 and is currently in clinical development for the treatment of chronic hepatitis delta virus (HDV) infection.

In one embodiment, the interferon-lambda functional mimetic is an antibody.

The antibody molecules of the present invention may comprise a complete antibody molecule having full length heavy and light chains or a fragment or antigen-binding portion thereof. The term "antigen-binding portion" of an antibody refers to one or more fragments of an antibody that retain the ability to selectively bind to an antigen. It has been shown that the antigen-binding function of an antibody can be performed by fragments of a full-length antibody. The antibodies and fragments and antigen binding portions thereof may be, but are not limited to Fab, modified Fab, Fab', modified Fab', F(ab')₂, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO2009/040562. Multi-valent antibodies may comprise multiple specificities or may be monospecific (see for example WO 92/22853 and WO 05/113605). These antibody fragments may be obtained using conventional techniques known to those of skill in the art, and the fragments may be screened for utility in the same manner as intact antibodies.

The antibody of the invention is an interferon-lambda functional mimetic and elicits the same or similar biological effects as the wild-type protein. For example the antibody may bind to an epitope on the interferon-lambda receptor, activating receptor signalling and driving the transcription of IFN-stimulated genes.

In one embodiment, the interferon-lambda derivative is a small molecule chemical entity (such as a chemical entity with a molecular weight less than 900 Daltons).

Methods of screening chemical libraries to identify small molecule chemical entities which may be potential drug candidates are known in the art. For example, a chemical library may be tested in a ligand-receptor binding assay, or in a cell culture model of organ fibrosis, as described in Example 2.

Fibrotic Diseases

Examples of fibrotic diseases which may be treated using the interferon-lambda of the invention include, but are not limited to interstitial lung disease, pulmonary fibrosis, such as idiopathic pulmonary fibrosis, silicosis, hypersensitivity pneumonitis, non-specific interstitial pneumonia, rheumatoid lung, scleroderma, chronic obstructive pulmonary disease and cystic fibrosis; renal fibrosis (including chronic glomeruonephritis, tubulointerstitial nephropathies and genetic diseases of the kidney) such as diabetic nephropathy, hypertensive nephrosclerosis, focal segmental glomerulosclerosis, IgA nephropathy, mesangial proliferative glomerulonephritis, membranous nephropathy, renovascular disease, polycystic kidney disease, chronic allograft nephropathy and Goodpastures disease; liver fibrosis and liver cirrhosis including primary sclerosing cholangitis, primary biliary cirrhosis, alcohol induced liver diseases and nonalcoholic steatohepatitis (including other fatty acid liver diseases); as well as endomyocardial fibrosis, mediastinal fibrosis, myelofibrosis, retroperitoneal fibrosis, encapsulating peritoneal fibrosis, progressive massive fibrosis, nephrogenic systemic fibrosis, Crohn's disease (plus other gut stricture causing diseases), keloid, myocardial infarction, scleroderma, systemic sclerosis and arthrofibrosis.

In one embodiment, the fibrosis is kidney fibrosis (in which case the IFN-λ may be IFN-λ1, IFN-λ2, IFN-λ3, or IFN-λ4).

In one embodiment, the fibrosis is lung fibrosis (in which case the IFN-λ may be IFN-λ1, IFN-λ2, IFN-λ3, or IFN-λ4).

In one embodiment, the fibrosis is small intestine fibrosis (in which case the IFN-λ may be IFN-λ1, IFN-λ2, IFN-λ3, or IFN-λ4).

In one embodiment, the fibrosis is skin fibrosis (in which case the IFN-λ may be IFN-λ1, IFN-λ2, IFN-λ3, or IFN-λ4).

In one embodiment, the fibrosis is liver fibrosis (in which case the IFN-λ may be IFN-λ1, IFN-λ2, IFN-λ3, or IFN-λ4).

In one embodiment, the fibrosis is peritoneal fibrosis (in which case the IFN-λ may be IFN-A1, IFN-λ2, IFN-λ3, or IFN-λ4).

In one embodiment, the fibrosis is pancreatic fibrosis (in which case the IFN-λ may be IFN-λ1, IFN-λ2, IFN-λ3, or IFN-λ4).

In one embodiment, the fibrosis is atherosclerosis (in which case the IFN-λ may be IFN-A1, IFN-λ2, IFN-λ3, or IFN-λ4).

In one embodiment, the fibrosis is selected from the group consisting of kidney fibrosis, lung fibrosis, small intestine fibrosis, skin fibrosis, liver fibrosis, peritoneal fibrosis, pancreatic fibrosis and atherosclerosis.

In one embodiment, the fibrosis is selected from the group consisting of kidney fibrosis, lung fibrosis, small intestine fibrosis, skin fibrosis, peritoneal fibrosis, pancreatic fibrosis and atherosclerosis.

In one embodiment, the fibrosis is not associated with a microbial infection, for example a viral infection. Thus, the subject treated in the invention may be one who does not have an infection such as a viral infection. For example, the subject may be one who does not have a viral infection that is known to be treatable by IFN-λ. The subject may be one who is not infected by a hepatitis virus, such as hepatitis A, B or C; influenza virus; severe acute respiratory syndrome (SARS) virus; coronavirus; human immunodeficiency virus (HIV); herpes simplex virus type 2 (HSV2); cytomegalovirus (CMV); Middle East respiratory syndrome (MERS) virus; norovirus; rotavirus; or Ebola virus.

Pharmaceutical Compositions, Dosages and Dosage Regimes

An interferon-lambda of the invention, or a functionally active fragment or derivative thereof, may be provided in a pharmaceutical composition. The pharmaceutical composition will normally be sterile may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the interferon-lambda or functionally active fragment or derivative thereof may be coated in a material to protect it from the action of acids and other natural conditions that may inactivate it.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising an interferon-lambda of the invention and instructions for use. The kit may further contain one or more additional reagents, such as an additional therapeutic or prophylactic agent as discussed above.

The interferon-lambda of the invention, or formulations or compositions thereof may be administered for prophylactic and/or therapeutic treatment of a fibrotic disease.

In one embodiment the treatment of a fibrotic disease is a therapeutic treatment. In therapeutic applications, compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In one embodiment the treatment of a fibrotic disease is a prophylactic treatment. In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount".

Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is typical.

An antibody/modulator or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, a pharmaceutical composition of the invention can be administered via a non-parenteral route, such as a topical, epidermal or mucosal route of administration. The pharmaceutical composition of the invention may be for oral administration.

A suitable dosage of a pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, modulators/antibodies or pharmaceutical compositions of the invention may be co-administered with one or other more other therapeutic agents.

Combined administration of two or more agents may be achieved in a number of different ways. Both may be administered together in a single composition, or they may be administered in separate compositions as part of a combined therapy. For example, the one may be administered before, after or concurrently with the other.

In one embodiment the interferon-lambda of the invention is administered in combination with another therapeutically active compound. In one embodiment the other therapeutically active compound is another anti-fibrotic therapeutic agent.

Alternatively, the interferon-lambda may be administered not in combination with another therapeutically active compound. For example, the patient treated with the interferon-lambda may be one who is not treated with an antiviral agent, such as another interferon (e.g. a type I interferon or a type II interferon such as interferon-gamma).

FIGURES

Figure 1C:
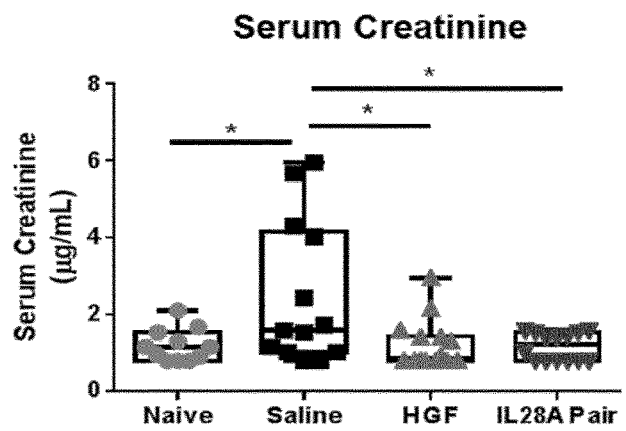
Figure 2A:
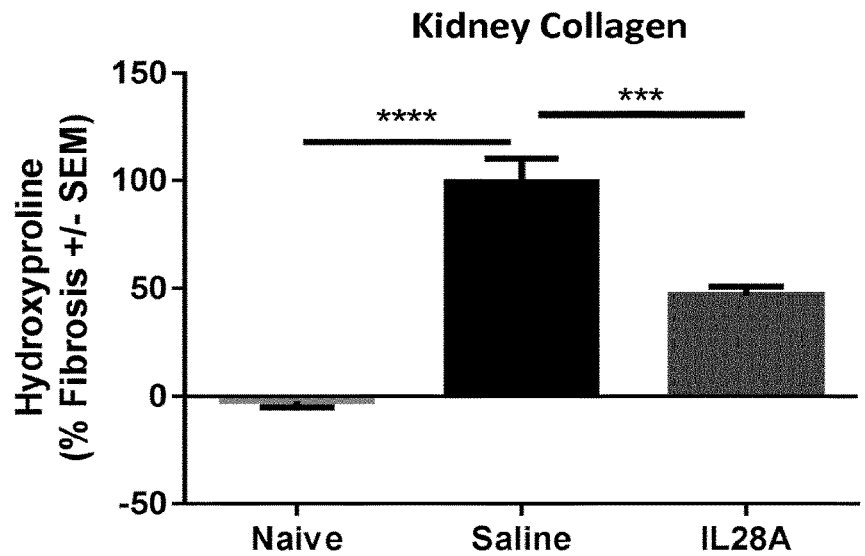
Figure 2B:
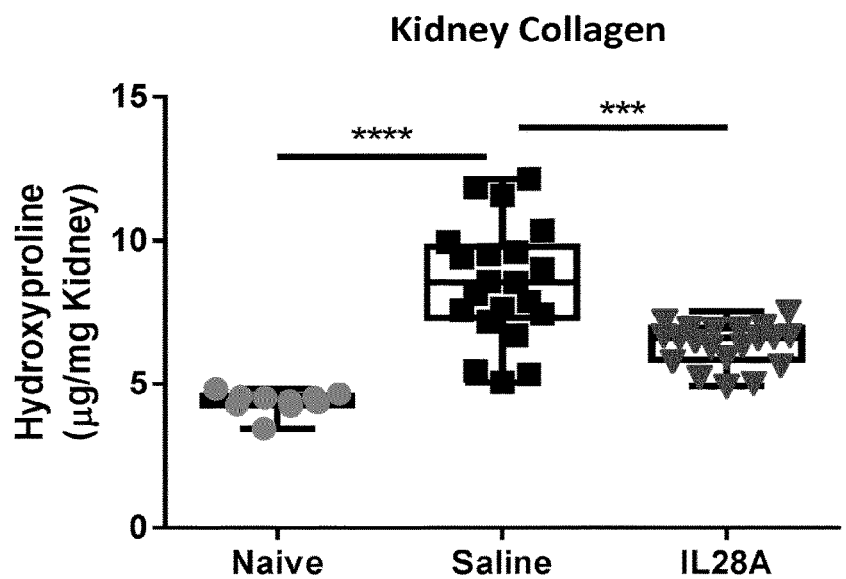
Figure 2C:
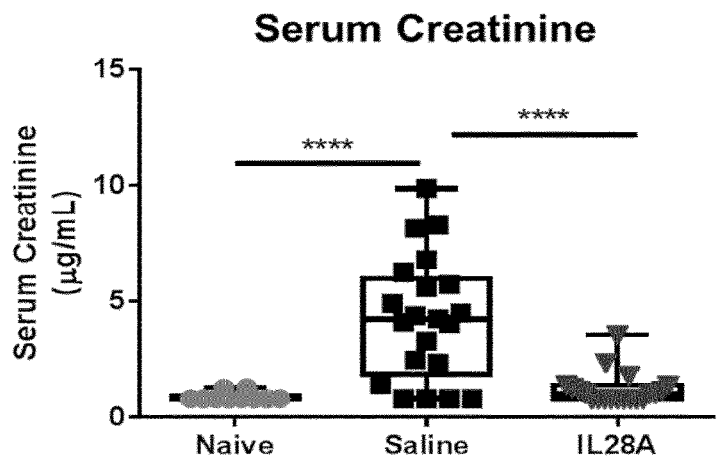
Figure 2D:
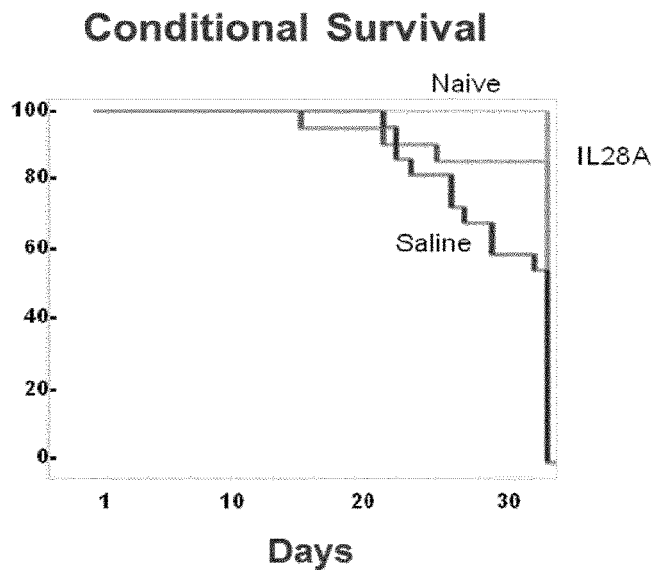

FIG. 1: Identification of IL-28A as an anti-fibrotic hit in an Adriamycin model of Kidney disease In screening-conditions, mouse IL-28A (ILFNL2) was introduced into the mouse by hydrodynamic transfection as a cDNA pair (ie IL-28A cDNA with another undisclosed cDNA) (n=15 group size for all treatment arms) before the administration of Adriamycin by IV injection to induce chronic kidney disease. Control mice were transfected with just saline prior to Adriamycin injection. Mice were monitored up to 49 days and on termination kidney hydroxyproline levels (FIGS. 1(a) and (b)) and serum creatinine levels (FIG. 1(c)) were measured (there is no conditional survival data for the primary screen). Figures for Hydroxyproline (µg/mg Kidney) and Serum Creatinine (µg/mL) are box and whisker plots. The central horizontal line shows the median of the data and the box extends from the 25$^{th}$ to the 75$^{th}$ percentiles. The 'whiskers' cover a typical range of the data. Normalized Hydroxyproline (Kidney collagen) show the mean with an error bar of +SEM, **$p<0.0001$, *$p<0.001$, *$p<0.05$.

FIG. 2: Confirmation of IL-28A as an anti-fibrotic hit in an Adriamycin model of Kidney disease Mouse IL-28A (IFNL2) was introduced into the mice by hydrodynamic transfection as a single cDNA (n=22 group size for all treatment arms) before the administration of Adriamycin by IV injection to induce chronic kidney disease. Control mice were transfected with just saline prior to Adriamycin injection. Mice were followed up for 49 days. On termination kidney hydroxyproline levels (FIGS. 2(a) and (b)) and serum creatinine levels (FIG. 2(c)) were measured and conditional survival data was recorded throughout the study period (FIG. 2(d)).

Figures for Hyroxyproline (µg/mg Kidney) and Serum Creatinine (µg/mL) are box and whisker plots. The central horizontal line shows the median of the data and the box extends from the 25$^{th}$ to the 75$^{th}$ percentiles. The 'whiskers' cover a typical range of the data. Normalized Hydroxyproline (Kidney collagen) show the mean with an error bar of +SEM, **$p<0.0001$, *$p<0.001$, *$p<0.05$.

Figure 3C:
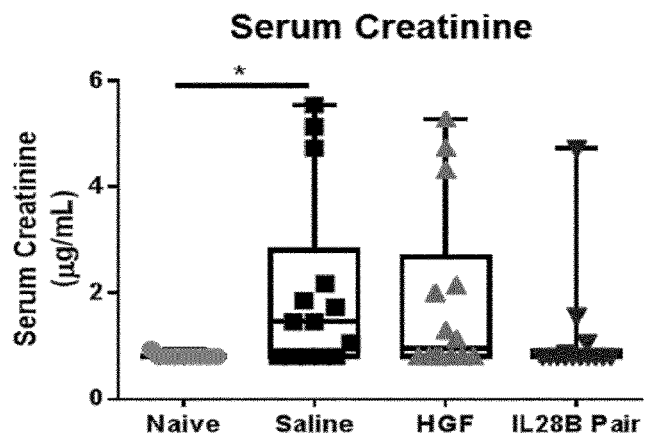
Figure 4A:
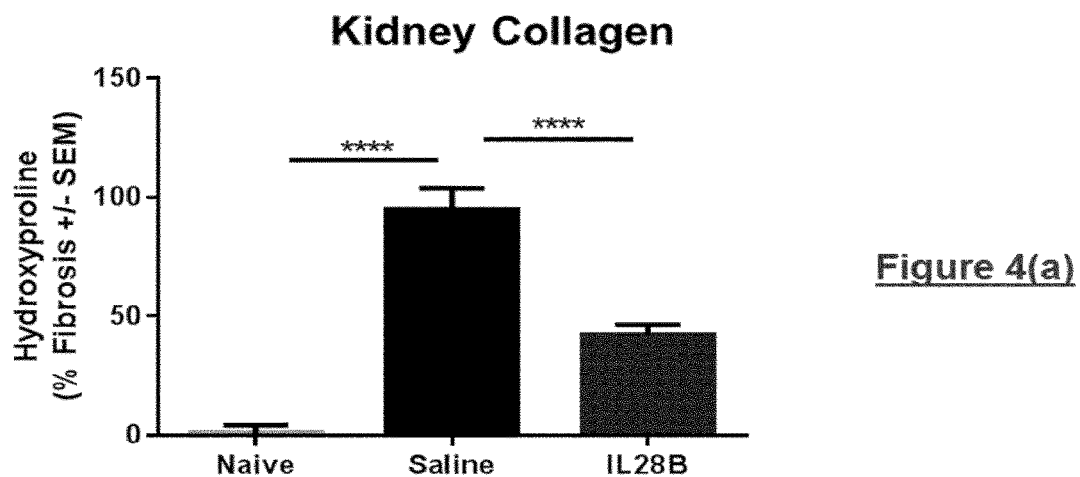
Figure 4B:
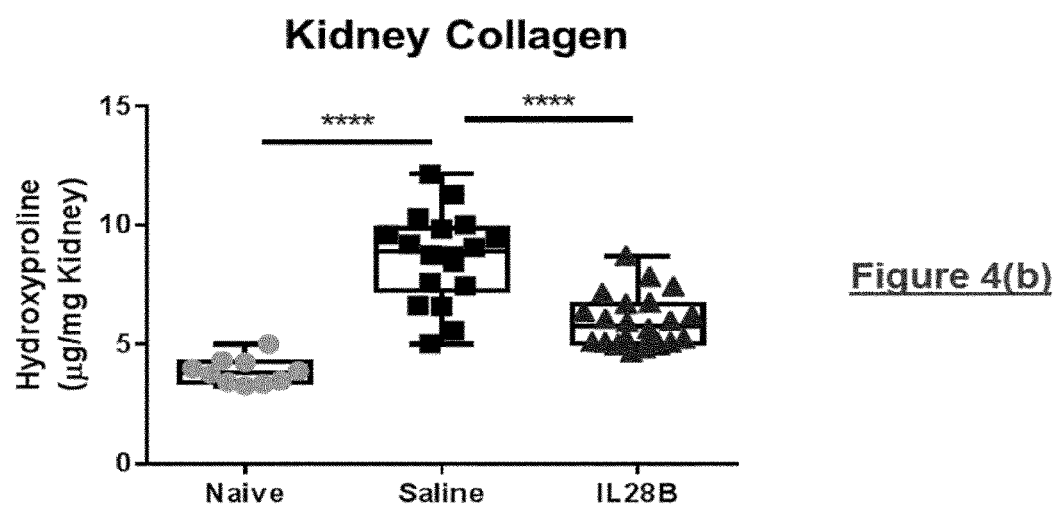
Figure 4C:
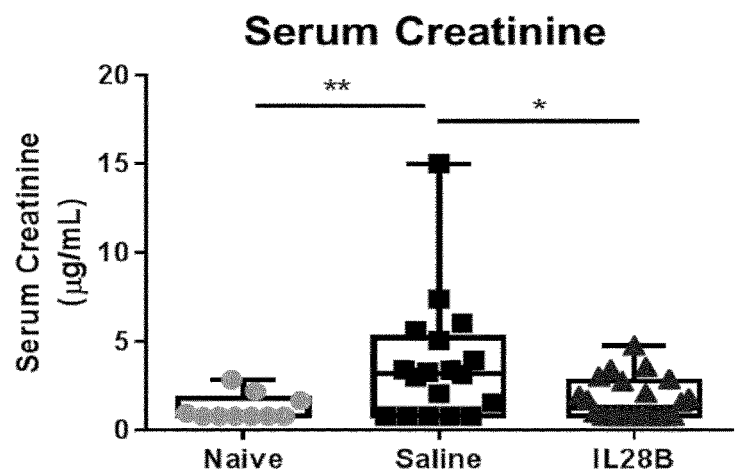
Figure 4D:
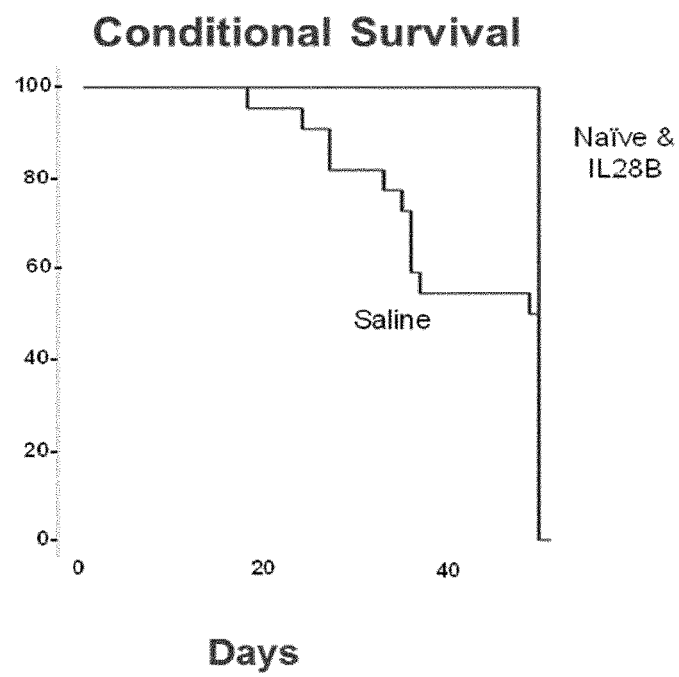

FIG. 3: Identification of IL-28B as an anti-fibrotic hit in an Adriamycin model of Kidney disease In the primary screen, mouse IL-28B (ILFNL3) was introduced into the mouse group by hydrodynamic transfection as a cDNA pair (n=15 group size for all treatment arms) before Adriamycin, and the mice were monitored up to 49 days and on termination kidney hydroxyproline levels (FIGS. 3(a) and (b)) and serum creatinine levels (FIG. 3(c)) were measured (there is no conditional survival data for the primary screen). Control mice were transfected with just saline prior to Adriamycin injection.

Figures for Hyroxyproline (µg/mg Kidney) and Serum Creatinine (µg/mL) are box and whisker plots. The central horizontal line shows the median of the data and the box extends from the 25$^{th}$ to the 75$^{th}$ percentiles. The 'whiskers' cover a typical range of the data. Normalized Hydroxyproline (Kidney collagen) show the mean with an error bar of +SEM, **p<0.0001, *p<0.001, *p<0.05.

FIG. 4: Confirmation of IL-28B as an anti-fibrotic hit in an Adriamycin model of Kidney disease Mouse IL-28B (IFNL3) was introduced into the mouse group by hydrodynamic transfection as a single clone (n=22 group size in each treatment arm) before Adriamycin, and the mice were followed up to 49 days. Control mice were transfected with just saline prior to Adriamycin injection. On termination kidney hydroxyproline levels (FIGS. 4(a) and (b)) and serum creatinine levels (FIG. 4(c)) were measured and conditional survival data was recorded throughout the study period (FIG. 4(d)).

Figures for Hyroxyproline (μg/mg Kidney) and Serum Creatinine (μg/mL) are box and whisker plots. The central horizontal line shows the median of the data and the box extends from the 25$^{th}$ to the 75$^{th}$ percentiles. The 'whiskers' cover a typical range of the data. Normalized Hydroxyproline (Kidney collagen) show the mean with an error bar of +SEM, **p<0.0001, *p<0.001, *p<0.05.

FIG. 5: Histological confirmation of IL-28B and IL-28A as anti-fibrotic in an Adriamycin model of Kidney disease At termination, kidneys from the study described in FIG. 2 and FIG. 4 were fixed in NBF, paraffin-embedded, sectioned, and stained with either Haematoxylin and Eosin (H&E), picro-sirius red (PSR) or masons trichrome (MT). The slides were then imaged with a Hamamatsu slide scanner. Representative images of the PSR-stained kidneys sections are shown for IL-28B in FIG. 5(a) for 1 naïve mouse, 3 saline Adriamycin-treated mice and 3 Adriamycin-treated mice that also received IL-28B and for IL-28A in FIG. 5(f) for 1 naïve mouse, 3 saline Adriamycin-treated mice and 3 Adriamycin-treated mice that also received IL-28A. All the terminal mice kidney sections for both IL-28B groups (10 naïve, 18 saline and 22 IL-28B-treated mice) and IL-28A groups (8 naïve, 20 saline and 19 IL-28A-treated mice) were imaged and the total area covered by the PSR stain was estimated using the Definiens image analyses platform are presented in FIG. 5(b) and FIG. 5(g), respectively. In addition all slides were manually scored for fibrosis by separate experts in the field of fibrosis (2 scientists and 1 clinical pathologist) and the Pathology scores were calculated for IL-28B from H&E stain (FIG. 5(c)), and PSR stain (FIGS. 5(d) and (e)) and for IL-28A from PSR stain (Fig(h)) and MT stain (Fig(i)). Magnification=×100.

FIG. 6: Effect of IL-28A in a Liver in vitro ECM fibrosis model

Human primary stellate cells (FIG. 6(a)) (seeded at 1000 cells/well) or human primary stellate cells in co-culture with human primary hepatocytes (FIG. 6(b)) (seeded at 1000 cells/well, 1:1 ratio) were treated with IL-28A in culture for 5 days. Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

FIG. 7: Effect of IL-28A and IL-28B in a Liver in vitro ECM fibrosis model plus TGFβ

Human primary stellate cells (at 1000 cells/well) (FIG. 7a)) or human primary stellate cells in co-culture with human primary hepatocytes (at 1000 cells/well, 1:1 ratio) (FIG. 7(b)) were treated with IL-28A or IL-28B in culture for 5 days in the presence of TGFβ at 250 μg/ml. Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

FIG. 8: High content images showing the effect of IL-28A and IL-28B in TGFβ1-stimulated stellate cell-hepatocyte co-culture ECM Human primary stellate cells in co-culture with primary hepatocytes (in a ratio of 1:1 with a final cell concentration of 1000 cells/well), stimulated with TGFβ1 (250 pg/ml) were cultured alone (TGFβ1 co-culture) or treated with IL-28A or IL-28B at 10000, 1000, 100 or 10 ng/ml for 5 days. Images shown are from 1 representative field out of 16 fields for each condition. Magnification was performed with a ×10 objective.

FIG. 9: Effect of IL-28A, IL-28B and IL-29 in a TGFβ1-stimulated small intestine fibroblast ECM in vitro model Human primary small intestinal fibroblasts (at 2000 cells/well) were treated with IL-28A, IL-28B or IL-29 (all at 10 ng/ml) in culture for 7 days in the presence of TGF3 (10 ng/ml). Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

FIG. 10: % Inhibition of IL-28A and IL-28B in a Skin keratinocyte-fibroblast co-culture ECM in vitro model Human primary dermal fibroblasts from 3 individual batches were placed in co-culture with primary human keratinocytes (in a ratio of 9:1 with a final cell concentration of 1500 cells/well) and treated with increasing amounts of IL-28A or IL-28B for 7 days. Cells were removed & the ECM proteins, Fibronectin, Collagen I&III and Collagen IV were measured by immunofluorescent labelling with imaging and quantification on a Cellomics Arrayscan. The normalized data from the 3 batches was calculated as % inhibition and plotted as Mean±SD. Cell viability was measured with PrestoBlue, with the 3 fibroblast batches in co-culture with keratinocytes normalized to control co-culture and the data averaged to give the fold change.

FIG. 11: Effect of IL-28A, IL-28B and IL-29 in a Skin keratinocyte-fibroblast co-culture ECM in vitro model Human primary dermal fibroblasts in co-culture with primary human keratinocytes (in a ratio of 9:1 with a final cell concentration of 1500 cells/well) were treated with IL-29, IL-28A or IL-28B for 7 days in the concentration range of 1250-10000 ng/ml cytokine. Cells were removed & the ECM proteins, Fibronectin, Collagen I&III and Collagen IV were measured by immunofluorescent labelling, with imaging and quantification on a Cellomics Arrayscan. Data represents Mean Total Intensity plotted as Mean+/−SD of 4 separate wells. Cell viability was measured with PrestoBlue.

FIG. 12: High content images showing the effect of IL-28A, IL-28B and IL-29 in a Skin keratinocyte-fibroblast co-culture ECM in vitro model Human primary dermal fibroblasts from a representative donor in co-culture with primary keratinocytes (in a ratio of 9:1 with a final cell concentration of 1500 cells/well) were cultured alone (control) or treated with IL-29, IL-28A or IL-28B at 10000 or 1250 ng/ml for 7 days. The images represent the combined signal from the Fibronectin, Col I&III and Col IV ECM matrix proteins and shows 1 representative field from a total of 16 fields per condition. Magnification was performed with a ×10 objective.

FIG. 13: Effect of IL-28A and IL-28B in a IL-1α-stimulated skin fibroblast ECM in vitro model Human primary dermal fibroblasts (1500 cells/well), stimulated with IL-1α (10 ng/ml) were treated with increasing amounts of IL-28A or IL-28B in culture for 7 days. Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

Cell viability was measured with PrestoBlue. The data is representative of one out of two different fibroblast batches.

FIG. 14: Effect of IL-28A, IL-28B and IL-29 in a Kidney RPTEC-fibroblast co-culture ECM in vitro model Human primary renal proximal tubular epithelial cells (RPTECs) were placed in co-culture with primary human kidney fibroblasts (in a ratio of 1:1 with a final seeding cell concentration of 2000 cells/well) and treated with IL-29, IL-28A or IL-28B for 7 days. Cells were removed & the ECM proteins, Fibronectin, and Collagen I&III were measured by immunofluorescent labelling with imaging and quantification on a Cellomics Arrayscan. Data represents Mean Total Intensity plotted as Mean+/−SD of 4 separate wells. Cell viability was measured with PrestoBlue. IL-29, IL-28A or IL-28B were either added to the co-culture of RPTECs and fibroblasts at day 0 (FIG. 14(a)), or added to the RPTECs for 24 hours before combination with the fibroblasts (FIG. 14(b)) or added to the fibroblasts for 24 hours before combination with the RPTECs (FIG. 14(c)).

FIG. 15: Comparison of addition formats on the effect of IL-28A, IL-28B and IL-29 in the Kidney RPTEC-fibroblast co-culture ECM in vitro model The data presented in FIG. 14 was re-plotted showing the effect of IL-28A, IL-28B and IL-29 in the kidney co-culture cell system using the 3 different addition protocols in the one graph, where IL-28A, IL-28B or IL-29 were added to the co-culture of RPTECs and HRFs together (termed Co-culture), to the RPTECs first and 24 hours later the HRFs were introduced (termed RPTEC added 1$^{st}$) and to the HRFs first and 24 hours later the RPTECs were introduced (termed HRF added 1$^{st}$) and the co-culture was continued for 7 days with fibronectin and collagens I&III data re-plotted in FIGS. 15 (a) and (b), respectively. The ECM markers were analysed, for each cytokine, using analysis of variance accounting for differences between order of addition (co-culture, RPTEC first and HRF first) and doses (0 to 10000 ng/ml). Post-analysis comparisons were performed and a Bonferroni correction used to adjust the reported p-values. All analyses were performed using SAS v9.4 (SAS Institute). The doses of cytokine reaching significance are marked on the graphs with **$p<0.0001$, *$p<0.001$, **$p<0.01$ and *$p<0.05$.

FIG. 16: High content images showing the effect of IL-28A, IL-28B and IL-29 in the Kidney RPTEC-fibroblast co-culture ECM Human primary renal proximal tubular cells (RPTECs) in co-culture with primary human kidney fibroblasts (in a ratio of 1:1 with a final cell concentration of 2000 cells/well at seeding) were cultured alone (control) or treated with IL-29, IL-28A or IL-28B at 1000, 100 or 10 ng/ml for 7 days. Cytokines were added to the RPTECs 24 hours before the inclusion of the fibroblasts in the culture as depicted in FIG. 14(b). Images shown are from 1 representative field out of a total of 16 fields for each condition. Magnification was performed with a ×10 objective.

FIG. 17: Effect of IL-28A and IL-28B in a Lung SAEpithelial-fibroblast co-culture ECM in vitro model Primary human small airway lung epithelial cells (SAEpithelial) in co-culture with human IPF primary lung fibroblasts (1:1 ratio at a final cell concentration of 2000 cells/well at seeding) were treated with IL-28A or IL-28B for 7 days. Cells were removed & the ECM proteins, Fibronectin, Collagen I&III and Collagen IV were measured by immunofluorescent labelling while total ECM protein was identified by flamingo pink staining. Imaging and quantification was performed on a Cellomics Arrayscan. Data represents Mean Total Intensity plotted as Mean+/−SD of 4 separate wells. Cell viability was measured with PrestoBlue with a read-out on fluorescence.

FIG. 18: Protein and DNA sequences of IFNL1, IFNL2, IFNL3 and IFNL4 The protein sequences of IFNL1, IFNL2, IFNL3 and IFNL4 were obtained from Uniprot database and DNA sequences of IFNL1, IFNL2, IFNL3 and IFNL4 were from GenBank.

FIG. 19: Effect of IL-28A and IL-29 in an in vitro Human Liver stellate and epithelial cell co-culture model of hepatic fibrosis Human primary stellate cells and primary intrahepatic biliary epithelial cells were placed in co-culture at 1000 cells/well (1:1 ratio), and treated with IL-28A or IL-29 for 5 days. Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

The protein sequences of IFNL1 (SEQ ID NO: 1), IFNL2 (SEQ ID NO: 3), IFNL3 (SEQ ID NO: 5) and IFNL4 (SEQ ID NO: 7) were obtained from Uniprot database and DNA sequences of IFNL1 (SEQ ID NO: 2), IFNL2 (SEQ ID NO: 4), IFNL3 (SEQ ID NO: 6) and IFNL4 (SEQ ID NO: 8 were from GenBank.

FIG. 20: Effect of IL-28A on podocyte survival in an in vitro 3D Glomerular spheroid model of Glomeruolosclerosis (a) 3D glomerular spheroids were constructed from an inner core of human glomerular endothelial cells surrounded by GFP-labelled human podocytes. (b) The spheroids were either grown in media or treated with focal segmental glomerular sclerosis (FSGS) patient plasma at a 15% final concentration plus or minus the presence of human IL-28A protein. In each experiment and for each condition, at least 5 spheroids were imaged. (c) The 2D maximum intensity projections (MIPs) of these spheroids were then analysed using Definiens image analysis to define marker areas above threshold intensity in the green channel under the different culture conditions which was plotted as cell marker area as a proportion of total spheroid area. 7% of podocytes were GFP labelled FIG. 21: Hydrodynamic Transfection of mouse IL-28B protects against fibrosis in the mouse unilateral ureteral obstruction (UUO) kidney fibrosis model Mice were either UUO operated (UUO operated control HDT, n=10), non-operated (non-op, n=5), UUO operated but treated with IL-28B at day-1 for prophylactic dosing (IL-28B HDT Day-1, n=10) or treated with IL-28B at day 7 for therapeutic dosing (IL-28B HDT Day 7, n=10) and all animals were terminated at day 21, kidneys removed, fixed in NBF, paraffin-embedded, sectioned, and stained with picro-sirius red (PSR). The slides were then imaged with a Hamamatsu slide scanner. Representative images of the PSR-stained kidneys sections are shown in FIG. 21(a) for 1 normal mouse, 2 UUO operated control mice, 2 UUO operated and treated with IL-28B at Day-1 mice or 2 UUO operated and treated with IL-28B at Day 7 mice, by hydrodynamic transfection. All the terminal mice kidney sections (5× non-operated, 10×UUO control, 10×UUO IL-28B at Day-1 and 10×UUO IL-28B-treated mice at Day 7) were imaged and the total area covered by the PSR stain was estimated using the Definiens image analyses platform reading out on total stained area (FIG. 21(b)) or high intensity stained area (FIG. 21 (c)). The % collagen area is shown as mean+/−SEM with treatment groups compared to SEAP control using Dunnet's multiple comparison test; =p<0.01, *p<0.001 and ****=P<0.0001. SEAP=secreted alkaline phosphatase control protein FIG. 22: Effect of IL-29 in an in vitro Human Kidney renal proximal tubular epithelial cell mono-culture model of kidney fibrosis Human primary renal proximal tubular epithelial cells were placed in co-culture at 2000 cells/well and treated with IL-29 for 5 days. Cells were removed & the ECM proteins, Fibronectin, Collagen I&III and Collagen IV were measured by immunofluorescent labelling with imaging and quantification on a Cellomics Arrayscan. Data represents Mean Total Intensity plotted as Mean+/−SD of 4 separate wells.

FIG. 23: Treatment with human IL-29 by hydrodynamic transfection protects against tubulointerstitial fibrosis in the mouse unilateral ureteral obstruction model of kidney fibrosis C57Bl1/6 mice were subjected to hydrodynamic transfection with a control vector containing SEAP (n=10) or a vector containing a human IL-29 construct (n=9). 24 hours post transfection mice were subjected to unilateral ureteric obstruction (UUO) of the left kidney or mice were non-operated (n=4). After 7 days the hydrodynamic transfections were repeated and the animals culled at 19 days post UUO. FIG. 23(a); Sera samples were taken from the mice at day 0 (24 hours post transfection) and again at 19 days and analysed for human IL-29 protein. Human IL-29 levels were plotted comparing IL-29 levels in the Day 0 UUO IL-29 group, terminal D19 UUO SEAP group and the terminal UUO IL-29 group.

Kidneys were recovered fixed in NBF, paraffin-embedded, sectioned and stained with picro-sirius red (PSR) and the slides were then imaged with a Hamamatsu slide scanner. FIG. 23(b) shows representative images from a normal kidney, a UUO kidney transfected with either control SEAP containing vector or human IL-29 containing vector as shown at 100× (top line) and 200× (bottom line) magnification. All the terminal mice kidney sections (4× non-operated, 10×UUO SEAP control, 9×UUO IL-29 at Day-1) were imaged and the total area covered by the PSR stain was estimated using the Definiens image analyses platform reading out on total stained area (FIG. 23(c)). The % collagen area is shown as mean+/−SEM with the IL-29 treatment group compared to UUO+SEAP control group using uncorrected Fisher's LSD comparison test; **=p<0.01.

SEAP=secreted alkaline phosphatase control protein

REFERENCES

Adair J. R. and Lawson A. D. G., 2005, Drug Design Reviews—Online 2(3): 209-217.
Andersen H., et al., 2013, Journal of Clinical and Translational Hepatology 1: 116-124.
Andreakos et al 2017, Frontiers in Immunology, 8, article1232.
Bach et al., 1997, Ann Rev. Immunol. 15:563-591.
Bhushal et al 2017, Frontiers in Immunology, 8, article 671.
Biron et al., 2001, Immunity 14(6): 661-664
Blazek et al., 2015, J Exp Med 212(6): 845-853.
Blumer et al 2017, J. Biol. Chem. 292(43) 17928-17938.
Bochud et al., 2012, Hepatology 5(2):384-394
Broggi et al 2017, Nature Immunology, 18(10), 1084-1093
Chow & Gale 2015, Cell 163(7), 1808-1808.e1
Chapman A., et al., 2002, Advanced Drug Delivery Reviews 54: 531-545.
Chiriac et al 2017, Gastroenterology, 153, 123-138
Doyle et al., 2006, Hepatology 44(4): 896-906.
Eslam and George, 2015, Semin Liver Dis. 35:402-420.
Eslam et al., 2015, Nature Communications 6: 6422-6432.
Gad et al., 2009, Journal Biological Chemistry 284(31): 20869-20875.
Ge et al., 2009, Nature 461(7262):399-401.
Gresser, 2015, Biomed Pharmacother. 71:29.
Griffiths S. J. et al., 2013, PLoS Pathog. 9: e1003514.
Guenterberg et al., 2010, Molecular Cancer Therapeutics 9(2):510-520.
Guo et al., 2013, PLoS One 8(10): e77911.
Hemann et al 2017, Nature Immunology, 18(10), 1061-1062
Holliger P. and Hudson P. J., 2005, Nature Biotech. 23(9): 1126-1136.
Hong et al., 2016, Journal of Experimental Medicine 10:1084-1098.
Huang et al., 1993, Science 259(5102):1742-1745.
Kanefuji et al. 2014, Molecular Therapy—Methods & Clinical Development (2014) 1, 14029.
Kotenko, 2002, Cytokine Growth Factor Rev 13(3):223-240.
Kotenko et al, 2003, Nature Immunology 4(1): 69-77
Koltsida et al., 2011, EMBO Molecular Medicine 3(6): 348-361.
Li et al., 2010, European Journal of Cancer 46(1):180-190.
Liu et al., 1999, Gene Therapy 6, 1258-1266.
Mahlakoiv T. et al., 2015, PLoS Pathog. 11: e1004782.
McFarland et al., 2014, Nature Immunology 15: 72-79.
Miknis et al., 2010, Journal of Molecular Biology 404:650-664.
Mordstein M. et al., 2008, PLoS Pathog. 4: e1 000151
Numasaki et al., 2007, Journal Immunology 178(8): 5086-5098.
Osterlund et al., 2007, Journal Immunology 179: 3434-3442.
Park et al., 2012, Hepatology 56(6): 2060-2070.
Pott J. et al., 2011, Proc. Natl. Acad. Sci. 108: 7944-7949.
Prokunina-Olsson et al., 2013, Nature Genetics 45(2): 164-171.
Rallon et al., 2010, Aids 24(8): F23-29.
Stahl et al., 1993, Cell 74: 587-590.
Sato et al., 2006, Journal Immunology 176(12):7686-7694.
Steen et al., 2010, Journal Interferon Cytokine Research 30(8): 597-602.
Sheppard et al., 2003, Nature Immunology 4(1):63-68.
Souza-Fonseca-Guimaraes et al., 2015, Proc. Natl. Acad. Sci. 112: E2376-E2384.
Suppiah et al., 2009, Nature Genetics 41(10): 1100-1104.
Tanaka et al., 2009, Nature Genetics 41 (10):1105-1109.
Thomas et al., 2012, Gastroenterology 142 (4): 978-988.
Verma R., et al., 1998, Journal of Immunological Methods, 216: 165-181.
Wack et al 2015, Nature Immunology, 16(8), 802-809
Wolk et al., 2013, Science Translational Medicine 5(204): 204ra129.
Zhou et al., 2007, Journal of Virology, 81: 7749-7758.
Zitzmann et al., 2006, Biochem. Biophys. Res. Commun. 344(4):1334-1341.
WO1992/022853.
WO2005/003169.
WO2005/003170.
WO2005/003171.
WO2005/113605.
WO2009/040562.

EXAMPLES

Summary

Cytokines of the interferon-k (IFN-λ) family, known as IFN-λ1 (IL-29), IFN-λ2 (IL-28A) and IFN-λ3 (IL-28B), signal through a distinct receptor complex, composed of the IFN-λR1 (IL-28R1) and interleukin-10R2 (IL-10R2) receptor chains.

Using a hydrodynamic transfection in vivo screen in the mouse Adriamycin-induced model of chronic kidney disease (CKD), IFN-λ2 and IFN-λ3 were reported as hits. A hit was called based on the level of kidney fibrosis as determined by a 40% reduction in renal hydroxyproline levels (renal collagen). Both IFN-λ2 and IFN-λ3 also showed a corresponding preservation of renal function as measured by serum creatinine. This led conditional survival rates (ie. not reaching end stage kidney failure) to increase from 50% at 49 days post Adriamycin in saline transfected mice, to 85% when transfected with IFN-λ2, and 100% with IFN-λ3 To validate this anti-fibrotic effect in an alternative model of CKD with a different stimulus, both IFN-λ1 and IFN-λ3- were applied by hydrodynamic transfection in the Unilateral Ureteral Obstruction (UUO) induced kidney fibrosis model of chronic kidney disease, with both giving protection against tubulointerstitial fibrosis.

The anti-fibrotic effect of the IL-28R1 ligands has been confirmed in several human primary cell in vitro models of fibrosis that read out on mature accumulated extracellular matrix (ECM) protein. Recombinant human IFN-λ1, IFN-λ2 and IFN-λ3 each inhibited the accumulation of the fibrosis-associated ECM proteins (fibronectin and collagens I, III and IV) in primary human cell in vitro models of liver, lung, gut, skin and kidney fibrosis. This is seen in several models including liver stellate cells, liver stellate-hepatocyte co-cultures (both basal matrix and TGFβ-induced), liver stellate-epithelial cell co-cultures, TGFβ-induced small intestinal fibroblasts, IL-1α-induced dermal fibroblasts, keratinocyte-dermal fibroblast co-cultures, renal proximal tubular epithelial cell-kidney fibroblast co- and mono-cultures and lung small airway epithelial-IPF lung fibroblast co-cultures. In a more complex glomerular organoid model of glomerulosclerosis, application of plasma from a patient with relapsing nephrotic syndrome caused both a loss of podocyte number and retraction of processes and pedicels in a manner consistent with podocyte effacement and loss seen in many glomerular diseases that lead to glomerulosclerosis and renal fibrosis. Application of recombinant IFN-λ2 in this model totally prevented changes to the podocytes caused by this patient plasma.

The IL-28R1 ligands have been shown to have potent anti-fibrotic effects in both in vitro and in vivo fibrosis screens. Potent effects have been described in in vivo mouse models of renal fibrosis and in numerous in vitro human fibrosis models with relevant primary cells from liver, small intestine, skin, kidney and lung organ systems. These proteins therefore have unexpected potential as anti-fibrotic agents in multiple types of fibrosis.

Methods

Mouse In Vivo

Effect of IL-28A and IL-28B in Adriamycin-Induced Kidney Fibrosis Model of Chronic Kidney Disease (CKD)

Female Balb/c mice, at least 6 weeks old and a weight greater than 24 g, were subjected to an IV injection through the tail vein of cDNA (or pair of cDNA for paired studies) in an appropriate hydrodynamic transfection expression vector. After 7 days the mice were given adriamycin (doxorubicin) at 11 mg/kg IP and monitored for 49 days. Mice were monitored every day for weight and health; those mice that had lost greater than 40% of starting body weight or showing physical signs of end stage kidney failure were terminated and the data collected. At the end of the 49 day study period, all mice were terminated and kidneys and sera collected for analyses. Kidney hydroxyproline was measured using the QuickZyme assay method (QuickZyme Biosciences) and serum creatinine was measured using the three enzyme method and read out as μg/ml serum creatinine. Kidney fibrosis (hydroxyproline) in the saline plus adriamycin group, marked as "Saline" on the graphs, was considered to be a maximum disease response. This was set at 100% and used to normalize across the treatment groups. Naïve animals received no adriamycin and each screen experiment contained a "HGF" group which received adriamycin and the cDNA for HGF. HGF was used as an anti-fibrotic positive control, with a >40% reduction in hydroxyproline used for quality control.

Effect of IL-28 and IL-29 in Mouse Unilateral Ureteral Obstruction-Induced Kidney Fibrosis Model DNA construction for hydrodynamic transfection of mouse IL28B and human IL29

A DNA construct for hydrodynamic transfection was created by insertion of the DNA sequence (NM_172140.1) encoding the human IL29 precursor protein (NP_742152.1) into the pLive vector (Mir5420, Mirus Bio LLC, 545 Science Dr., Madison, WI 53711 USA) using NheI-XhoI restriction digestion followed by DNA ligation of homologous ends. A gene (mRNA Ref Seq NM_177396) construct encoding mouse IFNL3 (NP_796370) was cloned into pLive (Mirus) using a BamHI-XhoI restriction digestion strategy of both vector and insert followed by ligation. Gene insertions into pLive were verified by DNA sequencing. The gene was preceded by a CCACC sequence directly up steam of the ATG encoding the start methionine of the signal sequence. This vector harbours a kanamycin resistance gene and a pUC origin that allow for DNA amplification in *Escherichia coli*. Furthermore, this vector harbours mouse minimal albumin promoter to transcribe the human IFNL-1 gene flanked by introns on either side. [The pLive vector allows for long term protein expression in the liver].

The DNA construct for hydrodynamic transfection was isolated from *Escherichia coli* culture harbouring this construct using a plasmid isolation kit that limits the amount of endotoxin in the solution (HiSpeed Plasmid Giga EF, Qiagen). Plasmid DNA was Sanger sequenced to verify the insert.

Kanefuji et al. and Liu et al. describe typical vectors for hydrodynamic transfection.

Expression of Proteins by Hydrodynamic Transfection (HDT)

Mice were hydrodynamically transfected with 50 μg of either the pLIVE-human IL-29, pLIVE-mouse IL-28B or pLIVE SEAP Vector (Mirus Bio, Cat #MIR 5320) in TransIT-EE vehicle. The solution containing the vector was injected rapidly (less than 2.5 seconds) intravenously in a volume of 2 ml. General anaesthesia with Isoflurane was induced prior to hydrodynamic injection and maintained for at least 1 minute post injection.

Quantitation of Mouse IL-28B and Human IL-29 from Mouse Sera

Mouse IL-28B was quantitated using a meso scale discovery (MSD) quantitation assay using commercial antibody pairs (RnD systems, cat #DY1598B) and mouse sera was diluted 1 in 100 to place on the linear standard curve. Human IL-29 was quantitated using the MSD U-plex human IL-29 antibody set (cat #B21WD) and mouse sera was diluted 1 in 100 to place in the linear range.

Unilateral Ureteral Obstruction (UUO) Induced Kidney Fibrosis Model of Chronic Kidney Disease Male C57BL/6 mice (Charles River) weighing at least 19 g were subjected to a Unilateral Ureteral Obstruction (UUO) induced kidney fibrosis model of chronic kidney disease.

Surgery was performed using Isoflurane induced general anaesthesia and under aseptic conditions as appropriate for surgical techniques. Mice underwent laparotomy followed by tying off the left ureter using 3.0 Mersilk ligature. The muscle wall was sealed using 5-0 Vicryl in a continuous pattern, with the skin being closed by subcuticular stitching using 5-0 Vicryl. Appropriate analgesia was administered pre-surgery and post-surgery. Blood samples were taken at appropriate times as detailed in the results. Mice were restrained using a recognised mouse restrainer and 30 µl of blood was taken from the tail vein via the tail prick method, using a pipette to accurately measure the blood sample. This sample was placed in a 0.2 ml PCR tube (Thermo) and spun down (20,000 g, 5 minutes) to take off as much serum as possible, which was placed in a fresh PCR tube and stored at −80° C.

On Day 19 or 21 mice were anaesthetised using Isoflurane, blood removed by cardiac puncture into serum tubes (Sarstedt) and the mice killed by cervical dislocation. The left kidney was removed and two quarters snap frozen in liquid nitrogen and stored at −80° C. The remaining half was placed into 10% neutral buffered formalin, dehydrated in a tissue processor and paraffin embedded for histological analysis. Paraffin blocks were sectioned at 4 µm on a microtome and mounted on glass slides. Slides were then de-waxed and hydrated, stained with picro-sirius red (PSR) before being washed with acidified water. Slides were then dehydrated, cleared and coverslipped. Slides were left to dry and then scanned using a Hamamatsu slide scanner.

Whole slide images were imported into Definiens Developer XD 64 and analysed using the bright-field module. Briefly, cortex areas were manually annotated to remove the medulla from analysis. Marker threshold levels (e.g. PSR stain) were determined for the individual markers on a training data set of no fewer than four images. The analysis algorithm was then run on a dedicated server to determine marker areas above threshold intensity for each individual marker and the area of each marker above the threshold intensity was determined as a proportion of the area of the cortex.

Histological assessment of the level of fibrosis was performed by blinded researchers with expertise in the field of renal fibrosis using a combination of Pico Sirius red, Masson's Trichrome and Haematoxylin and Eosin stained sections as preferred. A 10 point scale was used where 10 was very severe fibrosis equivalent to end stage renal failure and 1 normal. Parameters assessed in the score were tubular basement membrane expansion, epithelial cell flattening, brush border integrity, tubular atrophy and collapse, tubular lumen size, interstitial cell infiltrate, glomerular tuft structure, mesangial expansion, glomerular infiltrate, glomerular urinary space, glomerular basement membrane and mesangial matrix expansion.

The Definiens image analyses and the histological assessment of images also applies to the Adriamycin-treated kidney sections.

Human In Vitro Extracellular Matrix Fibrosis Assay Measurements a) Cell Culture

All extracellular matrix (ECM) accumulation assays were performed in 384-well black clear-bottomed plates (Greiner cat #781090), where the media, cell number/well, incubation time and stimulus varied with the primary cell type used.

Human Hepatic Stellate Cells (HHSteC) (ScienCell, Cat. number sc-5300) (at passage 4) and Human Intrahepatic Biliary Epithelial Cells (ScienCell, Catalogue Number sc-5100) (at passage 3) co-culture were seeded at 1000 cells/well (1:1 ratio) in 25 uL of Epithelial Cell Medium—phenol red free (EpiCM-prf) with supplements (ScienCell, Catalogue Number sc-sc-4101-prf). Human stellate cells (ScienCell) in mono-culture were seeded at 1000 cells/well in stellate cell media (ScienCell) and human stellate cells and hepatocytes (ScienCell) co-culture at 1000 cells/well (1:1 ratio) in the mixed culture media (ScienCell).

Human small intestine fibroblasts (ScienCell) were seeded at 2000 cells/well in renal epithelial cell basal media+0.5% FCS and supplements (ATCC).

Human dermal skin fibroblasts were grown in fibroblast growth media and human keratinocytes were grown in keratinocyte media and seeded at 1500 cells/well. The fibroblast-keratinocyte co-culture (9:1 ratio) was grown in a 1:1 mixture of media and seeded at 1500 cells/well.

Human renal proximal tubular epithelial cells (RPTEC, Innoprot) and human renal fibroblasts (HRF, InnoProt) were seeded at 2000 cells per well (ratio 1:1) in co-culture using renal epithelial cell basal medium (ATCC)+0.5% FCS and supplements (ATCC).

Human small airway epithelial cells (ATCC) were grown in basal growth media plus bronchial epithelial growth kit supplements (ATCC) and IPF134 lung fibroblasts (ATCC) were grown in fibroblast growth media (Lonza). The co-culture was seeded at 2000 cells/well (1:1 ratio).

b) Measurement of Cell Growth

After 7 days incubation at 37° C., 5% $CO_2$, cell growth was assessed using PrestoBlue® Cell Viability reagent (Thermo Fischer Scientific) following the instructions of the manufacturer.

c) Measurement of ECM Accumulation Measurement of individual ECM components: Immunofluorescence After 7 days incubation at 37° C. in 5% $CO_2$, cells were washed in PBS and lysed with 20 µl/well of 0.25 M $NH_4OH$/25 mM Tris (Sigma-Aldrich) for 15 min at 37° C. Matrix was then washed 3 times in PBS, fixed in 40 µl 100% methanol for 30 min at −20° C. and washed 3 times in PBS before being stained using anti-Fibronectin (eBiosciences), anti-Collagen I (Millipore), anti-Collagen III (Millipore), anti-Collagen IV (eBiosciences) and anti-Collagen V (Abcam) antibodies. Plates were scanned on the Arrayscan HC reader (Cellomics) using a 3-channel protocol under the "Cellomics CellHealth" profiling bioapplication and a 10× objective (new ×1 camera) with 2×2 binning ($1·10^4 \times 1·10^4$ pixels/field).

Measurement of Total ECM Components: Flamingo™ Staining

Immunofluorescence plates were washed 3 times in Flowfusor water before being stained using Flamingo™ fluorescent gel stain reagent (BioRad) following the instructions of the manufacturer. Plates were scanned on the Arrayscan HC reader (Cellomics) using a 2-channel protocol under the "Cellomics CellHealth" profiling bioapplication and a 10× objective (new ×1 camera) with 2×2 binning ($1·10^4 \times 1·10^1$ pixels/field).

Method for Generation of 3D Human Glomerular Spheroid

Spheroid Generation and Treatment

Nano-shuttle-PL (Cat #657841) was added to T75 flasks of stably transfected GFP-tagged actin, conditionally immortalised SV40 infected podocytes and human glomerular endothelial cells (HRGECs) provided by the University of Bristol, grown in RPMI 1640 (10% FCS, 5 ML L-glutamine and 1×ITS, Gibco) and EBM-2 media, with supplement kit from Lonza (Cat #CC4147), respectively. GFP transfected podocytes were confirmed by FACS. All cells were harvested using TrypLE Express (Gibco) and magnetised HRGECs were seeded at 5000 cells/well in 96-well low adhesion Greiner plates (Cat #655976). A Greiner Spheroid Drive (Cat #655830) was placed beneath the 96-well plate for 6h and spheroids were grown in EBM-2 media at 37° C./5% $CO_2$/100% humidity. The Drive was removed, and magnetised GFP-podocytes were seeded at 5000 cells/well. The Drive was returned beneath overnight and spheroids were differentiated for 10 days feeding every 3 days using the Holding Drive. Spheroids were then treated with human FSGS plasma at 15% final concentration, plus or minus IL-28A (10,000 ng/mL), or media only for 7 days.

Fixation and Staining

Spheroids were fixed and permeabilised for 3 hours at 4° C. in 10% formalin/1% Triton X-100/PBS. After 3×10 min PBS washes spheroids were dehydrated in ascending series of methanol at 4° C. in PBS: 25%, 50%, 75%, 95% for 30 mins each and left in 100% methanol overnight. Spheroids were rehydrated in the same descending series and washed as before in PBS before blocking in PBST (0.1% Triton X-100 in PBS) containing 3% BSA overnight at 4° C. After 4×30 min PBST washes, secondary antibodies (1:500/PBST: Alexa GAR-AF647 and GAM-AF555) were added. To enhance the GFP signal, anti-GFP-AF488 was added at 1:200 for 24h. Spheroids were washed (4×30 mins/PBST) before image capture using the YokoGawa confocal quantification 1 (CQ1) at ×20 magnification.

Podocyte Cell-Marker Area Quantification

Maximum intensity projections were imported into Definiens Developer XD 64 and analysed using the immunofluorescence module. Spheroid areas were manually annotated and marker threshold levels were determined for the individual markers and an analysis algorithm was run to determine marker areas above threshold intensity for each marker. The area of each marker above the threshold intensity was determined as a proportion of the area of the spheroid.

Results (1) Mouse Adriamycin-Induced Model of Chronic Kidney Disease (CKD)

Mouse IL-28A (IFNL2) was identified in a screen for fibrosis modifying proteins in the mouse Adriamycin CKD model initially as one member of a hydrodynamically transfected cDNA pair (n=15 mice). The transfected pair reduced kidney fibrosis as measured by total renal hydroxyproline by 51% relative to a saline transfection control group (p=0.02) (FIGS. 1(a) and (b)) and normalised kidney function based on serum creatinine levels (p<0.05) (FIG. 1(c)). The anti-fibrotic effects of IL-28A were confirmed in a repeat study, transfecting the IL-28A cDNA independently in the same model (n=22 mice per group). IL-28A reduced kidney fibrosis as measured by total renal hydroxyproline by 48% relative to the saline control group (p=0.0004) (FIGS. 2(a) and (b)), while the loss of kidney function was returned to the normal range, as measured by serum creatinine. (Mean serum creatinine=1 μg/ml in the IL-28A group compared to 4.8 μg/ml in the untreated Adriamycin saline control group (p<0.0001); mean naïve group serum creatinine=0.8 μg/ml) (FIG. 2(c)). Conditional survival as measured by symptoms of end stage kidney failure increased from 50% in the saline treated Adriamycin group to 85% in those transfected with mouse IL-28A (FIG. 2(d)). At 49 days, all kidneys from surviving mice ((naïve (n=8), untreated Adriamycin animals (n=20) and the IL-28A hydrodynamically transfected animals (n=19)) were fixed, paraffin-embedded, sectioned and stained with either masson's trichrome (MT) or picosirius red (PSR) and imaged on a Hamamatsu slide scanner. Exemplar and representative images of the PSR-stained kidneys for one naïve, three untreated Adriamycin and three IL-28B-treated Adriamycin animals are shown in FIG. 5(f). Adriamycin treatment has caused about 50% of the glomeruli to exhibit clear glomerulosclerosis with enhanced PSR staining predominently in the glomerular basement membrane, but also in the mesangial matrix. In the tubulonterstitium there is consistent tubular basement membrane expansion in greater than 70% of the cortex with a large number of tubules exhibiting flattened epithelia causing a significant loss of tubular architecture with huge distension of the tubule leading to large lumen with no brush border. These areas have mild to moderate cell infiltration.

Application of IL-28A has almost completely prevented signs of glomerulosclerosis with little evidence of glomerular basement membrane thickening. Only 2 of the 22 animals showed notable signs of epithelial flattening and the lumen expansion characteristic of untreated animals. The remainder of the animals had a tubulointerstitium that appeared near normal in greater than 80% of the cortex with little effect of the tubular basement membrane.

Figure 5B:
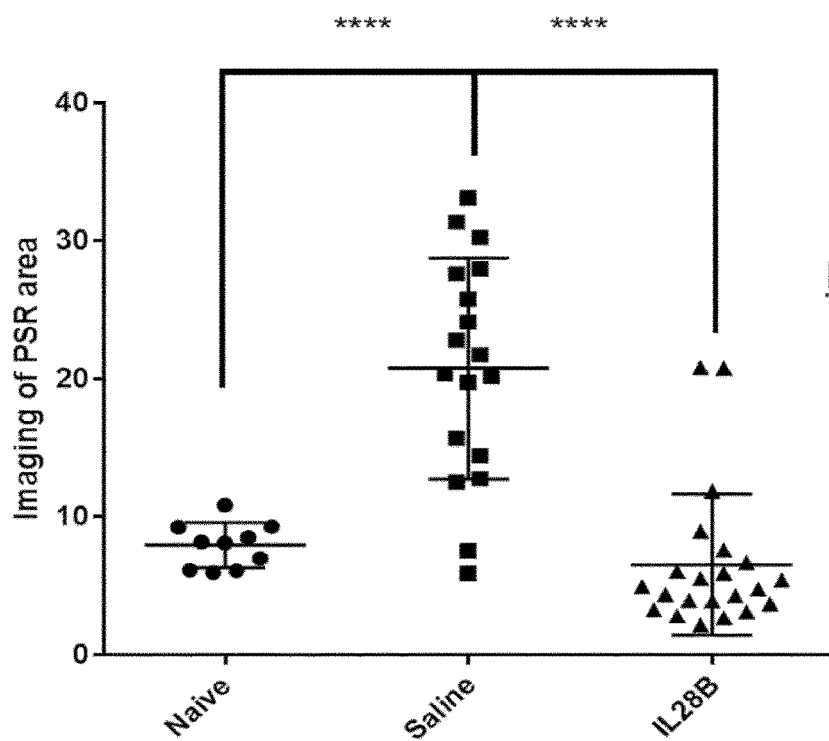
Figure 5C:
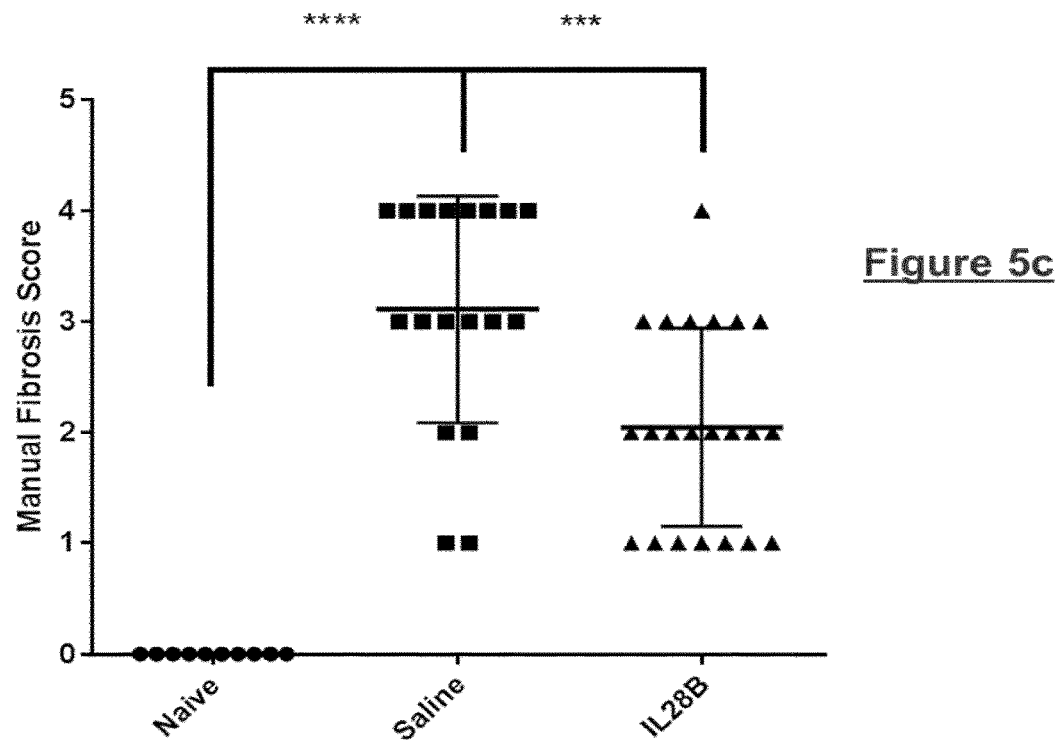
Figure 5D:
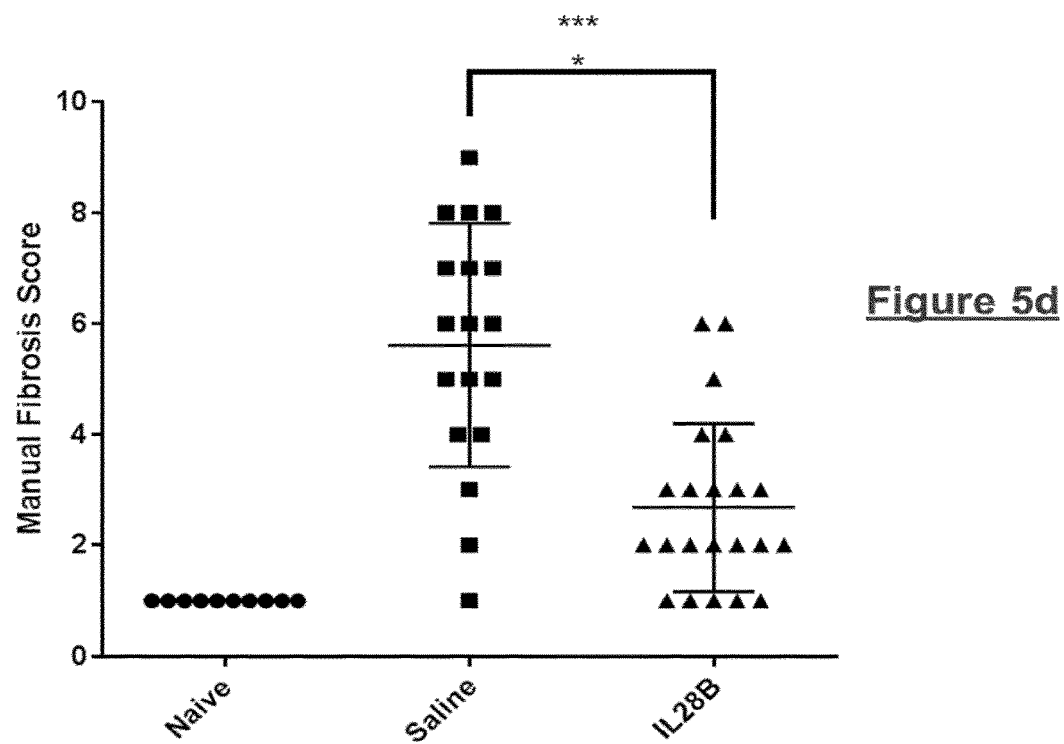
Figure 5E:
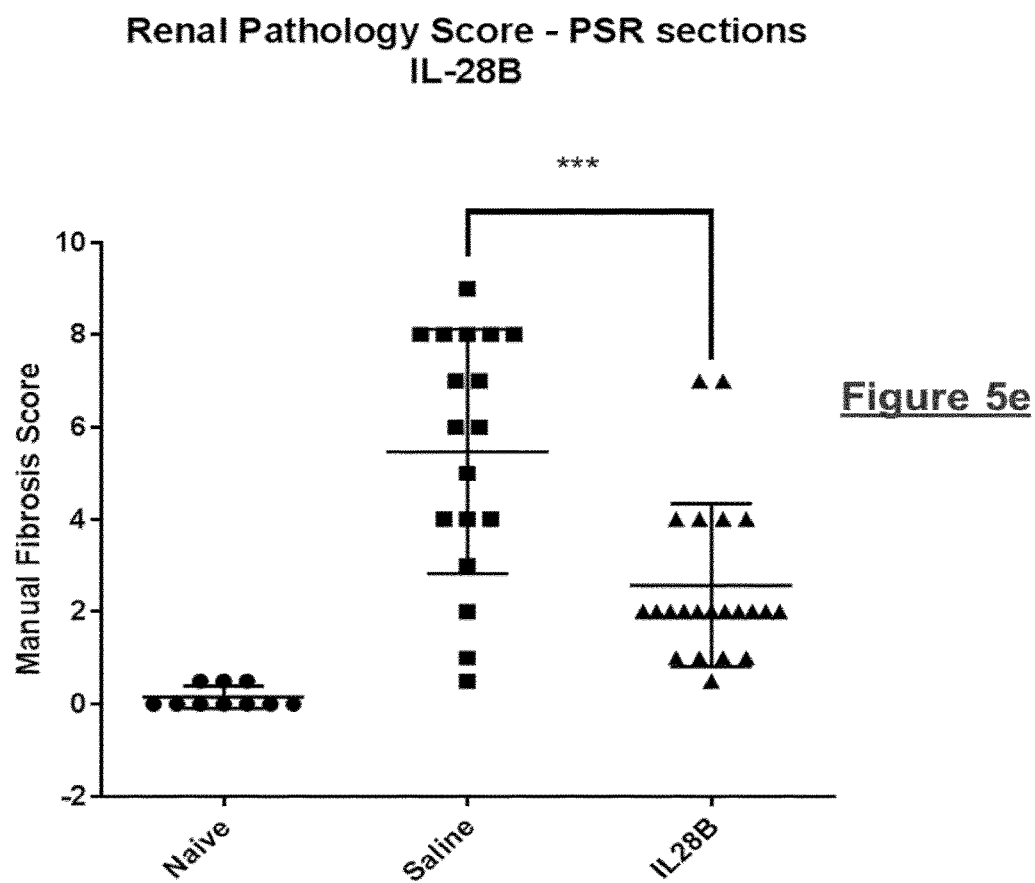
Figure 5G:
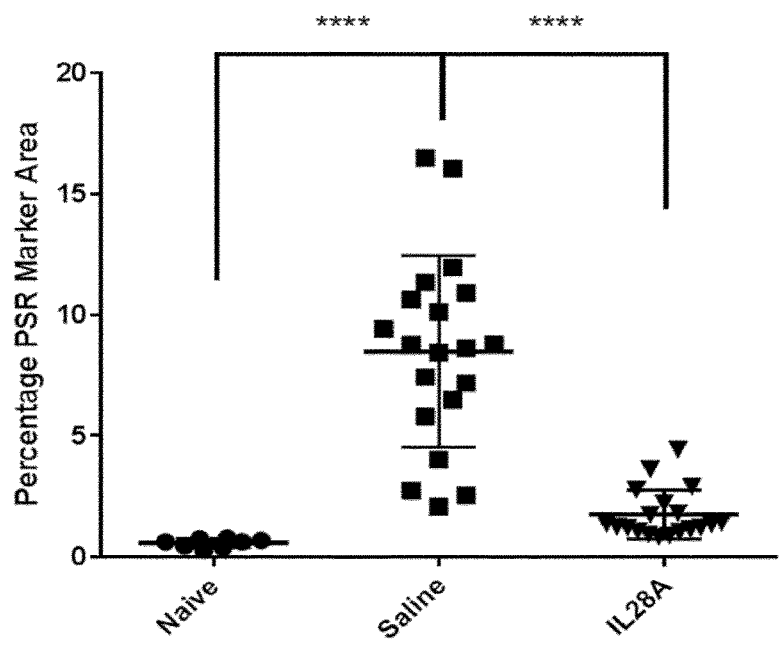
Figure 5H:
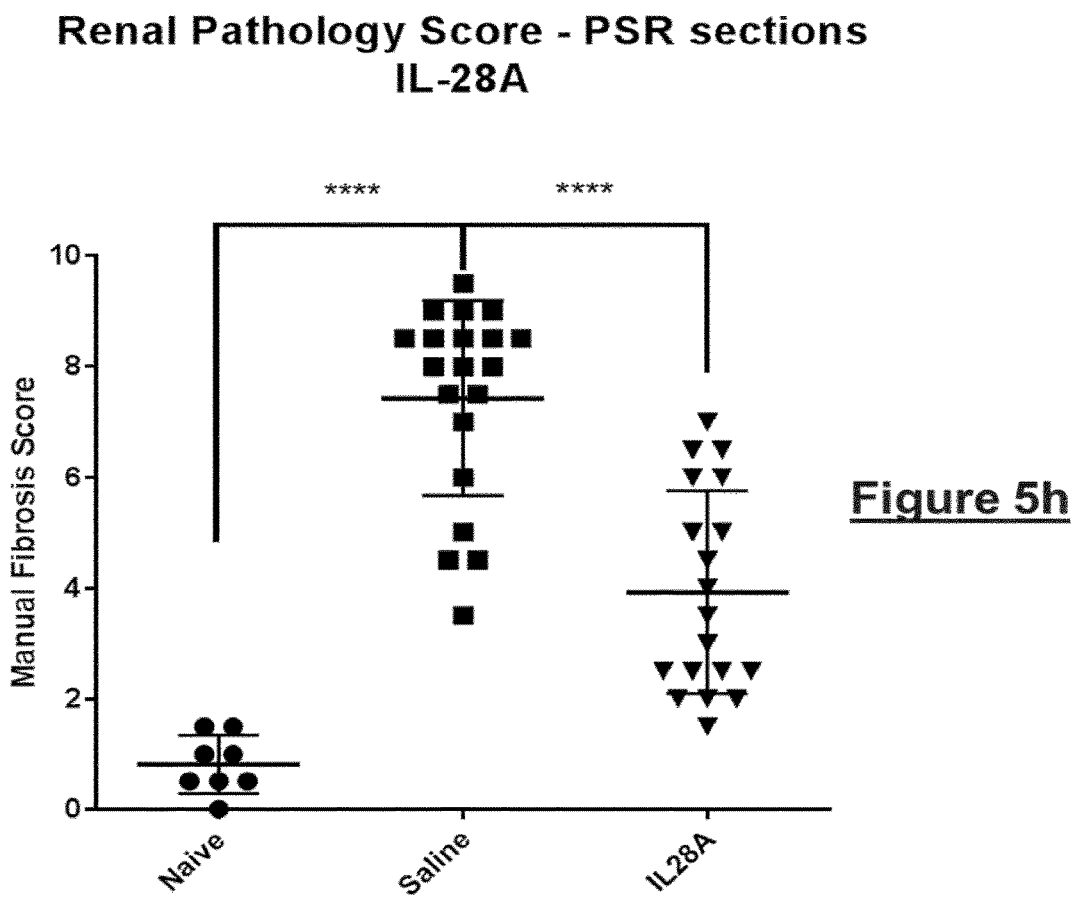
Figure 5I:
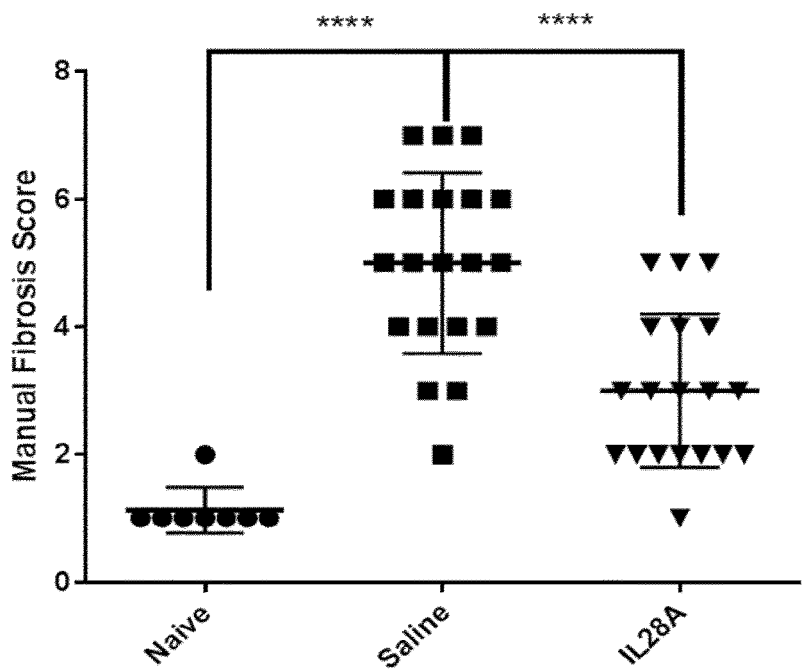

The 47 mouse kidney samples that were stained with PSR were subjected to high content image analysis using Definiens software and the area of PSR staining measured in the three groups was plotted as percentage PSR stained area (FIG. 5(g)). The same 47 mouse kidney slides were subjected to a blinded pathological assessment of the degree of fibrosis by two individuals with renal pathology expertise. A renal scientific expert scored the PSR-stained slides using a scoring range from 0-10 point scale (0 showing no fibrosis, and 10 the highest fibrosis). IL-28A treatment showed a significant 47% reduction in the pathology score (p<0.0001) compared to the untreated group (FIG. 5(h)). A second renal scientific expert manually scored the 47 MT-stained slides using a 1-10 scale (1 showing no fibrosis and 10 the highest). The IL-28A-treated group again demonstrated a clear improvement in the level of fibrotic remodelling (p<0.0001) relative to the untreated group (FIG. 5(i).

Mouse IL-28B (IFNL3) was also identified in a screen for fibrosis modifying proteins in the mouse Adriamycin CKD model initially as one member of a hydrodynamically transfected cDNA pair (n=15 mice per group). The transfected pair reduced kidney fibrosis as measured by total renal hydroxyproline by 59% relative to the saline transfection control group (p=0.00086) (FIGS. 3(a) and (b)) and normalised kidney function based on serum creatinine levels (non-significant) (FIG. 3(c)). The anti-fibrotic effects of IL-28B were confirmed in a repeat study, transfecting the IL-28B cDNA independently in the same model (n=22 mice per group). Kidney fibrosis as measured by total renal hydroxyproline was reduced by 65% relative to the saline control group (p=0.0000018)(FIGS. 4(a) and (b)), while kidney function was returned to normal compared to a significant increase in the untreated saline control group (Mean serum creatinine=1.2 μg/ml in the IL-28B group compared to a mean of 3.2 μg/ml in the untreated Adriamycin saline control group (p<0.05); mean naïve group serum creatinine=0.8 µg/ml)(FIG. 4(c)). Conditional survival increased from <50% in the untreated Adriamycin animals to 100% in those receiving IL-28 B (FIG. 4(d)). At 49 days, all kidneys from surviving mice ((naïve (n=10), untreated Adriamycin animals (n=18) and the IL-28B hydrodynamically transfected animals (n=22)) were fixed, paraffin-embedded, sectioned and stained with either haemotoxylin and eosin (H&E) or picosirius red (PSR) and imaged on a Hamamatsu slide scanner. Exemplar and representative images of the PSR-stained kidneys for one naïve, three untreated Adriamycin and three IL-28B-treated Adriamycin animals are shown in FIG. 5(a). Untreated mice kidneys had extensive glomerulosclerosis and tubulointerstitial fibrosis with notable tubular basement membrane expansion, flattening of the tubular epithelium, extensive tubular dilation with loss of the brush border and tubular atrophy. In contrast the IL28B treated mice were largely protected from both types of fibrotic remodelling. The 50 mouse kidney samples that were stained with PSR were subjected to high content image analysis using Definiens software and the area of PSR staining measured in the three groups was plotted as percentage PSR stained area (FIG. 5(b)). The IL-28B-treated group PSR stained area was normalised (p<0.0001) relative to the 3 fold increase in untreated kidneys The same 50 mouse kidney slides were subjected to a blinded pathological assessment of the degree of fibrosis by three individuals with renal pathology expertise. A clinical pathologist scored the H&E stained slides using a scoring range from 0-4 point scale (0 showing no fibrosis, and 4 the highest fibrosis). IL-28B treatment showed a significant 45% reduction in the pathology score (p<0.01) compared to the untreated group (FIG. 5(c)). Two expert renal scientists manually scored the 50 PSR-stained slides using a 1-10 scale (1 showing no fibrosis and 10 the highest). The IL-28B-treated group again demonstrated a clear improvement in the level of fibrotic remodelling (p<0.0001) relative to the untreated group (FIGS. 5(d) and (e)).

(2) Primary Human Cell In Vitro Models of Organ Fibrosis (2.1) Liver Fibrosis

Human primary stellate cells grown on plastic are self-activating and accumulate a substantial basal level of extracellular matrix as measured by the levels of the ECM proteins fibronectin, collagen IV and collagen I&III. This ECM accumulation can be inhibited by treatment of the culture with recombinant IL-28A in a dose dependent manner (FIG. 6(a)). The co-culture of human primary stellate cells with primary human hepatocytes (1:1 ratio) leads to a basal extracellular matrix that can also be inhibited by treatment with recombinant human IL-28A in a dose dependent manner with fibronectin, collagen IV and collagen I&III reduced (FIG. 6(b)).

TGFβ1 stimulation of both the stellate cell monoculture and the stellate-hepatocyte co-culture induced a further increase in the ECM proteins, fibronectin, collagen IV and collagen I&III. Treatment of the TGFβ1-stimulated stellate cell mono-culture, or the stellate-hepatocyte co-culture with either IL-28A or IL-28B demonstrated a near complete inhibition of any increase in any ECM protein at the highest concentration of 10 µg/ml of IL-28A or B, with both inhibiting in a dose dependent manner. IL-28A was more potent than IL-28B across all the ECM proteins in TGFβ1-stimulated liver cells (FIGS. 7(a) and (b)). Images of the TGFβ1-stimulated co-culture ECM in the presence of either IL-28A or IL-28B treated co-cultures show a clear reduction in ECM quantity compared to TGFβ1 treatment alone, being consistent with the image analysis quantification (FIG. 8).

(2.2) Small Intestine Fibrosis

Human small intestine fibroblasts stimulated with TGFβ1 (10 ng/ml) induce the extracellular matrix proteins, fibronectin and collagen I&III. The fibronectin level was significantly inhibited by IL-28A, IL-28B and IL-29 (10 ng/ml), with inhibition of 76%, 73%, and 83%, respectively relative to the control TGFβ1 stimulation. Collagen I&III was inhibited by IL-28A, IL-28B and IL-29 (10 ng/ml), by 48%, 33% and 35%, respectively. Collagen IV was only significantly inhibited by IL-28A (37% inhibition at 10 µg/ml) relative to control TGFβ1 stimulation (FIG. 9).

(2.3) Skin Fibrosis

Human primary dermal fibroblasts in co-culture with primary keratinocytes (9:1 ratio) accumulate a substantial amount of fibronectin, collagen I&III and collagen IV just by being in co culture. Using 3 separate batches of fibroblasts in combination with a single donor's keratinocytes, cultures were treated with either IL-28A or IL-28B. The percentage inhibition in ECM proteins relative to the untreated cultures was measured with all 3 fibroblast batches and the mean inhibition plotted (FIG. 10). Both IL-28A and IL-28B completely inhibited all 4 matrix proteins at the top concentration of 10 µg/ml with similar efficacy. Both IL-28A and IL-28B showed a dose-dependent inhibition of the Col IV ECM marker between 10 and 10000 ng/ml. Cell viability was tested using the prestoblue assay, showing that neither IL-28A nor IL-28B were toxic at any concentration tested (FIG. 10).

The dermal fibroblast-keratinocyte co-culture was treated with IL-29, IL-28A and IL-28B over a narrower concentration range of 1250-10000 ng/ml. This showed dose dependent inhibition of fibronectin, collagen I&III and collagen IV relative to the control co-culture (FIG. 11). Collagen IV was the most inhibited by the IFNLs at all concentrations tested (FIG. 11). Cell viability was not affected by treatment with IL-29, IL-28A or IL-28B as determined by the Presto Blue cell viability assay (FIG. 11).

Images of untreated dermal co-cultures compared to the IL-29, IL-28A and IL-28B treated co-cultures at both 1250 ng/ml and 10000 ng/ml, confirmed the total prevention of ECM accumulation determined by image analysis in the presence of the 10 ug/ml IFNL (FIG. 12).

Finally human dermal fibroblasts were stimulated in mono-culture with IL-1α (10 ng/ml) to induce the ECM proteins fibronectin, collagen I&III and collagen IV. Treatment of the IL-1α-stimulated fibroblast mono-cultures with IL-28A or IL-28B demonstrated a potent inhibition of the pro matrix response for all ECM proteins with complete inhibition of matrix at the top concentration of 10 µg/ml. IL-28A was more potent than IL-28B in all batches of fibroblasts, with one representative example depicted (FIG. 13). IL-28A or IL-28B had no effect on cell viability as measured by prestoblue (FIG. 13).

(2.4) Kidney Fibrosis

Human primary renal proximal tubular epithelial cells (RPTEC) placed in co-culture with human primary renal fibroblasts (seeded with 2000 cells/well at a 1:1 ratio) generate a robust ECM, high in fibronectin and collagen I&III. This co-culture was treated with IL-29, IL-28A or IL-28B using 3 different protocols for addition of cytokines.

Firstly IL-29, IL-28A and IL-28B were added to the renal co-culture at day 0 and the culture incubated for 7 days. All 3 cytokines potently inhibited in a dose-dependent manner the accumulation of fibronectin and collagen I&III (FIG. 14(a)). IL-29 demonstrated the most potent effects, with little difference between IL-28A and IL-28B. Cell viability was not compromised by cytokine treatment ((FIG. 14(a)).

Secondly IL-29, IL-28A and IL-28B were added to the RPTEC cells at day 0, the fibroblasts were added 24 hours later and then the culture was allowed to continue for a total of 7 days after which the ECM was measured. Here, IL-29, IL-28A and IL-28B all again inhibited in a dose dependent manner the accumulation of fibronectin and collagen I&III (FIG. 14(b)). The magnitude of the inhibition of the ECM proteins in the presence of the IFNLs was greater when the cytokines were added to the RPTECs 24 hours before the co-culture induction of ECM was initiated by the addition of the fibroblasts rather than to both cells simultaneously (Comparison of FIG. 14(a) and FIG. 14(b)).

Finally, IL-29, IL-28 and IL-28B were added to the fibroblasts on day 0. Twenty four hours later the RPTECs were added and the co-culture was continued for a total of 7 days when fibronectin and collagen I&III were measured. Adding the IFNLs to the fibroblasts first also showed significant inhibition of the ECM proteins (FIG. 14(c)), but reduced the efficacy of IL-29, IL-28A and IL-29B compared to both addition of the cytokines at day 0 to the co-culture and addition of the cytokines to the RPTEC 24 hours before the fibroblasts. This observation points to an IL-28R1-mediated signalling response in the RPTECs mediating an anti-fibrotic phenotype that results in an inhibition of the ECM signal in the co-culture of both epithelial and fibroblast cell types. To clearly demonstrate the differential effect of order of addition of the IFNLs to the different cell types versus simultaneous addition, IL-28A, IL-28B and IL-29 data was re-plotted for fibronectin (FIG. 15(a)) and for Col I&III (FIG. 15(b)) showing the relative effect of the different addition protocols on the level of inhibition for each individual IL-28R1 ligand. At certain lower concentrations of IL-28A, IL-28B or IL-29, the difference between the simultaneous addition of cells and cytokines compared to addition to the RPTECs first (before fibroblasts) reached statistical significance and these values are marked on the graphs.

Cell viability was not compromised by addition of the cytokines first to the RPTECs or fibroblasts before the alternate cell of the co-culture as read-out by presto blue (FIGS. 14(a), (b) and (c)).

Representative images (one out of a total of 16 fields per treatment) of the untreated co-culture compared to the IL-28A, IL-28B and IL-29 treated co-cultures show both the dose-dependent effects of IL-29, IL-28A and IL-28B and the near total inhibition observed in the presence of 1000 ng/ml IL-29 (FIG. 16) confirming the image analysis data.

Renal proximal tubular epithelial cells (RPTECs) in mono-culture lay down basal ECM proteins by growing on plastic, albeit at low levels. The low levels of ECM can still be inhibited in the presence of very low concentrations of IL-29 as shown for fibrobnectin, collagen IV and Collagen I&III in FIG. 22.

(2.5) Lung Fibrosis

Human primary small airway lung epithelial cells in co-culture with lung fibroblasts isolated from an idiopathic pulmonary fibrosis (IPF) patient (2000 cells/well at a 1:1 ratio) generated a robust total ECM (measured by flamingo staining) after 7 days in culture and was positive for the ECM markers, fibronectin, collagen I&III and collagen IV. IL-28A or IL-28B had no significant effect on the level of fibronectin. However, IL-28B demonstrated a significant inhibition of the collagen I&III, collagen IV and flamingo stains at the top concentration of 10 µg/ml (FIG. 17). However, the effects of IL-28A were less pronounced. There was no change in cell viability at 7 days with either IL-28A or IL-28B (FIG. 17).

(3) Primary Human Cell Models of Organ Fibrosis (3.1) Liver Fibrosis

The co-culture of human primary stellate cells with primary human intrahepatic biliary epithelial cells (1:1 ratio) leads to a basal extracellular matrix that can also be inhibited by treatment with recombinant human IL-28A and IL-29 in a dose dependent manner with fibronectin, collagen IV and collagen I&III reduced (FIG. 19).

(3.2) 3D Glomerular Spheroid Model

Glomerular spheroids were constructed from an inner core of magnetised human primary glomerular endothelial cells with an outer core of temperature conditional human podocytes that can be maintained in stable culture for up to 3 weeks. Treatment of the glomerular spheroids with 15% relapse plasma from patients with focal segmental glomerulosclerosis (FSGS) induced a loss of GFP-labelled podocytes from the outer core, which could be protected in the presence of IL-28A. Plasma from healthy volunteers had no effect on podocytes. Quantitation of the green fluorescent podocyte cell marker area demonstrated a significant reduction in the presence of FSGS relapse plasma that was significantly increased on IL-28A treatment (FIGS. 20(a), (b) and (c)). Clinical progression of FSGS is characterised by effacement and loss of podocytes. This model recreates the effect on podocytes from circulating factor in FSGS plasma and suggests clinical translatability of IL-28 therapy to prevent associated nephrotic syndrome and glomerulosclerosis.

(4) Mouse Unilateral Ureteral Obstruction Model (UUO) of Kidney Fibrosis (4.1) Mouse IL28B Delivered by Hydrodynamic Transfection (HDT)

UUO kidneys in animals receiving the control SEAP vector by HDT demonstrated tubulointerstitial fibrosis in the cortex typical of this model at 21 days post surgery with widespread expansion of the tubular basement membrane, strong collagen staining with the basement membrane particularly strongly stained within the medullary ray, widespread loss of epithelial cell volume, tubular atrophy, loss of proximal tubular brush border and extensive tubulointerstitial infiltrate. Less than 15% of tubules had near normal architecture. The medulla was effectively destroyed and missing while the changes to the glomeruli were minimal (FIG. 21(a)).

UUO kidneys in animals undergoing HDT with mouse IL-28B 1 day before UUO and those 7 days post UUO both showed protection from cortical tubulointerstitial fibrosis at 21 days post surgery (FIG. 21(a)). Tubular basement expansion and collagen staining was at least 30% to 40% lower in both groups receiving mouse IL-28B by HDT than in UUO mice receiving the control vector. Both IL28B groups had preservation of tubular architecture with less epithelial flattening and atrophy occurring. Between 30 and 40% of tubules showed near normal structure in those having HDT from day-1 prior to HDT and slightly less (20 to 30%) in those with later treatment. Interstitial infiltration was approximately 40% in both IL-28 groups in comparison to the control vector group. Neither IL28 group had any notable protection of medullary structure. Overall both early and late delivery of IL28B by HDT had significant protection from UUO induced fibrotic remodelling in the renal cortex.

The picro-sirius red (PSR) stained collagen sections were quantitated using definiens image analyses algorithms, showing the statistically significant protective effect of mouse IL-28B delivered either at day-1 or at day 7 when plotted as either total collagen area (FIG. 21(b)) or high intensity collagen area (FIG. 21 (c)) relative to the control plasmid treated mice. This is in agreement with the visual histological assessment of the stained sections as described above.

The serum levels of mouse IL28B protein achieved at day 21 post HDT in the mouse UUO model were measured by ELISA and were between 43 and 485 ng/ml across all the groups. No mouse IL28B protein could be measured in the control SEAP HDT mice so the levels were below 4 ng/ml which was the lower limit of quantitation (LLQ) of the assay used.

(4.2) Human IL-29 Delivered by Hydrodynamic Transfection (HDT)

Human IL-29 delivered by HDT shows significant protein expression in all mice at both day 0 (24 hours post-transfection) and at day 19 when the model was terminated compared to the SEAP control plasmid treated group (FIG. 23(a)). No human IL-29 could be detected in non-transfected or SEAP control mice sera.

The untreated 19 day UUO shows typical histological changes for this model. There is extensive destruction and loss of the renal medulla in all of the kidneys. The cortex displays a widespread expansion of the tubular basement membrane with significant interstitial collagen accumulation as shown by the increased picro-sirius red (PSR) staining. There is also a notable infiltration of cells into the interstitium throughout the whole cortex. The tubular epithelium structure is significantly damaged. The majority of epithelial cells have lost volume and generally appear flattened including a small number of tubules with a dilated lumen. Notably, greater than 80% of tubules have undergone extensive atrophy and in many cases collapsed completely. The lumen of the tubules are difficult to distinguish in most cases due to loss of patency, with epithelial cells clearly dislodged from the nephron tubular basement membrane and residing in what would have been the lumen.

Day 19 UUO kidneys treated from the time of UUO with IL-29 have a dramatically different appearance to those receiving just SEAP vector with the structure clearly preserved. The medulla is damaged, but remains present and has a more recognisable structure than the untreated UUO in 75% of animals. In the cortex, the primary observation at lower levels of magnification is a large number of tubules that have a dilated tubular lumen compared to the SEAP UUO. However, where this would be typically associated with very flattened epithelial cells and expansion of the tubular basement membrane in an untreated UUO, with IL-29 treatment the epithelial cells have retained volume, there is minimum expansion of the tubular basement membrane and the architecture of the tubules is significant preserved with little to no evidence of atrophy and tubular collapse. There is clearly lower levels of interstitial collagen and reduced expansion of the tubular basement membrane. Overall the application of IL-29 has reduced tubulointerstitial fibrosis caused by UUO significantly, with less interstitial collagen and a dramatic preservation of tubular architecture as shown by representative images in FIG. 23(b).

All the picro-sirius red (PSR) stained collagen sections were quantitated using definiens image analyses algorithms, showing the statistically significant protective effect of human IL-29 delivered at day-1 when plotted as total stained collagen area relative to the control SEAP plasmid treated mice (FIG. 23(c)). This is in agreement with the visual histological assessment of the stained sections as described above.

The invention claimed is:

1. A method of treating fibrosis, said method comprising: administering, to a subject having fibrosis, a therapeutically effective amount of a recombinant protein comprising the amino acid sequence of SEQ ID NO: 1, wherein the fibrosis is renal fibrosis, lung fibrosis, small intestine fibrosis, skin fibrosis, or liver fibrosis, and wherein the fibrosis is not associated with a hepatitis virus infection.

2. The method of claim 1, wherein the recombinant protein is pegylated.

3. The method of claim 1, wherein the recombinant protein is a fusion protein.

4. The method of claim 1, wherein the fibrosis is renal fibrosis.

5. The method of claim 1, wherein the fibrosis is lung fibrosis.

6. The method of claim 1, wherein the fibrosis is small intestine fibrosis.

7. The method of claim 1, wherein the fibrosis is skin fibrosis.

8. The method of claim 1, wherein the fibrosis is liver fibrosis.

9. The method of claim 1, wherein the recombinant protein is administered in combination with another therapeutically active compound.

10. The method of claim 9, wherein the other therapeutically active compound is an anti-fibrotic therapeutic agent.

* * * * *